US006630484B1

(12) United States Patent
Pearson et al.

(10) Patent No.: US 6,630,484 B1
(45) Date of Patent: *Oct. 7, 2003

(54) 6-AND 7-SUBSTITUTED ANALOGS OF SWAINSONINE THEIR PREPARATION AND THERAPEUTIC USE

(75) Inventors: William H. Pearson, Ann Arbor, MI (US); Erik J. Hembre, Ann Arbor, CA (US); Yi Ren, Ann Arbor, CA (US); Tanya M. Barber, Ann Arbor, MI (US)

(73) Assignee: The Regents of the University of Michigan, Ann Arbor, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 111 days.

(21) Appl. No.: 08/943,928

(22) Filed: Oct. 3, 1997

Related U.S. Application Data

(60) Provisional application No. 60/027,585, filed on Oct. 3, 1996.

(51) Int. Cl.$^7$ ............... A61K 31/44; C07D 221/02
(52) U.S. Cl. ............... 514/299; 546/112; 546/183
(58) Field of Search ............... 514/299; 546/183, 546/112

(56) References Cited

U.S. PATENT DOCUMENTS

| | | | | |
|---|---|---|---|---|
| 5,466,809 A | * | 11/1995 | Dime | ............... 546/183 |
| 5,621,106 A | * | 4/1997 | Dime | |
| 5,633,261 A | * | 5/1997 | Dime | |
| 5,773,239 A | * | 6/1998 | Carver | |
| 6,048,870 A | * | 4/2000 | Shah | |

OTHER PUBLICATIONS

CA 119:160615, Dime, 1993.*
zCA 123:218445, Dennis, 1995.*
CA 120:23093, Dennis, 1993.*
CA 117:234308, Chen, 1992.*
CA 122:265857, Picasso, 1994.*
CA 121:109350, Chen, 1994.*

* cited by examiner

Primary Examiner—D. Margaret Seaman
(74) Attorney, Agent, or Firm—Oblon, Spivak, McClelland, Maier & Neustadt, P.C.

(57) ABSTRACT

This invention relates to 6 or 7 substituted swainsonine analogues, processes for their preparation and use as therapeutic agents. The invention also relates to pharmaceutical compositions containing the compounds and their use as therapeutics.

19 Claims, 3 Drawing Sheets

6-AND 7-SUBSTITUTED ANALOGS OF SWAINSONINE THEIR PREPARATION AND THERAPEUTIC USE

This application claims priority to U.S. Provisional Patent Application Ser. No. 60/027,585, filed on Oct. 3, 1996, and which is incorporated herein by reference in its entirety.

FIELD OF THE INVENTION

This invention relates to novel analogs of swainsonine, processes for the preparation of these analogs, and their use as therapeutic agents.

BACKGROUND OF THE INVENTION

The α-mannosidase inhibitor swainsonine (1) continues to be the most promising anti-cancer agent among the polyhydroxylated alkaloids. Swainsonine inhibits the metastasis and growth rate of a number of human tumors in murine models,[1] and has entered clinical trials in humans. Swainsonine appears to exhibit its anti-cancer activity in a variety of ways. Swainsonine's anti-metastatic activity is associated with its ability to reduce tumor cell adhesion to the endothelium,[2,3] as well as its ability to inhibit tumor cell invasion through the extracellular matrix.[4–6] The anti-cancer activity of swainsonine is also associated with its ability to stimulate the immune system of the host. Swainsonine activates the natural killer cells (NK cells) that participate in the elimination of blood-borne B16-F10 melanoma cells,[7] and enhances lymphocyte activate killer cell (LAK cell) activity against human colon carcinoma cells in an interleukin-2 mediated fashion.[8] Further, swainsonine protects the host immune system against immunosuppressive proteins produced by tumors,[9] and stimulates bone marrow proliferation in the presence of cytotoxic anti-cancer drugs such as methotrexate, 5-fluorouracil, cyclophosphamide and doxorubicin.[10]

1

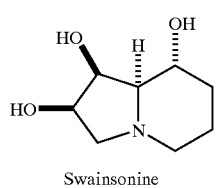

Swainsonine

The therapeutic activities of swainsonine are generally attributed to its ability to inhibit the Golgi glycoprotein processing enzyme mannosidase II. Inhibition of this enzyme allows for the formation of high-mannose and hybrid type glycoprotein oligosaccharides but prevents the formation of complex-type oligosaccharides. Since swainsonine inhibits glycoprotein processing at a relatively late stage in the pathway, it generally does not block membrane localization or secretion of glycoproteins, and thus shows less toxicity than glycoprotein inhibitors that act earlier in the pathway.

Swainsonine showed low preclinical toxicity in animals[11,12] and has entered Phase I clinical trials in humans. Initial results of these trials were reported recently.[13–15] Swainsonine was administered to 19 patients with advanced malignancies at levels of 50 to 550 μg/kg/day by continuous i.v. infusion over 5 days, repeated at 28 day intervals. Moderate toxicity was observed, with common side effects including edema, mild liver and pancreas dysfunction, increased serum amylase levels, and decreased serum retinol levels. Serum half-life was determined to be 0.5 days with a clearance rate of 2 mL/h•kg. Both Golgi α-mannosidase II and tissue lysosomal α-mannosidases were inhibited. Inhibition of the lysosomal α-mannosidase resulted in accumulation of oligomannosides observable by analysis of the urine. One possible treatment related death was reported, and at least three patients showed improvement over the course of treatment. Clinical trials studying chronic oral administration of swainsonine are currently in progress.

SUMMARY OF THE INVENTION

The present inventors report the preparation of swainsonine analogs such as 2, 3, and 4 shown below. Ring substitution at the 6- and 7-positions was found to afford increased selectivity for these analogs, in the following sense. The therapeutic activity of swainsonine is associated with its ability to inhibit the Golgi glycoprotein processing enzyme α-mannosidase II. However, swainsonine also inhibits the lysosomal

2

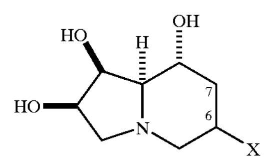

6-substituted swainsonine

3

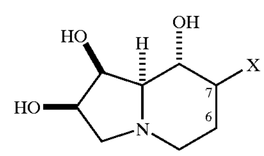

7-substituted swainsonine

4

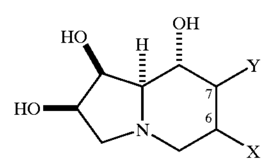

6,7-disubstituted swainsonine mannosidase that it responsible for the catabolic degradation of oligosaccharide chains. Inhibition of this enzyme leads to the accumulation of carbohydrates is tissues, a condition known as lysosomal storage, that is an unwanted side effect associated with the use of swainsonine as a therapeutic agent.[1] Unfortunately, swainsonine is more effective at inhibiting the lysosomal mannosidase (undesired) than the Golgi mannosidase (desired). An inhibitor that could discriminate between the glycoprotein processing and the lysosomal mannosidases would have clear advantages as a potential drug. Incorporation of substituents on swainsonine at C(6) and C(7), reported herein, affords the first swainsonine analogs with the ability to selectively inhibit α-mannosidase II rather than lysosomal mannosidase, a crucial selectivity for the advancement of these types of compounds for cancer chemotherapy.[1]

The present invention therefore relates to compounds with the formula I,

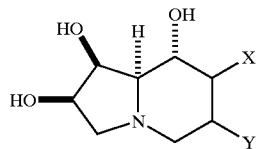

wherein X and Y may be any combination of the following groups, except that X and Y cannot both be hydrogen:
H (when the other group is not H)
$CH_3$
$(CH_2)_n CH_3$, where n=1–11
s-alkyl
$(CH_2)_n$—G, where G is branched alkyl, n=1–11
$(CH_2)_n$—Ar, where n=1–11; Ar=aryl, e.g. phenyl, substituted phenyl, naphthyl, substituted naphthyl, heteroaryl (e.g. pyridine, pyrimidine, pyrazine, triazine, furan, thiophene pyrrole, pyrazole, imidazole, triazole, thiazole, oxazole, isothiazole, isoxazole, and substituted versions thereof).
$(CH_2)_n$—FG, where n=1–11; FG=common functional groups or derivatized versions thereof (e.g. alkene, alkyne, substituted alkene, substituted alkyne, halide, alcohol, ether, amine, alkylated amine, carboxylic acid, carboxylic ester, acylated alcohol, acylated amine, sulfonamide, sulfide, thiol, sulfone, sulfoxide, sulfonated amine, azide, aldehyde, ketone, oxime, hydrazone, etc.)
$CH(OH)R^4$, where $R^4$=$CH_3$, n-alkyl, s-alkyl, $(CH_2)_n$—G, $(CH_2)_n$—Ar, $(CH_2)_n$—FG (see above for definitions of G, Ar, and FG)
$C(OH)R^4 R^5$, where $R^4$ and/or $R^5$=$CH_3$, n-alkyl, s-alkyl, $(CH_2)_n$—G, $(C_2)_n$—Ar, $(CH_2)_n$—FG (see above for definitions of G, Ar, and FG)
$R^4$—CO, where $R^4$=$CH_3$, n-alkyl, s-alkyl, $(CH_2)_n$—G, $(CH_2)_n$—Ar, $(CH_2)_n$—FG (see above for definitions of G, Ar, and FG), other ketone derivatives (e.g., oximes, hydrazones, etc.)
OH, OR, $OCOR^4$ (see above for $R^4$), other alcohol derivatives
$N_3$, $NH_2$, $NHR^4$, $NR^4 R^5$, $NHCOR^4$, $NR^4 COR^5$, $NHSO_2 R^4$, $NR^4 SO_2 R^5$, other amine derivatives PhS, PhS(O), $PhSO_2$
PhSe Owing to the chirality of I, it can exist in racemic and optically active forms. It is understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer.

PROCESSES FOR PREPARING COMPOUNDS

Figure 1A:
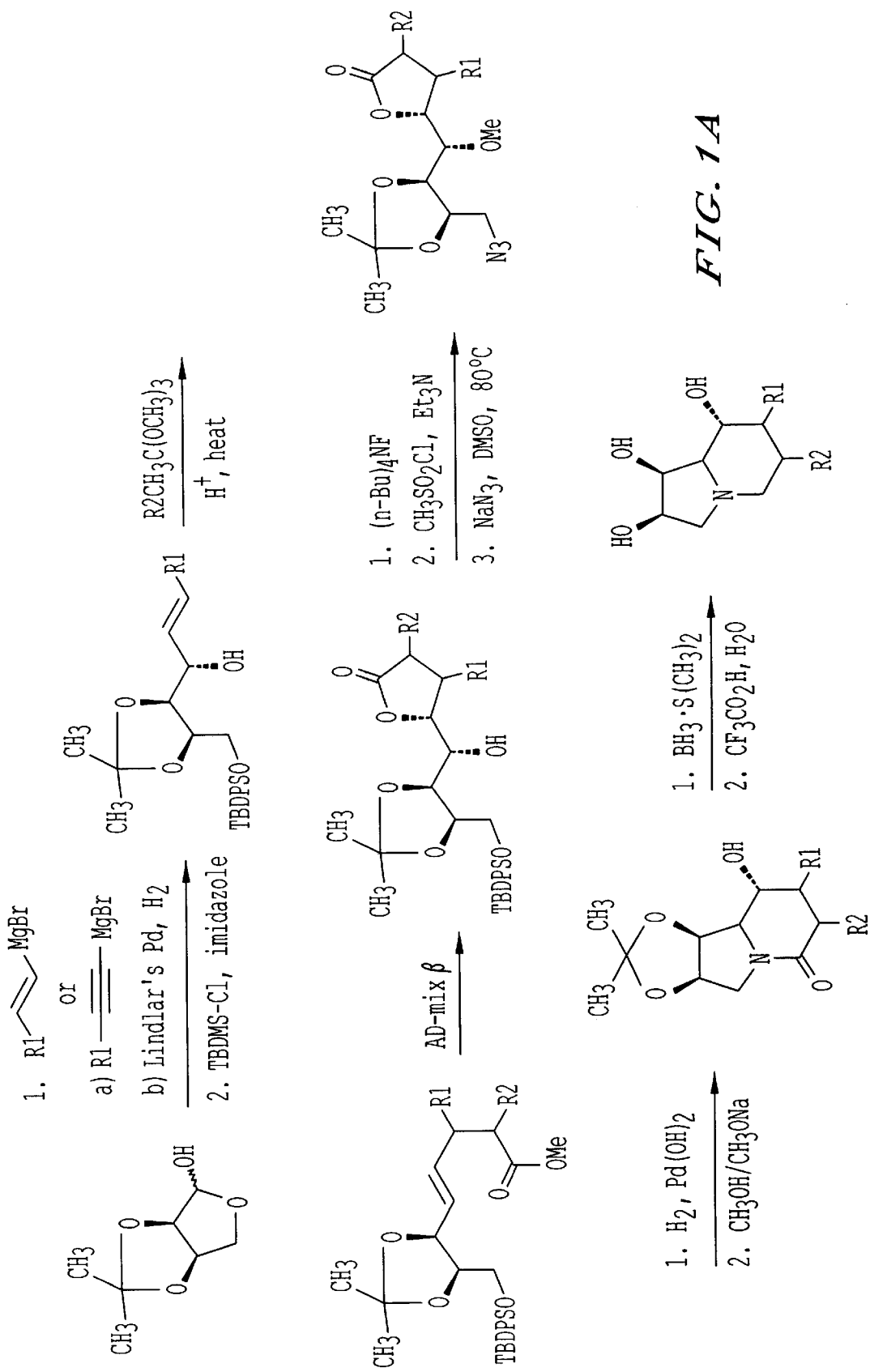
FIG. 1A: Synthesis of 6- and/or 7-substituted analogs of swainsonine.
Figure 1B:
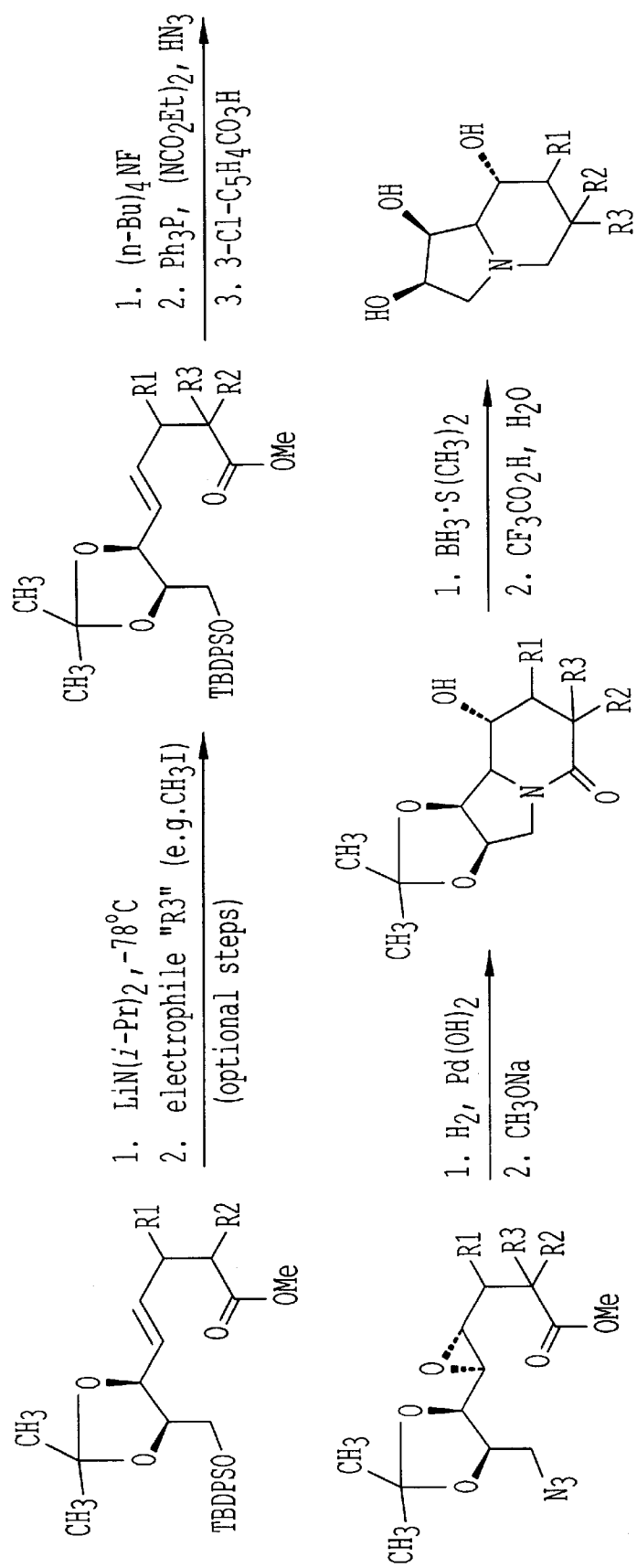
FIG. 1B: Synthesis of 6- and/or 7-substituted analogs of swainsonine wherein an additional substituent is introduced at C-6 by enolate alkylation.
Figure 1C:
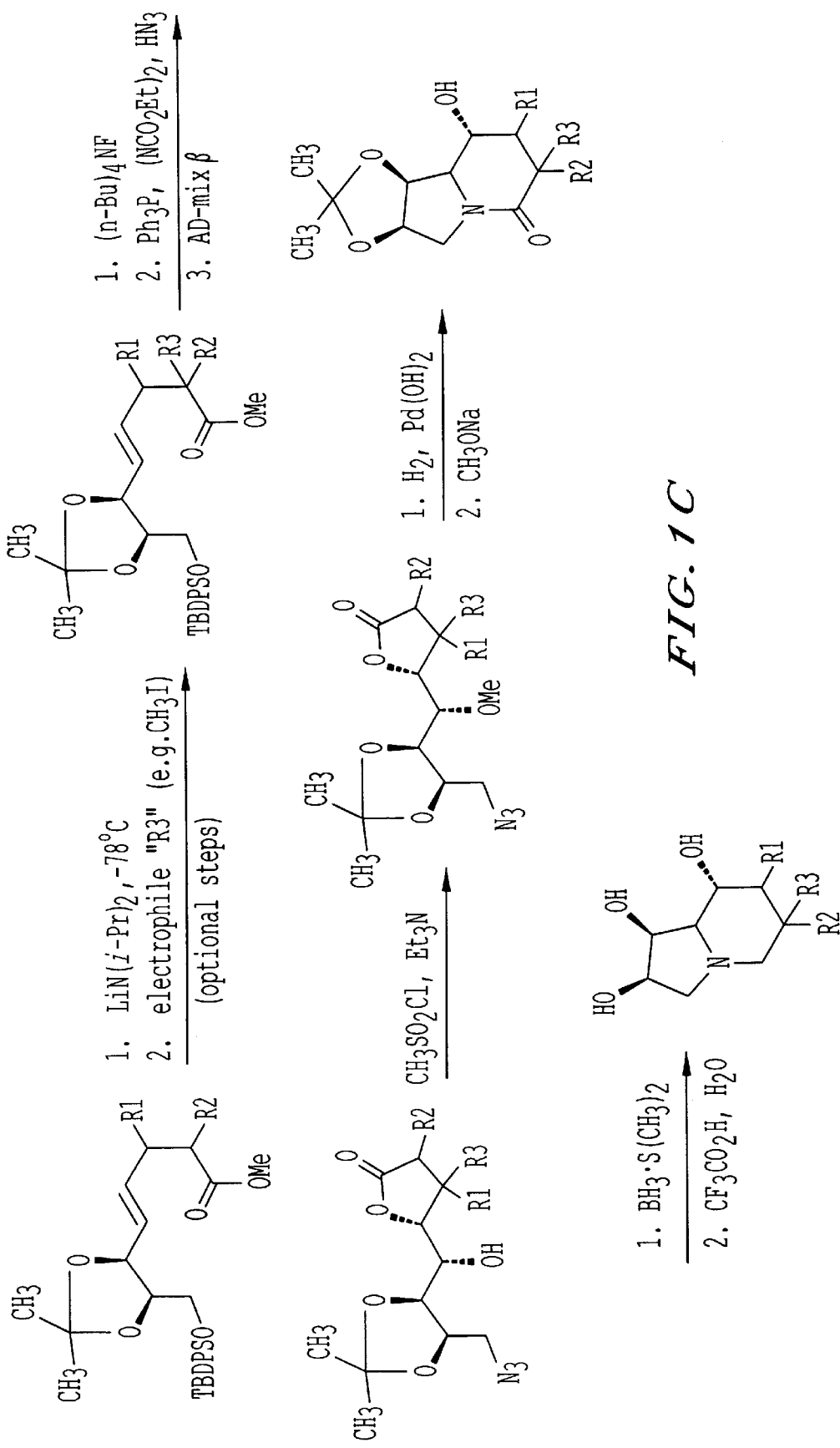
FIG. 1C: Alternate synthesis of 6- and/or 7-substituted analogs of swainsonine wherein an additional substituent is introduced at C-6 by enolate alkylation.

Preparation of 6-Substituted Swainsonine Analogs.

Two methods were used to synthesize 6-substituted swainsonine analogs. In the first route, a Claisen rearrangement[16,17] was used to introduce the substituent at an early stage in the synthesis of the analogs. In the second route, modification of a late stage intermediate using enolate chemistry was used to introduce the desired substituent later in the synthesis of the analogs.

I. CLAISEN ROUTE

Exemplary procedures for the synthesis of 6-substituted swainsonine analogs are shown in Schemes 1 and 2. Extension to the synthesis of analogs bearing different groups at C(6) can be also accomplished; the compounds shown are by way of example only.

Heating the known[18] allylic alcohol 5 with trimethylorthobutyrate or 4-(benzyloxy)-trimethylorthobutyrate promoted Claisen rearrangement[16] (Scheme 1). Subsequent silyl ether cleavage provided inseparable 1:1 mixtures of the α-substituted hydroxyesters 6a and 7a/b. Azide formation using the Mitsunobu procedure[19,20] likewise provided inseparable 1:1 mixtures of azides 8a/b and 9a/b. Oxidation with m-CPBA then provided mixtures of four diastereomeric epoxides that could be partially separated by chromatography. The ethyl series provides the epoxides (2S)-10α in 35%, (2R)-12αin 34% yield, and a 1:1 mixture of (2RS)-14β in 18% yield. The benzyloxyethyl substituted series provided the epoxides (2S)-11α in 28% yield, and a 1:1 mixture of (2RS)-15β in 22% yield.

Scheme 1:
Synthesis of the Azido Epoxyester Cyclization Precursors to Exemplary C(6)-Alkylated Swainsonine Analogs.

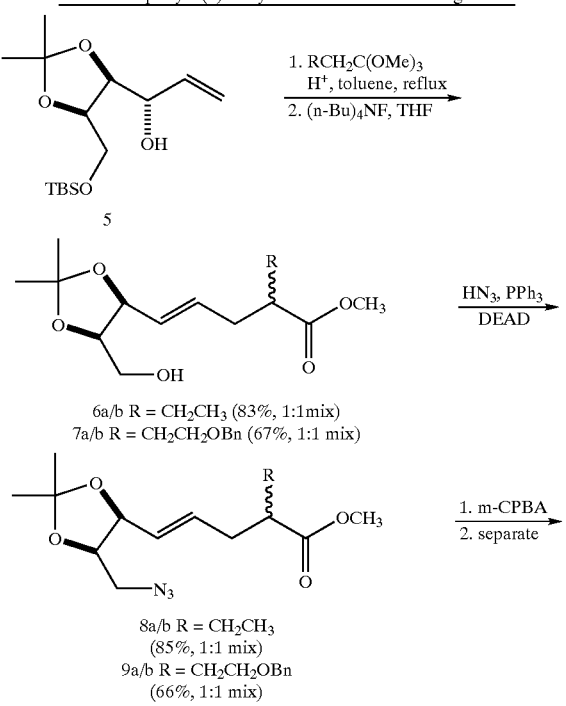

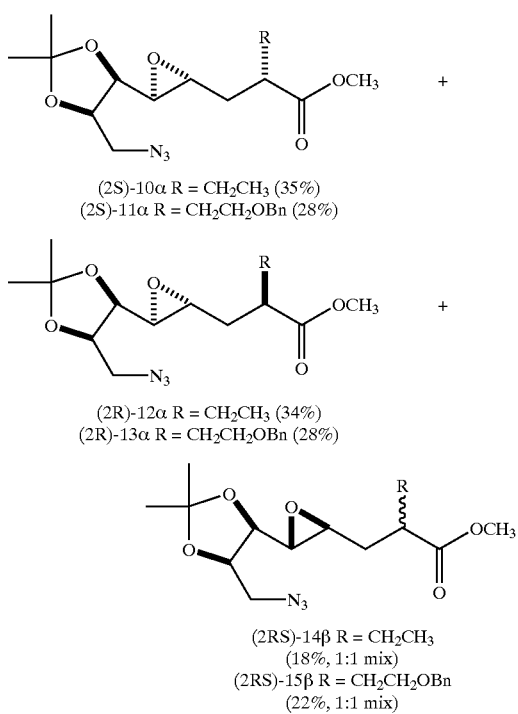

Reductive double cyclization of (2S)-10α and (2S)-11α required heating with sodium methoxide to promote the second ring closure, leading to clean formation of the bicyclic lactams 16 and 17 respectively (Scheme 2). Submission of epoxide (2R)-12α to these cyclization conditions, however, produced separable mixtures of the bicyclic lactams 18 (41%) and 16 (20%), while cyclization (2R)-13α led to a separable mixture of 19 (13%) and 17 (66%). The basic conditions required to promote lactam formation had promoted partial epimerization at the α-carbon to place the alkyl substituent in an equatorial position on the six-membered ring lactam. It was, in fact, this result that allowed the stereochemistry of the lactams and the preceding epoxides to be assigned. Analysis of the $^1$H NMR coupling constants for 16–19 are consistent with this assignment. The ratios of equatorial and axial substitution obtained here do not represent equilibrium mixtures, but instead represent the relative ratios at the time that the reaction was stopped because no more ester or lactone could be detected in the reaction mixtures. Attempts to prevent this stereochemical scrambling by using a milder cyclization catalyst such as sodium cyanide to promote lactam formation instead of sodium methoxide also resulted in extensive epimerization. Enough of the axially substituted derivatives 18 and 19 were obtained, however, to

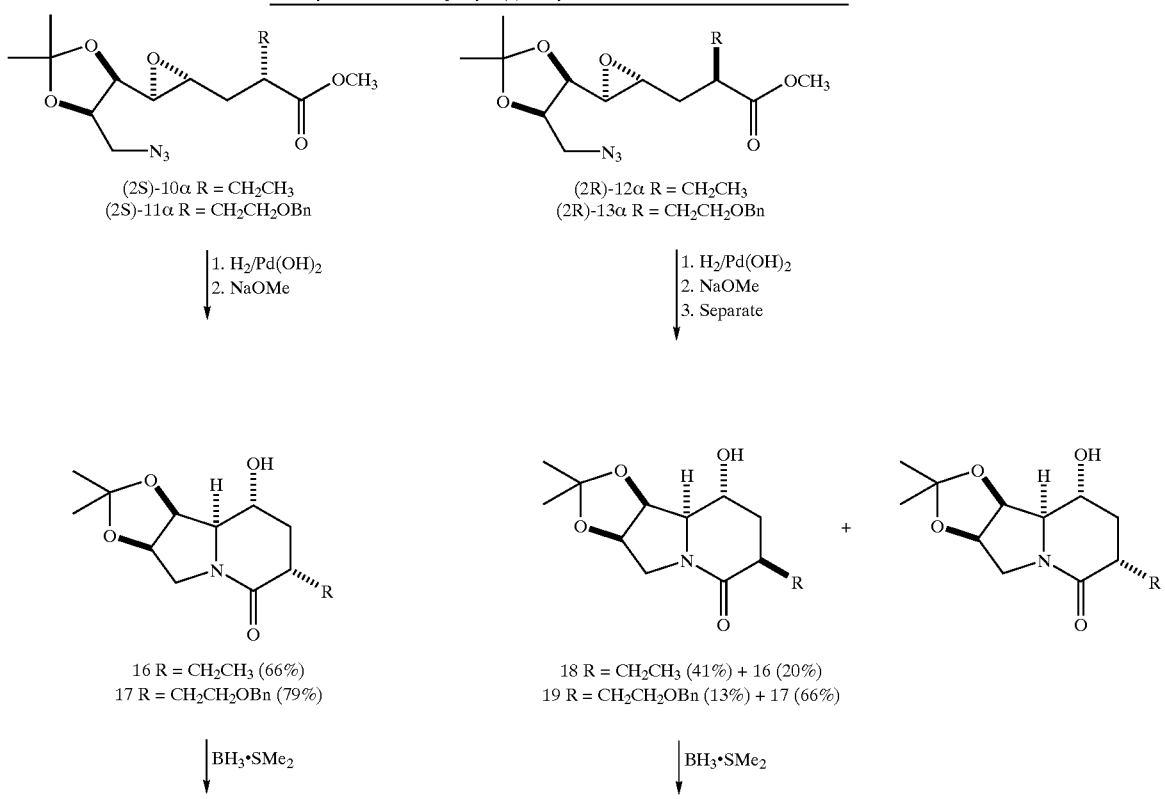

Scheme 2:
The Synthesis of Exemplary C(6)-Alkylated Swainsonine Derivatives 24–27.

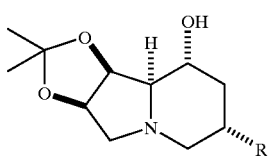

20 R = CH₂CH₃ (96%)
21 R = CH₂CH₂OBn (94%)

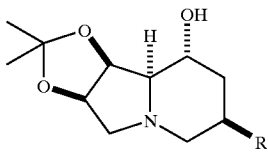

22 R = CH₂CH₃ (100%)
23 R = CH₂CH₂OBn (95%)

| 6N HCl/THF

| 6N HCl/THF

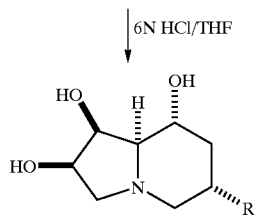

24 R = CH₂CH₃ (99%)
25 R = CH₂CH₂OBn (97%)

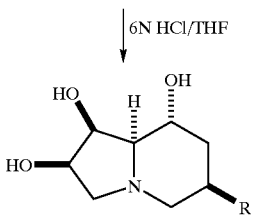

26 R = CH₂CH₃ (96%)
27 R = CH₂CH₂OBn (95%)

carry through the remainder of the synthesis. Reduction of the bicyclic lactams provided the bicyclic amines 20–23, which were then deprotected to afford the desired C(6)-substituted swainsonine analogs 24–27. Other substituents may be incorporated by this methodology, such as those shown in Scheme 2A.

Scheme 2A.
Claimed 6-Substituted Swainsonine Analogs
Available by the Claisen Rearrangement Route.

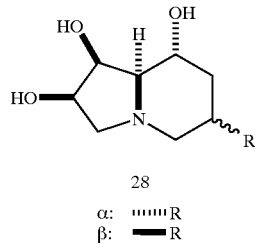

28

α: ''''''R
β: ━━R

R=(CH₂)ₙCH₃ (n=0–11)
R=s-alkyl
R=t-alkyl (CH₂)ₙAr (n=0–11, Ar=aryl, e.g. phenyl substituted phenyl, naphthyl, substituted naphthyl, heteroaryl (e.g. pyridine, pyrimidine, pyrazine, triazine, furan, thiophene pyrrole, pyrazole, imidazole, triazole, thiazole, oxazole, isothiazole, isoxazole, and subtituted versions thereof)
R=(CH₂)ₙFG (n=0–11, FG=common functional groups or protected versions thereof (e.g. alkene, alkyne, substituted alkene, substituted alkyne, halide, alcohol, ether, amine, alkylated amine, carboxylic acid, carboxylic ester, acylated alcohol, acylated amine, sulfonamide, sulfide, thiol, sulfone, sulfoxide, sulfonated amine, azide, etc.)

Finally, while the above route produces a separable mixture of stereoisomers at C(6), discreet stereoisomers may be made using the Ireland ester enolate Claisen rearrangement[17,21,22] (see Scheme 9 below).

II. ENOLATE ROUTE

Scheme 3 shows an alternative route to 6-substituted swainsonine analogs, one that introduces the substituent at a later stage of the synthesis. Lactams such as 29 are readily available.[23] Protection of the free hydroxyl as the silyl ether or other suitable protecting group (tetrahydropyranyl, (methoxy)methoxy, benzyl, other trialkylsilyl or aryldialkylsilyl) provided 30. Formation of the enolate of 30 with strong base followed by reaction with an electrophile (see Table 1) gave 31. Reduction of the lactam with borane gave 32, which was deprotected to the desired 6-substituted swainsonine analogs 33. A variety of C(6) substituents may be introduced (Table 1). Exemplary procedures are given in the experimental section. Mixtures of stereoisomers are often produced in the formation of 31, but these can be separated, and the undesired stereoisomer may be epimerized to afford more of the desired stereoisomer.

Scheme 3.
Synthesis of 6-Substituted Swainsonine Analogs using Enolate Chemistry

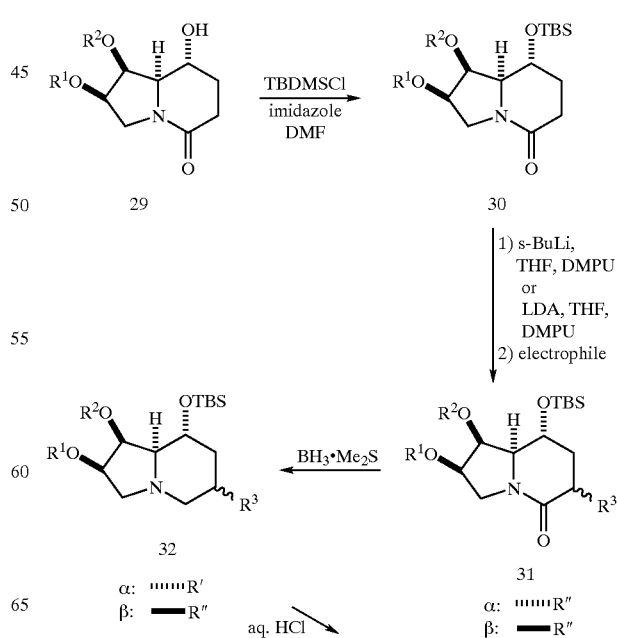

-continued

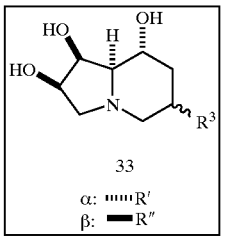

Abbreviations:
(TBS = t-butyldimethylsilyl)
DMPU = N,N-dimethylpropyleneurea
LDA = lithium diisopropylamide

33
α: ⫼R'
β: ▬R"

I. CLAISEN ROUTE

Exemplary procedures for the synthesis of 7-substituted swainsonine analogs are shown in Schemes 4–7. Extension to the synthesis of analogs bearing different groups at C(7) can be also accomplished; the compounds shown are by way of example only.

Propargylic alcohols 35 and 36 were prepared by adding hexynylmagnesium bromide or 4-(benzyloxy) butynylmagnesium bromide to the lactol derived from reduction of 2,3-O-isopropylidene-D-erythronolactone (34) (Scheme 4). Mekki et al. previously reported the addition of hexynylmagnesium bromide to 2,3-O-isopropylidene-D-erythrose and determined the anti:syn addition ratio to be

TABLE 1

| Electrophile | $R_3$ |
|---|---|
| $CH_3X$, where $X = Cl, Br, I$, OTs, OMs, OTf | $CH_3$ |
| $CH_3(CH_2)_n$—X, where $X = Cl, Br, I$, OTs, OMs, OTf and $n = 1–11$ | $CH_3(CH_2)_n$, where = 1–11 |
| s-alkyl-X, where $X = Cl, Br, I$, OTs, OMs, OTf | s-alkyl |
| G-$(CH_2)_n$—X, where $X = Cl, Br, I$, OTs, OMs, OTf; $n = 1–11$; G = branched alkyl | G-$(CH_2)_n$, where G is branched alkyl, $n = 1–11$ |
| Ar—$(CH_2)_n$—X, where $X = Cl, Br, I$, OTs, OMs, OTf; $n = 1–11$; Ar = aryl, e.g. phenyl substituted phenyl, naphthyl, substituted naphthyl, heteroaryl (e.g. pyridine, pyrimidine, pyrazine, triazine, furan, thiophene pyrrole, pyrazole, imidazole, triazole, thiazole, oxazole, isothiazole, isoxazole, and substituted versions thereof). | Ar—$(CH_2)_n$, where $n = 1–11$; Ar = aryl, e.g. phenyl, substituted phenyl, naphthyl, substituted naphthyl, heteroaryl (e.g. pyridine, pyrimidine, pyrazine, triazine, furan, thiophene pyrrole, pyrazole, imidazole, triazole, thiazole, oxazole, isothiazole, isoxazole, and substituted versions thereof). |
| G-$(CH_2)_n$—X, where $X = Cl, Br, I$, OTs, OMs, OTf; $n = 1–11$; FG = common functional groups or protected versions thereof (e.g. alkene, alkyne, substituted alkene, substituted alkyne, halide, alcohol, ether, amine, alkylated amine, carboxylic acid, carboxylic ester, acylated alcohol, acylated amine, sulfonamide, sulfide, thiol, sulfone, sulfoxide, sulfonated amine, azide, etc.) | FG-$(CH_2)_n$—X, where $n = 1–11$; FG = common functional groups or protected versions thereof (e.g. alkene, alkyne, substituted alkene, substituted alkyne, halide, alcohol, ether, amine, alkylated amine, carboxylic acid, carboxylic ester, acylated alcohol, acylated amine, sulfonamide, sulfide, thiol, sulfone, sulfoxide, sulfonated amine, azide, etc.) |
| $R^4$CHO, where $R^4 = CH_3$, n-alkyl, s-alkyl, $(CH_2)_n$-G, $(CH_2)_n$—Ar, $(CH_2)_n$-FG (see above for definitions of G, Ar, and FG) | CH(OH)$R^4$, where $R^4 = CH^3$, n-alkyl, s-alkyl, $(CH_2)_n$-G, $(CH_2)_n$—Ar, $(CH_2)_n$-FG (see above for definitions of G, Ar, and FG) |
| $R^4$C(OR)$R^5$, where $R^4$ and/or $R^5 = CH_3$, n-alkyl, s-alkyl, $(CH_2)_n$-G, $(CH_2)_n$—Ar, $(CH_2)_n$-FG (see above definitions of G, Ar, and FG) | C(OH)$R^4R^5$, where $R^4$ and/or $R^5 = CH_3$, n-alkyl, s-alkyl, $(CH_2)_n$-G, $(CH_2)_n$—Ar, $(CH_2)_n$-FG (see above for definitions of G, Ar, and FG) |
| $R^4$—CO—X, where $R^4 = CH_3$, n-alkyl, s-alkyl, $(CH_2)_n$-G, $(CH_2)_n$—Ar, $(CH_2)_n$-FG (see above for definitions of G, Ar, and FG) | $R^4$—CO, where $R^4 = CH_3$, n-alkyl, s-alkyl, $(CH_2)_n$-G, $(CH_2)_n$—Ar, $(CH_2)_n$-FG (see above for definitions of G, Ar, and FG), other ketone derivatives (e.g., oximes, hydrazones, etc.) |
| dimethyldioxirane, optionally followed by further derivatization using standard methods | OH, OR, OCOR$^4$ (see above for $R^4$), other alcohol derivatives |
| TrisylN$_3$, optionally followed by reduction to amine and potentially further derivatization using standard methods. | $N_3$, $NH_2$, NHR$^4$, NR$^4$R$^5$, NHCOR$^4$, NR$^4$COR$^5$, NHSO$_2$R$^4$, NR$^4$SO$_2$R$^5$, other amine derivatives |
| PhSCl or PhSSPh, optionally followed by oxidation with one or two equivalents of m-CPBA | PhS, PhS(O), PhSO$_2$ |
| PhSeCl | PhSe |

Preparation of 7-Substituted Swainsonine Analogs.

Two methods were used to synthesize 7-substituted swainsonine analogs. In the first route, a Claisen rearrangement[16,17] was used to introduce the substituent at an early stage in the synthesis of the analogs. In the second route, modification of a late stage intermediate using conjugate addition chemistry was used to introduce the desired substituent later in the synthesis of the analogs.

>99.1.[18] Reduction of the alkynes with sodium bis(2-methoxyethoxy)aluminum hydride (Red-Al) followed by protection of the primary hydroxyls provided the E-allylic alcohols 37 and 38. Heating with trimethylorthoacetate and acid in refluxing toluene, followed by silyl ether cleavage, then provided single stereoisomers of the E-γ,δ-unsaturated esters 40 and 41 in 74% and 79% yield respectively. The stereochemistry of the C(3) alkyl substituents in 40 and 41 was inferred from the most favorable chair-like transition state of the Claisen rearrangement 39.[17] Azide formation employing Mitsunobu conditions proceeded smoothly to afford the azides 42 and 43. Oxidation with m-CPBA then provided inseparable mixtures of the azido epoxyesters 44α/β (3:5:1) and 45α/β (3:1). The major epoxide product formed in both cases was that required to lead to the desired swainsonine C(8) and C(8a) stereochemistry after cyclization.

Scheme 4:
The Synthesis Exemplary Azido Epoxyesters 44α/β and 45α/β

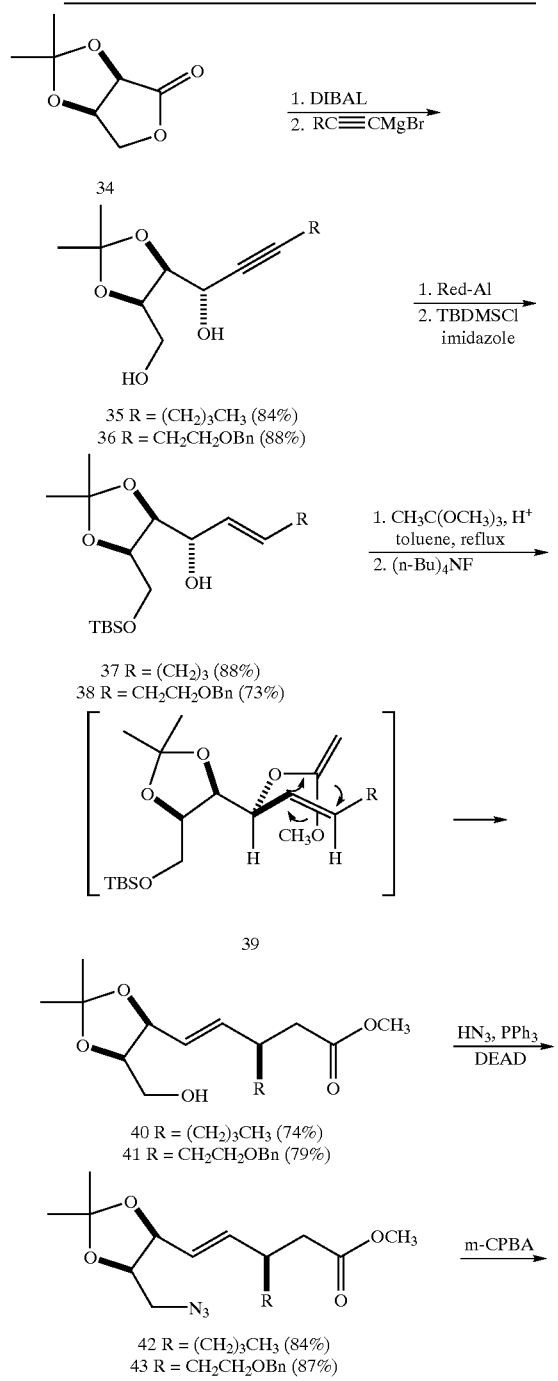

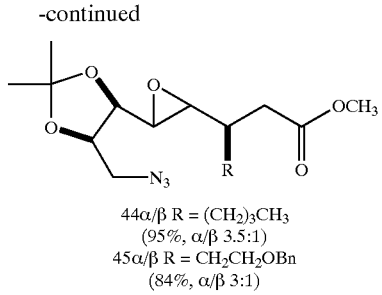

44α/β R = (CH$_2$)$_3$CH$_3$
(95%, α/β 3.5:1)
45α/β R = CH$_2$CH$_2$OBn
(84%, α/β 3:1)

Reductive double cyclization of the azido epoxyester mixtures 44α/β and 45α/β provided the separable bicyclic lactams 46 and 47, and 48 and 49 respectively (Scheme 5). Reduction of the lactams 46 and 47 to the bicyclic amines 50 and 51, followed by acetonide cleavage afforded the C(7)-substituted swainsonine analogs 52 and 53. The 8,8a-diepiswainsonine analogs 56 and 57 were also prepared in this series by an identical sequence of reactions.

Scheme 5:
The Synthesis of Exemplary 7-Substituted Swainsonine Analogs 52 and 53.

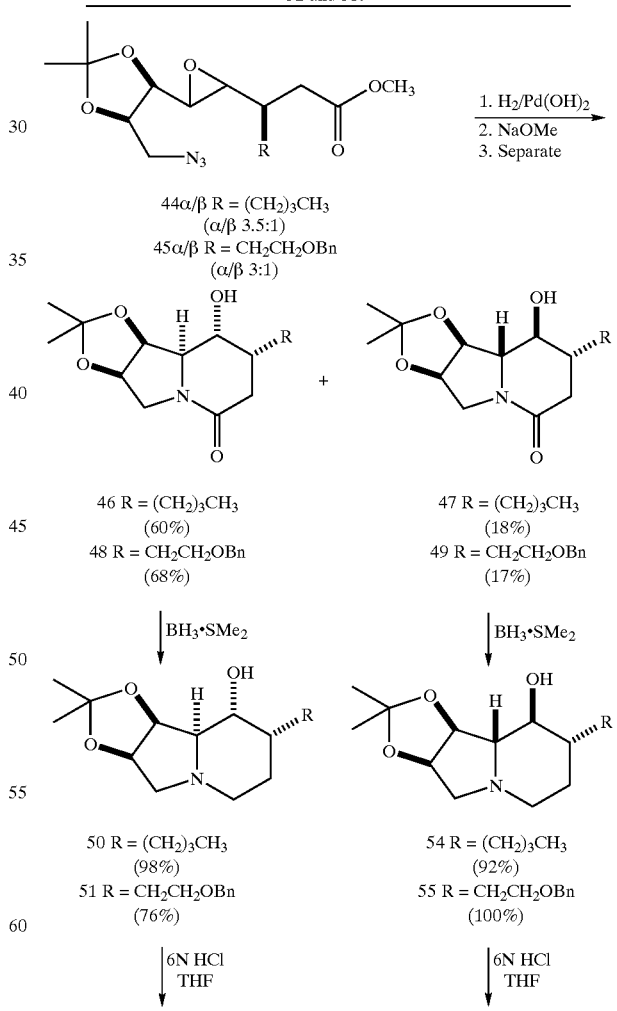

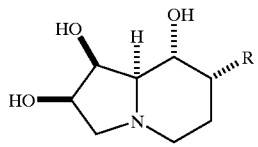

52 R = (CH$_2$)$_3$CH$_3$
(81%)
53 R = CH$_2$CH$_2$OBn
(97%)

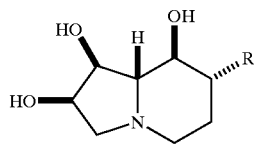

56 R = (CH$_2$)$_3$CH$_3$
(83%)
57 R = CH$_2$CH$_2$OBn
(86%)

The propargylic alcohols 35 and 36 could also be reduced to the Z-allylic alcohols using hydrogen and a poisoned palladium catalyst (Scheme 6). Silyl ether formation then led to 58 and 59. Claisen rearrangement with trimethylorthoacetate, followed by silyl ether cleavage afforded single stereoisomers of the hydroxyesters 61 and 62. Again, the C(3) stereochemistry of these compounds was inferred from the chair-like Claisen rearrangement transition state 60. Azide formation using the Mitsunobu conditions, followed by oxidation with m-CPBA provided inseparable mixtures of the azido epoxyesters 65α/β (2:1) and 66α/β (1.7:1). Once again, the major epoxide products of the mixtures were those required to access the proper swainsonine C(8) and C(8a) configuration after cyclization.

Scheme 6:
The Synthesis of Azido Epoxyesters 65α/β and 66α/β.

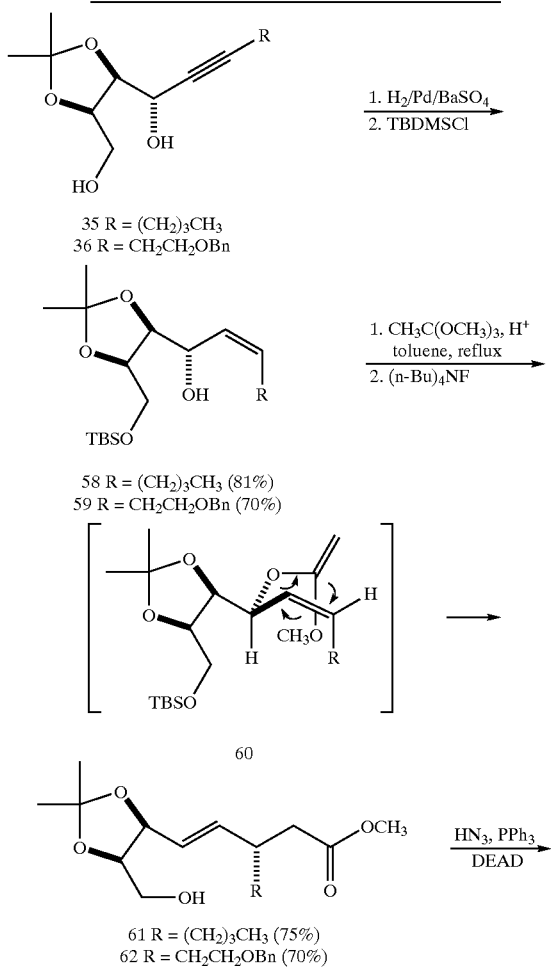

Reductive double cyclization of the azido epoxyester mixtures 65α/β provided mixtures of the bicyclic lactams 67 and 68, while cyclization of 66α/β provided 69 and 70. These lactams were difficult to separate. Reduction of the lactam mixtures with borane-methyl sulfide complex, however, provided the bicyclic amines 71 and 72, and 73 and 74, that were easily separated by chromatography. Final acetonide cleavage then afforded the C(7) alkylated swainsonine analogs 75 and 76 and the 8,8a-diepiswainsonine analogs 77 and 78.

Thus, both simple alkyl chain and functionalized alkyl chain C(7)-substituted swainsonine analogs are also readily available using the orthoester Claisen/azido epoxyester reductive double cyclization protocol. We were able to prepare these C(7) alkylated swainsonine analogs stereoselectively by performing the Claisen rearrangement on geometrically pure E or a Z-allylic alcohols.

Scheme 7:
The Synthesis of Exemplary 7-Substituted Swainsonine Analogs 75 and 76.

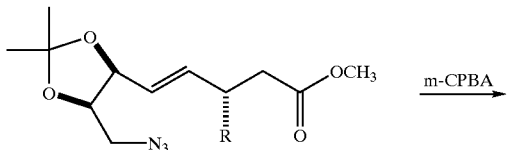

63 R = (CH$_2$)$_3$CH$_3$ (77%)
64 R = CH$_2$CH$_2$OBn (80%)

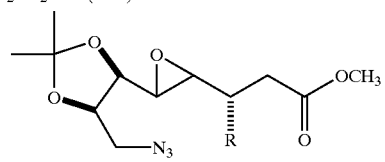

65α/β R = (CH$_2$)$_3$CH$_3$
[95%, (α/β 2:1)]
66α/β R = CH$_2$CH$_2$OBn
[75%, (α/β 1.7:1)]

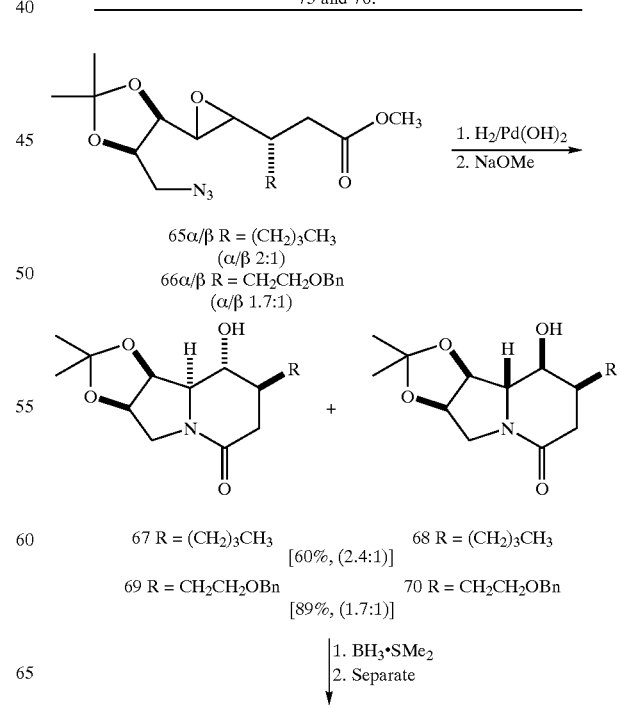

67 R = (CH$_2$)$_3$CH$_3$    68 R = (CH$_2$)$_3$CH$_3$
[60%, (2.4:1)]
69 R = CH$_2$CH$_2$OBn      70 R = CH$_2$CH$_2$OBn
[89%, (1.7:1)]

1. BH$_3$·SMe$_2$
2. Separate

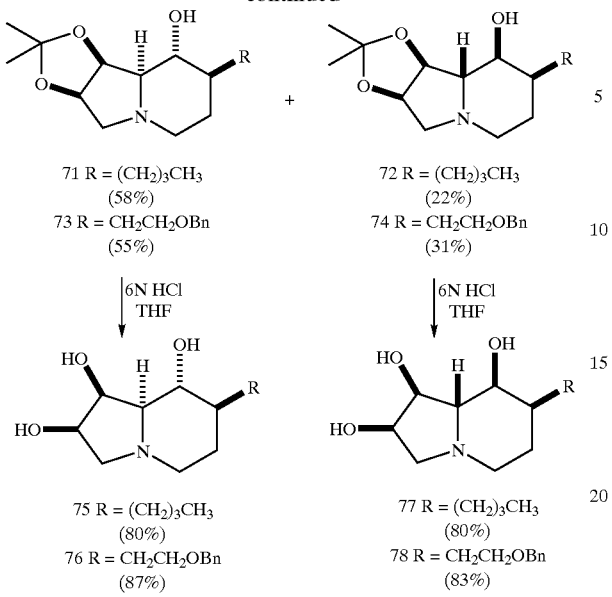

71 R = (CH$_2$)$_3$CH$_3$ (58%)
73 R = CH$_2$CH$_2$OBn (55%)

72 R = (CH$_2$)$_3$CH$_3$ (22%)
74 R = CH$_2$CH$_2$OBn (31%)

| 6N HCl
THF

75 R = (CH$_2$)$_3$CH$_3$ (80%)
76 R = CH$_2$CH$_2$OBn (87%)

77 R = (CH$_2$)$_3$CH$_3$ (80%)
78 R = CH$_2$CH$_2$OBn (83%)

Other substituents may be incorporated by this methodology, such as those shown in Scheme 7A.

Scheme 7A.
Claimed 7-Substituted Swainsonine Analogs Available by the Claisen Rearrangement Route.

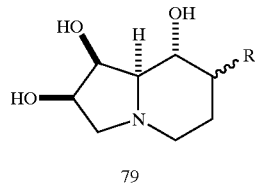

79

α: ⋯⋯R
β: ▬R

R=(CH$_2$)$_n$CH$_3$ (n=0–11)

R=s-alkyl

R=t-alkyl (CH$_2$)$_n$Ar (n=0–11, Ar=aryl, e.g. phenyl substituted phenyl, naphthyl, substituted naphthyl, heteroaryl (e.g. pyridine, pyrimidine, pyrazine, triazine, furan, thiophene pyrrole, pyrazole, imidazole, triazole, thiazole, oxazole, isothiazole, isoxazole, and subtituted versions thereof)

R=(CH$_2$)$_{11}$FG (n=0–11, FG=common functional groups or protected versions thereof (e.g. alkene, alkyne, substituted alkene, substituted alkyne, halide, alcohol, ether, amine, alkylated amine, carboxylic acid, carboxylic ester, acylated alcohol, acylated amine, sulfonamide, sulfide, thiol, sulfone, sulfoxide, sulfonated amine, azide, etc.)

II. CONJUGATE ADDITION ROUTE

The enone 80 was prepared by selenylation of the enolate of 30 and oxidative elimination. Access to a variety of 7-substituted swainsonine analogs is thus possible using standard conjugate addition chemistry,[24] as shown in Schemes 8 and 9. In Scheme 8, organocuprate chemistry is used to introduce the C(6) substituent. In Scheme 9, Lewis acid-mediated conjugate addition of silylated nucleophiles is used for a similar purpose.

Scheme 8.
Synthesis of 7-Substituted Swainsonine Analogs using Conjugate Addition of Organocuprates

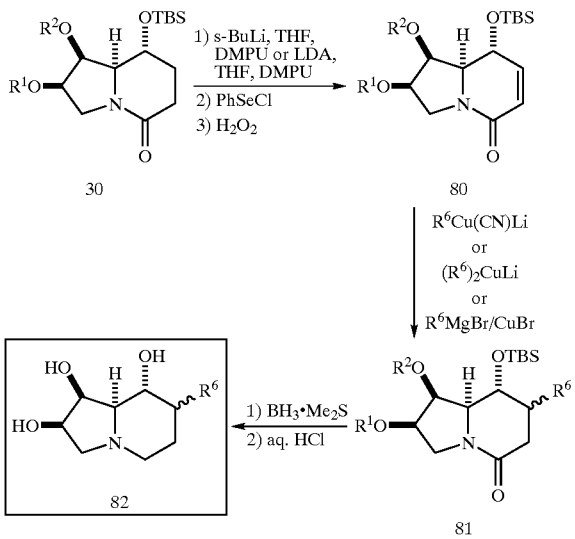

R$^6$=(CH$_2$)$_n$CH$_3$, (CH$_2$)$_n$Ar, (CH$_2$)$_n$FG, vinyl, alkenyl, Ar where n=0–11; Ar=aryl (e.g. phenyl substituted phenyl, naphthyl, substituted naphthyl, heteroaryl (e.g. pyridine, pyrimidine, pyrazine, triazine, furan, thiophene, pyrrole, pyrazole, imidazole, triazole, thiazole, oxazole, isothiazole, isoxazole, and subtituted versions thereof); FG=common functional groups or protected versions thereof (e.g. alkene, alkyne, substituted alkene, substituted alkyne, ether, protected amine, sulfide)

Scheme 8.
Synthesis of 7-Substituted Swainsonine Analogs using Lewis Acid Assisted Conjugate Additions

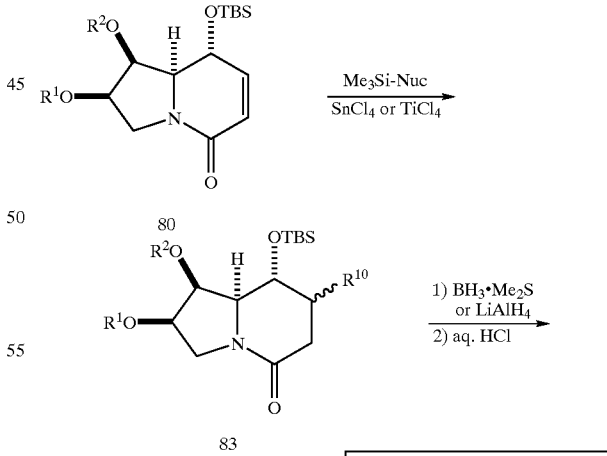

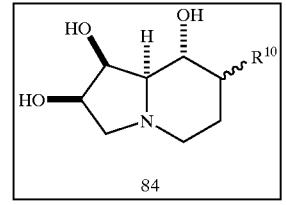

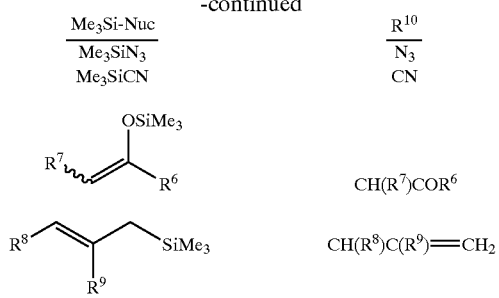

Preparation of 6,7-Disubstituted Swainsonine Analogs.

Two routes to 6,7-disubstituted swainsonine analogs may be employed, as shown in Schemes 9 and 10. In the first (Scheme 9), Claisen rearrangement chemistry is again used, but this time employing a hybrid of the two strategies described above for the 6- and 7-substituted analogs. In the second (Scheme 10), the enone chemistry shown in Scheme 8 is revisted, but instead, the enolate intermediate encountered in the introduction of the C(7) substituent by conjugate addition of an organocuprate is used as a nucleophile to introduce a C(6) substituent. Alternatively, Diels-Alder cycloaddition or 1,3-dipolar cycloaddition may be used to introduce both the C(6) and C(7) substituents simultaneously.

Scheme 9.
Synthesis of all diasteraomers of 6,7-disubstituted swainsonine analogs by the Cialsen rearrangement.

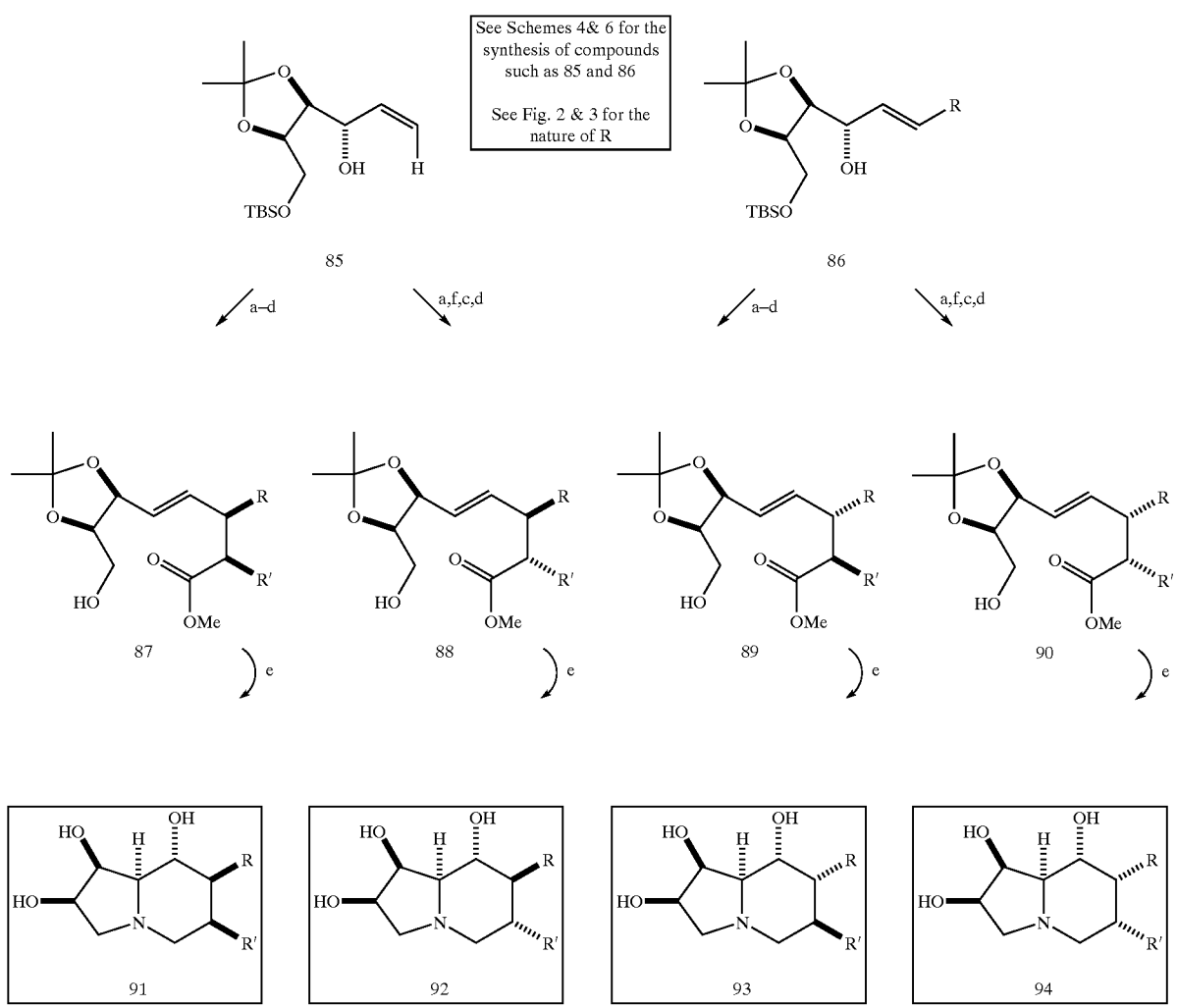

(a) RCH$_2$COCl, pyr (b) LDA, THF, HMPA (c) TBSCl, heat (d) CH$_2$N$_2$ (e) see Schemes 4–7 (f) LDA, THF

Scheme 10.
Synthesis of 6- and 7-Substituted Swainsonine Analogs Conjugate Addition/Enolate Trapping or Cycloaddition Chemistry

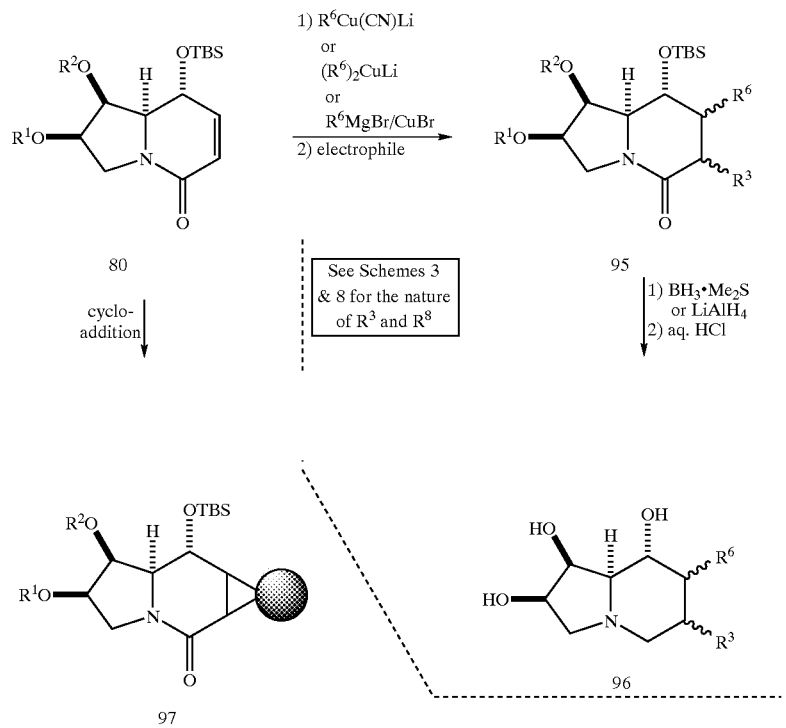

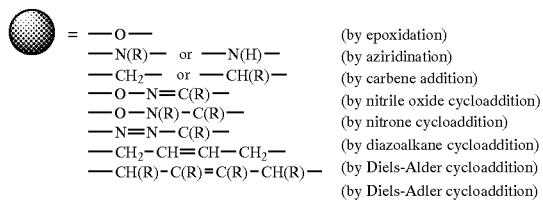

- ―O― (by epoxidation)
- ―N(R)― or ―N(H)― (by aziridination)
- ―CH$_2$― or ―CH(R)― (by carbene addition)
- ―O―N=C(R)― (by nitrile oxide cycloaddition)
- ―O―N(R)―C(R)― (by nitrone cycloaddition)
- ―N=N―C(R)― (by diazoalkane cycloaddition)
- ―CH$_2$―CH=CH―CH$_2$― (by Diels-Alder cycloaddition)
- ―CH(R)―C(R)=C(R)―CH(R)― (by Diels-Adler cycloaddition)

BIOLOGICAL ACTIVITY AND UTILITY OF THE COMPOUNDS OF THE INVENTION

All of the C(6) and C(7) alkylated swainsonine analogs were screened for inhibition activity against α-mannosidase from jack bean to ascertain their basic ability to inhibit mannosidase enzymes. The results of these screens are presented in Table 2. Alkylation of the swainsonine backbone provides compounds with varying degrees of α-mannosidase inhibitory activity. The analogs 24 and 26 that are equatorially substituted at the C(6) position of swainsonine retain the highest degree of inhibitory activity. Increasing the substituent size from ethyl (24) to benyloxyethyl (25) results in a slight decrease in inhibitory activity, while switching from equatorial to axial substitution at C(6) (26 and 27) results in a significant decrease in activity. In contrast, most of the C(7) butyl and benzyloxyethyl substituted compounds show complete loss of inhibitory activity except for 53 which is a weak inhibitor.

TABLE 2

Concentration of C(6) and C(7)-Alkylated Swainsonine Analogs Required to Inhibit Jack Bean α-Mannosidase by 50%. NI = Less than 50% inhibition at 1 mM concentrations.
Concentration Required for 50% Inhibitions ($\mu$M)

| Compound | α-Mannosidase (jack bean) | Compound | α-Mannosidase (jack bean) |
|---|---|---|---|
| 1 | 0.10 | | |
| 24 | 30 | 25 | 70 |
| 26 | 230 | 27 | 275 |
| 52 | NI | 53 | 890 |
| 54 | NI | 55 | NI |
| 77 | NI | 78 | NI |
| 56 | NI | 57 | NI |

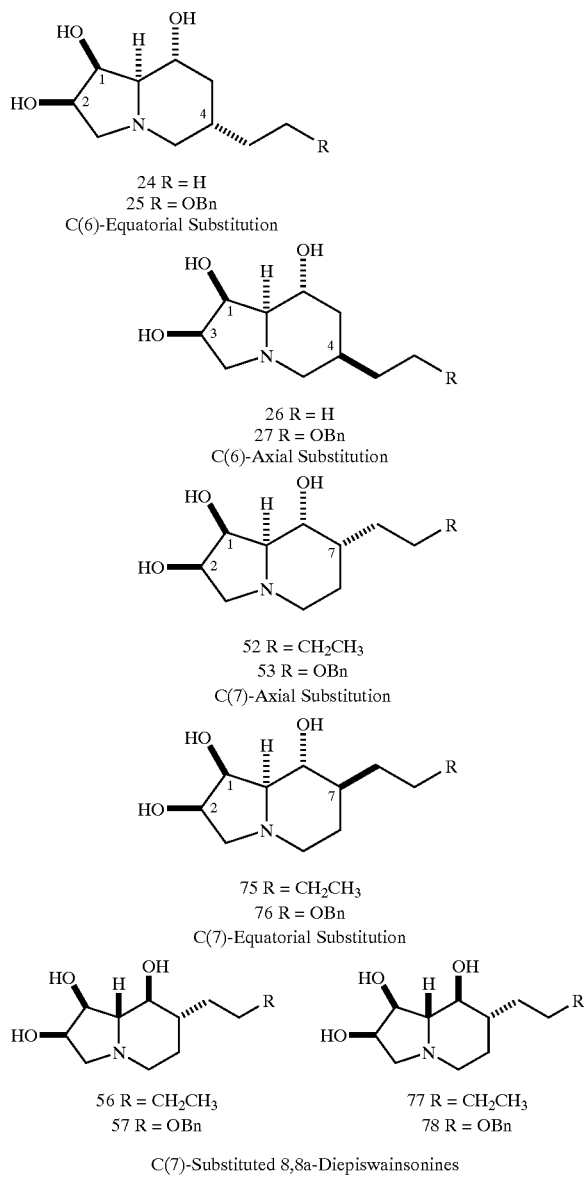

24 R = H
25 R = OBn
C(6)-Equatorial Substitution

26 R = H
27 R = OBn
C(6)-Axial Substitution

52 R = CH₂CH₃
53 R = OBn
C(7)-Axial Substitution

75 R = CH₂CH₃
76 R = OBn
C(7)-Equatorial Substitution

56 R = CH₂CH₃
57 R = OBn

77 R = CH₂CH₃
78 R = OBn

C(7)-Substituted 8,8a-Diepiswainsonines

Many of these compounds have also been examined[25] for their ability to inhibit the glycoprotein processing Golgi α-mannosidase II and the lysosomal mannosidase to ascertain whether the C(6) and C(7) substituents impart any selectivity in the inhibition of these enzymes (Table 3). Swainsonine (1), although a potent inhibitor of α-mannosidase II, is non-selective in that lysosomal mannosidase is inhibited approximately as well, an event that is believed to be responsible for the side-effects of swainsonine in clinical trails.[1] 24, 25, 26, 52, and 53 all show increased selectivity as high as 50-fold for 52) for inhibition of α-mannosidase II over lysosomal mannosidase, providing evidence that these compounds may be useful for cancer chemotherapy without the side-effects of swainsonine. The ability of these compounds to inhibit α-mannosidase II correlates with anticancer activity.[1] The diminished activity against lysosomal mannosidase is a desirable additional feature, leading to fewer side-effects in chemotherapy.

TABLE 3

Comparison of IC$_{50}$ Data for the Inhibition of α-Mannosidase II by Swainsonine and Selected 6- and 7-Substituted Swainsonine Analogs and Selectivities for Inhibition of α-Mannosidase II vs. Lysosomal Mannosidase (ratio M/L = ratio of activities of α-Mannosidase II/lysosomal mannosidase; smaller is better).[25]

| Compound | Inhibition of α-mannosidase II mean IC$_{50}$ (mM) | ratio M/L (smaller is better) |
|---|---|---|
| swainsonine (1) | 0.084 | 0.8 |
| (6S)-6-ethyl-swainsonine (24) | 2.17 | 0.2 |
| (6S)-6-(2-benzyloxy)ethyl-swainsonine (25) | 5.12 | 0.33 |
| (6R)-6-ethyl-swainsonine (26) | 44.5 | 0.47 |
| (7R)-7-n-butyl-swainsonine (52) | 28.5 | 0.02 |
| (7S)-7-(2-benzyloxy)ethyl-swainsonine (52) | 5.3 | 0.24 |
| (7R)-7-n-butyl-8,8a-diepi-swainsonine (56) | 2000 | — |

TABLE 3-continued

Comparison of IC$_{50}$ Data for the Inhibition of α-Mannosidase II by Swainsonine and Selected 6- and 7-Substituted Swainsonine Analogs and Selectivities for Inhibition of α-Mannosidase II vs. Lysosomal Mannosidase (ratio M/L = ratio of activities of α-Mannosidase II/lysosomal mannosidase; smaller is better).[25]

| Compound | Inhibition of α-mannosidase II mean IC$_{50}$ (mM) | ratio M/L (smaller is better) |
|---|---|---|
| (7S)-7-n-butyl-swainsonine (75) | 2000 | — |
| (7S)-7-n-butyl-8,8a-diepi-swainsonine (77) | 2000 | — |

EXAMPLES OF SYNTHETIC PROCEDURES

The following non-limiting examples are illustrative of the present invention:

PART I: Synthesis of 6-Substituted Swainsonine Analogs by Incorporation of the C(6) Substituent Using a Claisen Rearrangement.

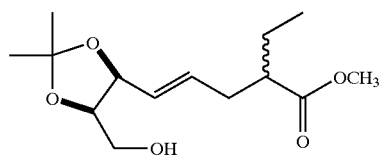

6a/b

Methyl (E)-(2S,6S,7R)-2-Ethyl-8-hydroxy-6,7-O-isopropylidenedioxy-4-octenoate and Methyl (E)-(2R,6S,7R)-2-Ethyl-8-hydroxy-6,7-O-isopropylidenedioxy-4-octenoate (6a/b). Trimethyl orthobutyrate (8.5 mL, 7.9 g, 53 mmol) and propionic acid (39 mg, 0.53 mmol) were added to the neat allylic alcohol 5[18] (1.60 g, 5.31 mmol). The flask was fitted with a distillation head and was heated in an oil bath (125° C.), distilling off methanol as it formed. After 24 h, the mixture was cooled to room temperature and concentrated. The crude residue was dissolved in THF (25 mL), cooled to 0° C., and tetra-n-butylammonium fluoride (5.9 mL of a 1 M soln. in THF, 5.9 mmol) was added in a dropwise fashion. After 2 h, the solution was diluted with ether (100 mL) and washed with brine (2×50 mL). The aqueous layers were back-extracted with EtOAc (100 mL), then the combined organic layers were dried (MgSO$_4$), and concentrated. Chromatography (3:1 hex/EtOAc) provided 1.20 g (83%) of an inseparable mixture (1:1) of diastereomeric alcohols 6a/b as a pale yellow oil. Characterization was performed on the mixture. R$_f$=0.27 (2:1 hex/EtOAc); $^1$H NMR (CDCl$_3$, 360 MHz) δ 5.74 (m, 1H), 5.54 (dd, J=7.8, 16.4 Hz, 1H), 4.61 (dt, J=4.3, 7.1 Hz, 1H), 4.21 (ddd, J=1.3, 5.7, 12.5 Hz, 1H), 3.68 (s, 3H), 3.55 (m, 2H), 2.4 (m, 2H), 2.28 (m, 1H), 2.04 (m, 1H), 1.5–1.7 (m, 2H), 1.49 (s, 3H), 1.37 (s, 3H), 0.90 (t, J=7.4 Hz, 3H); $^{13}$C NMR (CDCl$_3$, 90 MHz) δ 175.9, 175.9, 132.7, 132.3, 127.1, 126.9, 108.6, 78.3, 782., 77.9, 77.8, 61.9, 51.5, 46.7, 46.6, 34.4, 34.2, 27.8, 25.2, 25.1, 24.8, 11.6; IR (neat) 3483 (m, br), 2936 (m), 1737 (s) cm$^{-1}$; MS (CI, NH$_3$) m/z (rel intensity) 290 [(M+NH$_4$)+, 6], 215 (100), 202 (43), 185 (23); HRMS (CI, NH$_3$) calcd for C$_{14}$H$_{24}$O$_5$NH$_4$ [(M+NH$_4$)$^+$] 290.1967, found 290.1973.

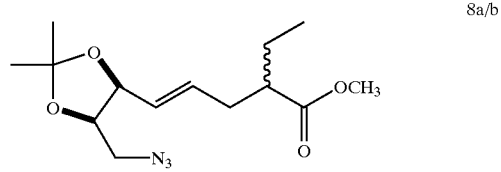

8a/b

Methyl (E)-(2S,6S,7R)-8-Azido-2-ethyl-6,7-O-isopropylidenedioxy-4-octenoate and Methyl (E)- (2R,6S,7R)-8-Azido-2-ethyl-6,7-O-isopropylidenedioxy-4-octenoate (8a/b). Hydrazoic acid (9.6 mL of a 1.2 M solution in benzene, 11.5 mmol)[26] was added to a solution of the alcohol 6a/b (1.56 g, 5.73 mmol) and triphenylphosphine (2.25 g, 8.59 mmol) in benzene (29 mL). The mixture was cooled to 5° C. and diethyl azodicarboxylate (1.41 mL, 8.59 mmol) was added in a dropwise fashion. The solution was then allowed to warm to room temperature. After 1.5 h, TLC indicated that starting material was still present. More hydrazoic acid solution (4.9 mL, 5.7 mmol), triphenylphosphine (0.75 g, 2.87 mmol), and DEAD (0.47 mL, 2.87 mmol) were added and the mixture was allowed to stir at room temperature for another 1 h. The mixture was then poured into hexanes (80 mL), resulting in the formation of a white precipitate. The mixture was filtered and the filtrate was concentrated. Chromatography (15:1 to 10:1 hexane/EtOAc) provided 1.50 g (85%) of an inseparable mixture (1:1) of diastereomeric azides 8a/b as a colorless oil. Characterization was performed on the mixture. R$_f$=0.42 (5:1 hex/EtOAc); $^1$H NMR (CDCl$_3$, 300 MHz) δ 5.75 (m, 1H), 5.49 (m, 1H), 4.60 (m, 1H), 4.25 (td, J=4.3, 7.0 Hz, 1H), 3.67 (s, 3H), 3.26 (dd, J=7.7, 12.8 Hz, 1H), 3.15 (dd, J=4.3, 12.8 Hz, 1H), 2.39 (m, 2H), 2.26 (m, 1H), 1.5–1.7 (m, 2H), 1.51 (s, 3H), 1.37 (s, 3H), 0.90 (t, J=7.4 Hz, 3H); $^{13}$C NMR (CDCl$_3$, 75 MHz) δ 175.5, 132.9, 132.7, 126.5, 126.3, 109.0, 77.9, 77.8, 76.9, 51.6, 51.4, 46.7, 46.6, 34.4, 34.3, 27.8, 25.3, 25.1, 24.9, 11.6; IR (neat) 2937 (m), 2102 (s), 1736 (s) cm$^{-1}$; MS (CI, NH$_3$) m/z (rel intensity) 315 [(M+NH$_4$)$^+$, 16], 270 (79), 240 (100), 212 (18); HRMS (CI, NH$_3$) calcd for C$_{14}$H$_{23}$N$_3$O$_4$NH$_4$ [(M+NH$_4$)$^+$] 315.2032, found 315.2042.

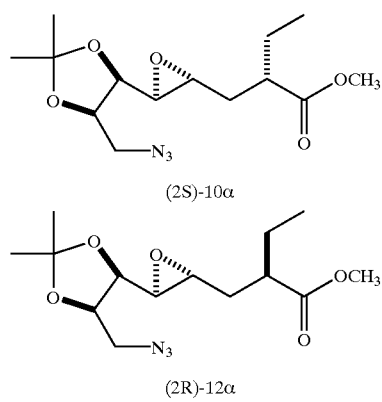

(2S)-10α

(2R)-12α

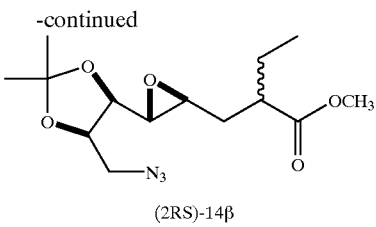

(2RS)-14β

Methyl (2S,4R,5S,6R,7R)-8-Azido-4,5-epoxy-2-ethyl-6,7-O-isopropylidenedioxyoctanoate [(2S)-10α], Methyl (2R,4R,5S,6R,7R)-8-Azido-4,5-epoxy-2-ethyl-6,7-O-isopropylidenedioxyoctanoate [(2S)-12α], Methyl (2S,4S,5R,6R,7R)-8-Azido-4,5-epoxy-2-ethyl-6,7-O-isopropylidenedioxyoctanoate [(2S)-14β], and Methyl (2R,4S,5R,6R,7R)-8-Azido-4,5-epoxy-2-ethyl-6,7-O-isopropylidenedioxyoctanoate [(2R)-14β]. m-Chloroperbenzoic acid (2.65 g, technical grade, 2.12 g pure, 12.3 mmol) was added to a cooled (0° C.) solution of the azide (8a/b) (1.46 g, 4.91 mmol) in CH$_2$Cl$_2$ (25 mL). After 24 h, the mixture was diluted with ether (100 mL) and washed with 1 M NaOH (2×50 mL). The aqueous layers were back-extracted with ether (2×50 mL) and the combined organic layers were washed with saturated NaHCO$_3$ (100 mL) and brine (50 mL), then dried (MgSO$_4$), filtered, and concentrated. Chromatography (15:1 to 10:1 hex/EtOAc gradient) provided 0.54 g (35%) of the epoxide isomer (2R)-12α as a pale yellow oil, followed by 0.52 g (34%) of the epoxide isomer (2S)-10α as a pale yellow oil, followed by 0.28 g (18%) of an inseparable mixture (1:1) of diastereomeric epoxides (2RS)-14β.

Data for (2S)-10α: R$_f$=0.52 (3:1 hex/EtOAc); [α]$^{23}_D$=+64.4° (c 0.80, CHCl$_3$); $^1$H NMR (CDCl$_3$, 300 MHz) δ 4.35 (td, J=4.2, 6.8 Hz, 1H), 3.71 (s, 3H), 3.69 (dd, J=6.4, 7.9 Hz, 1H), 3.58 (dd, J=4.2, 13.0 Hz, 1H), 3.51 (dd, J=7.0, 13.0 Hz, 1H), 2.87 (ddd, J=2.0, 4.6, 6.8 Hz, 1H), 2.80 (dd, J=2.0, 8.0 Hz, 1H), 2.52 (m, 1H), 2.02 (ddd, J=4.6, 9.8, 14.2 Hz, 1H), 1.55–1.75 (m, 3H), 1.52 (s, 3H), 1.36 (2, 3H), 0.91 (t, J=7.5 Hz, 3H); $^{13}$C NMR (CDCl$_3$, 75 MHz) δ 175.4, 109.9, 77.4, 76.7, 56.6, 55.3, 51.6, 50.6, 44.1, 33.6, 27.6, 25.7, 25.1, 11.6; IR (neat) 2967 (m), 2102 (s), 1735 (s) cm$^{-1}$; MS (CI, NH$_3$) m/z (rel intensity) 331·[(M+NH$_4$)$^+$, 22], 314 (47), 286 (100), 254 (53), 228 (30), 142 (44); HRMS (CI, NH$_3$) calcd for C$_{14}$H$_{23}$N$_3$O$_5$NH$_4$ [(M+NH$_4$)$^+$] 331.1981, found 331.1975.

Data for (2R)-12α: R$_f$=0.45 (3:1 hex/EtOAc); [α]$^{23}_D$=+50.6° (c 0.87, CHCl$_3$); $^1$H NMR (CDCl$_3$, 300 MHz) δ 4.35 (td, J=4.2, 6.8 Hz, 1H), 3.71 (s, 3H), 3.70 (m, 1H), 3.58 (dd, J=4.2, 13.1 Hz, 1H), 3.52 (dd, J=6.9, 13.0 Hz, 1H), 2.91 (td, J=2.0, 5.8 Hz, 1H), 2.77 (dd, J=2.0, 7.9 Hz, 1H), 2.50 (m, 1H), 1.82 (m, 2H), 1.55–1.75 (m, 2H), 1.52 (s, 3H), 1.36 (s, 3H), 0.91 (t, J=7.4 Hz, 3H); $^{13}$C NMR (CDCl$_3$, 75 MHz) δ 175.6, 109.9, 77.4, 76.7, 56.2, 55.1, 51.7, 50.5, 44.2, 33.4, 27.5, 25.0, 24.9, 11.5; IR (neat) 2937 (m), 2102 (s), 1736 (s) cm$^{-1}$; MS (CI, NH$_3$) m/z (rel intensity) 331 [(M+NH$_4$)$^+$, 24], 314 (43), 286 (100), 254 (33), 228 (26), 178 (24), 142 (31); HRMS (CI, NH$_3$) calcd for C$_{14}$H$_{23}$N$_3$O$_5$NH$_4$ [(M+NH$_4$)$^+$] 331.1981, found 331.1995.

Data for (2Rs)-14β (characterization was performed on the mixture): R$_f$=0.38 (3:1 hex/EtOAc); $^1$H NMR (CDCl$_3$, 300 MHz) δ 4.33 (td, J=5.4, 6.7 Hz, 1H), 3.98 (td, J=5.2, 6.7 Hz, 1H), 3.71 (s, 3H), 3.5 (m, 2H), 2.75–2.95 (m, 2H), 2.4–2.6 (m, 1H), 2.05 (m, 0.5H), 1.5–1.9 (m, 3.5H), 1.49 (s, 3H), 1.34 (s, 3H), 0.91 (m, 3H); $^{13}$C NMR (CDCl$_3$, 75 MHz) δ 175.5, 109.7, 76.6, 76.0, 75.9, 56.0, 55.8, 53.2, 52.9, 51.7, 51.6, 51.1, 51.0, 44.0, 33.6, 33.4, 27.3, 25.8, 25.3, 25.2, 11.6, 11.5; IR (neat) 2938 (m), 2103 (s), 1738 (s), 1455 (m), 1372 (m) cm$^{-1}$; MS (CI, NH$_3$) m/z (rel intensity) 331 [(M+NH$_4$)$^+$, 22], 314 (36), 286 (100), 254 (42), 142 (27),; HRMS (CI, NH$_3$) calcd for C$_{14}$H$_{23}$N$_3$O$_5$NH$_4$ [(M+NH$_4$)$^+$]331.1981, found 331.1981.

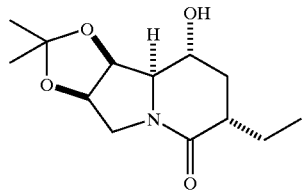

(1S,2R,6S,8R,8aR)-6-Ethyl-8-hydroxy-1,2-O-isopropylidenedioxyindolizidin-5-one (16) Palladium hydroxide on carbon (70 mg) was added to a solution of the epoxide (2S)-10α (520 mg, 1.65 mmol) in MeOH/EtOAc (1:1, 25 mL). The flask was evacuated (aspirator) and purged with hydrogen three times, and the resulting heterogeneous mixture was stirred under a balloon of hydrogen. After 3 h, the hydrogen was evacuated, the mixture was filtered, and the filtrate was concentrated. The residue was redissolved in MeOH (40 mL), sodium methoxide (20 mg, 0.37 mmol) was added, and the mixture was warmed to reflux. Reaction progress was monitored by IR for the disappearance of the ester and lactone carbonyl stretches at 1730 cm$^{-1}$ and appearance of the lactam carbonyl stretch at 1625 cm$^{-1}$. After 36 h, the mixture was cooled to room temperature and concentrated. The residue was dissolved in CH$_2$Cl$_2$/MeOH (20:1, 10 mL), Florisil (500 mg) was added, and the mixture was stirred for 15 min. The suspension was then filtered through Celite and the filtrate was concentrated. Chromatography (50:1 CH$_2$Cl$_2$/MeOH) provided 280 mg (66%) of the lactam 16 as a white crystalline solid. The C(6) stereochemical assignment was based on analysis of $^1$H NMR coupling constants (see Appendix) and the results of the reductive double cyclization of (2R)-12α: (see below). R$_f$=0.30 (20:1 CHCl$_3$/MeOH); [α]$^{23}_D$=+6.7° (c 0.38, CHCl$_3$); mp 162° C.; $^1$H NMR (CDCl$_3$, 360 MHz) δ 4.81 (dd, J=4.6, 6.0 Hz, 1H, H$_1$), 4.75 (ddd, J=1, 5.0, 6.0 Hz, 1H, H$_2$), 4.21 (d, J=13.7 Hz, 1H, H$_{3eq}$), 4.15 (dddd, J=4.0, 4.6, 8.8, 12.8 Hz, 1H, H$_8$), 3.34 (dd, J=4.4, 8.6 Hz, 1H, H$_{8a}$), 3.14 (dd, J=5.1, 13.7 Hz, 1H, H$_{3ax}$), 2.84 (d, J=4.6 Hz, 1H, H$_{8-OH}$), 2.33 (m, 1H, H$_6$), 2.22 (ddd, J=3.9, 6.0, 12.4 Hz, 1H, H$_{7eq}$), 1.99 (m, 1H, H$_9$), 1.64 (app q, J=12.2 Hz, 1H, H$_{7ax}$), 1.55 (m, 1H, H$_9$), 1.42 (s, 3H), 1.34 (s, 3H), 0.93 (t, J=7.5 Hz, 3H, H$_{10}$); $^{13}$C NMR (CDCl$_3$, 90 MHz) δ 170.7, 112.1, 79.8, 77.7, 66.3, 65.1, 50.6, 40.9, 35.1, 26.3, 24.7, 24.5, 11.1; IR (neat) 3310 (m), 2956 (m), 2874 (m), 1609 (s) cm$^{-1}$; MS (EI, 70 eV) m/z (rel intensity) 255 (M$^+$, 22), 240 (22), 227 (100), 180 (21), 142 (13), 113 (35), 110 (21), 84 (50), 68 (11); HRMS (EI, 70 eV) calcd for C$_{13}$H$_{21}$NO$_4$ (M+) 255.1471, found 255.1463.

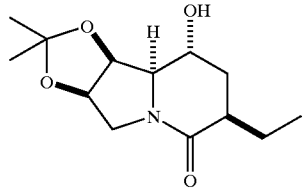

(1S,2R,6R,8R,8aR)-6-Ethyl-8-hydroxy-1,2-O-isopropylidenedioxyindolizidin-5-one (18) The reduction double cyclization of (2R)-12α (515 mg, 1.63 mmol) was carried out according to the procedure described above for (2S)-10α. Chromatography (100:1 CH$_2$Cl$_2$/MeOH) provided 85 mg (20%) of the lactam 16 (see above for characterization) followed by 171 mg (41%) of lactam 18. Formation of 16 indicated that epimerization at C(6) was taking place under the reaction conditions suggesting that the ethyl substituent in 16 most likely occupied an equatorial position and that the ethyl substituent in 18 occupied an axial position. Analysis of the $^1$H NMR coupling constants in 16 and 18 confirmed this assignment (see Appendix). R$_f$ 0.25 (20:1 CHCl$_3$/MeOH); [α]$^{23}_D$=13.2+ (c 0.38, CHCl$_3$); $^1$H NMR (CDCl$_3$, 300 MHz) δ 4.80 (dd, J=4.3, 6.0 Hz, 1H, H$_1$), 4.73 (dd, J=5.0, 6.0 Hz, 1H, H$_2$), 4.27 (ddd, J=4.3, 7.8, 10.5 Hz, 1H, H$_8$), 4.15 (d, J=13.5 Hz, 1H, H$_{3eq}$), 3.30 (dd, J=4.2, 7.6 Hz, 1H, H$_{8a}$), 3.09 (dd, J=4.8, 13.6 Hz, 1H, H$_{ax}$), 3.00 (br s, 1H, H$_{8-OH}$), 2.41 (m, 1H, H$_6$), 2.06 (dt, J=3.9, 13.2 Hz, 1H), 1.90 (m, 2H), 1.55 (m, 1H), 1.40 (s, 3H), 1.33 (s, 3H), 1.01 (t, J=7.4 Hz, 3H); $^{13}$C NMR (CDCl$_3$, 75 MHz) δ 171.8, 111.8, 79.7, 77.6, 66.6, 62.3, 50.5, 41.0, 33.4, 26.4, 25.6, 24.7, 12.2; IR (neat) 3380 (br m), 2936 (m), 2874 (m), 1622 (s) cm$^{-1}$; MS (EI, 70 eV) m/z (rel intensity) 255 (M$^+$, 18), 240 (22), 227 (100), 180 (28), 113 (34), 84 (41); HRMS (EI, 70 eV) calcd for C$_{13}$H$_{21}$NO$_4$ (M$^+$) 255.1471, found 255.1465.

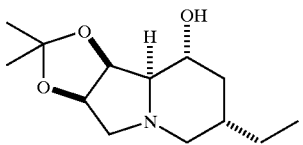

20

(1S,2R,6S,8R,8aR)-6-Ethyl-8-hydroxy-1,2-O-isopropylidenedioxy-indolizidine (20) Reduction of the lactam 267 (265 mg, 1.04 mmol) was carried out with borane-methyl sulfide complex. Chromatography (50:1 CH$_2$Cl$_2$/MeOH) provided 241 mg (96%) of the indolizidine 20 as a white crystalline solid. R$_f$=0.24 (20:1 CHCl$_3$/MeOH); [α]$^{23}_D$=-52.0° (c 1.31, CHCl$_3$); mp 95° C.; $^1$H NMR (CDCl$_3$, 360 MHz) δ 4.69 (dd, J=4.6, 6.2 Hz, 1H, H$_1$), 4.62 (dd, J=4.2, 6.2 Hz, 1H, H$_2$), 3.87 (m, 1H, H$_8$), 3.14 (d, J=10.7 Hz, 1H, H$_{3eq}$), 3.04 (dd, J=3.9, 104 Hz, 1H, H$_{5eq}$), 2.11 (m, 3H, H$_{3ax}$+H$_{7eq}$+H$_{8-OH}$), 1.68 (m, 1H, H$_6$), 1.62 (dd, J=4.4, 9.0 Hz, 1H, H$_{8a}$), 1.54 (d, J=10.5 Hz, 1H, H$_{5ax}$), 1.50 (s, 3H), 1.34 (s, 3H), 1.27 (quint, J=7.4 Hz, 2H, H$_9$), 0.95 (t, J=12.0 Hz, 1H, H$_{7ax}$), 0.90 (t, J=7.4 Hz, 3H, H$_{10}$); $^{13}$C NMR (CDCl$_3$, 90 MHz) δ 111.3, 78.9, 78.5, 73.7, 67.1, 59.7, 57.3, 39.7, 36.9, 26.7, 26.0, 24.8, 11.6; IR (neat) 3250 (br m), 2962 (s), 2803 (m) cm$^{-1}$; MS (EI, 70 eV) m/z (rel intensity) 241 (M$^+$, 56), 166 (100), 156 (29), 141 (59), 124 (40), 98 (32); HRMS (EI, 70 eV) calcd for C$_{13}$H$_{23}$NO$_3$ (M$^+$) 241.1678, found 241.1672.

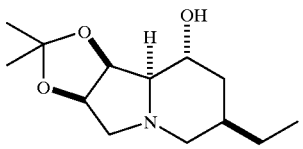

22

(1S,2R,6R,8R,8aR)-6-Ethyl-8-hydroxy-1,2-O-isopropylidenedioxy-indolizidine (22) Reduction of the lactam 18 (150 mg, 0.59 mmol) was carried out with borane-methyl sulfide complex. Chromatography (100:1 to 50:1 CH$_2$Cl$_2$/MeOH gradient) provided 145 mg (100%) of the indolizidine 22 as a colorless oil that crystallized upon standing. R$_f$=0.27 (20:1 CHCl$_3$/MeOH); [α]$^{23}_D$=-27.9° (c 1.17, CHCl$_3$); mp 73–75° C.; $^1$H NMR (CDCl$_3$, 300 MHz) δ 4.69 (dd, J=4.2, 6.3 Hz, 1H, H$_1$), 4.61 (dd, J=4.3, 6.3 Hz, 1H, H$_2$), 3.97 (ddd, J=4.6, 9.0, 11.5 Hz, 1H, H$_8$), 3.06 (d, J=10.6 Hz, 1H, H$_{3eq}$), 2.85 (d, J=10.9 Hz, 1H, H$_{5eq}$), 2.51 (br s, 1H, H$_{8-OH}$) 2.07 (dd, J=4.3, 10.6 Hz, 1H, H$_{3ax}$), 2.00 (m, 2H, H$_{5ax}$+H$_{7eq}$+), 1.65 (m, 1H, H$_6$), 1.5–1.6 (m, 2H, H$_{8a}$+H$_9$), 1.49 (s, 3H), 1.3–1.5 (m, 2H, H$_9$+H$_{7ax}$), 1.34 (s, 3H), 0.89 (t, J=7.3 Hz, 3H, H$_{10}$); $^{13}$C NMR (CDCl$_3$, 75 MHz) δ 111.5, 79.5, 78.5, 74.3, 64.0, 60.5, 54.7, 37.1, 36.8, 26.3, 25.6, 25.4, 12.7; IR (neat) 3420 (br m), 2934 (s), 2784 (m), 1462 (m) cm$^{-1}$; MS (EI, 70 eV) m/z (rel intensity) 241 (M$^+$, 47), 166 (100), 156 (36), 141 (65), 124 (52), 98 (39), 55 (44); HRMS (EI, 70 eV) calcd for C$_{13}$H$_{23}$NO$_3$ (M$^+$) 241.1678, found 241.1688.

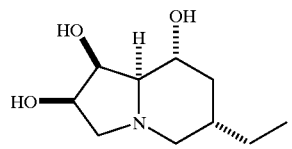

24

(1S,2R,6S,8R,8aR)-6-Ethyl-1,2,8-trihydroxyindolizidine [(6S)-6-Ethyl-swainsonine] (24) The acetonide 20 (200 mg, 0.83 mmol) was hydrolyzed with 6 N HCl in THF. Chromatography (50:10:1 CH$_2$Cl$_2$/MeOH/Aq. NH$_4$OH) provided 166 mg (99%) of the title compound as a white solid that was recrystallized from n-butanol. R$_f$=0.42 (2:1 CHCl$_3$/MeOH); [α]$^{23}_D$=-42.3° (c 1.17, CHCl$_3$); mp 134° C.; $^1$H NMR (CD$_3$OD, 360 MHz) δ 4.19 (m, 2H), 3.79 (td, J=4.5, 10.5 Hz, 1H), 2.9 (m, 2H), 2.38 (dd, J=7.2, 10.3 Hz, 1H), 2.30 (m, 1H), 1.67 (dd, J=3.2, 8.7 Hz, 1H), 1.5 (m, 2H), 1.25 (m, 2H), 0.90 (t, J=7.4 Hz, 1H); $^{13}$C NMR (CD$_3$OD, 90 MHz) δ 75.3, 70.6, 70.2, 66.9, 63.1, 59.0, 41.0, 37.7, 28.0, 12.0; IR (neat) 3375 (br s), 2944 (s), 2793 (m), 1614 (w) cm$^{-1}$; MS (CI, CH$_4$ and NH$_3$) m/z (rel intensity) 202 [(M+H)$^+$, 91), 184 (100), 141 (10); HRMS (CI, CH$_4$ and NH$_3$) calcd for C$_{10}$H$_{19}$NO$_3$H [(M+H)$^+$] 202.1443, found 202.1444. Anal. Calcd for C$_{10}$H$_{19}$NO$_3$: C, 59.68; H, 9.52; N, 6.96. Found C, 59.69; H, 9.67; N, 6.96.

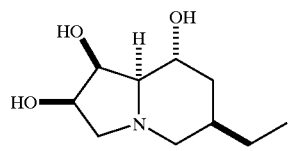

26

(1S,2R,6R,8R,8aR)-6-Ethyl-1,2,8-trihydroxyindolizidine [(6R)-6-Ethyl-swainsonine] (26) The acetonide 22 (105 mg, 0.44 mmol) was hydrolyzed with 6 N HCl in THF. Chromatography (50:10:1 CH$_2$Cl$_2$/MeOH/Aq. NH$_4$OH) provided 84 mg (96%) of the title compound as a colorless oil. R$_f$=0.55 (2:1 CHCl$_3$/MeOH); [α]$^{23}_D$=39.0° (c 1.17, CHCl$_3$); $^1$H NMR (D$_2$O, 300 MHz) δ 4.34 (td, J=2.5, 7.7 Hz, 1H), 4.23 (dd J=3.6, 5.9 Hz, 1H), 3.96 (ddd, J=4.5, 9.6, 11.1 Hz, 1H), 2.88 (m, 2H), 2.51 (dd, J=8.0, 11.0 Hz, 1H), 2.09 (dd, J=3.8, 11.5 Hz, 1H), 2.02 (m, 1H), 1.86 (dd, J=3.5, 9.4 Hz, 1H), 1.75 (m, 1H), 1.35–1.50 (m, 3H), 0.90 (t, J=7.4 Hz, 3H); $^{13}$C NMR (CD$_3$OD, 90 MHz) δ 76.0, 71.4, 70.4, 64.2, 63.5, 56.7, 38.2, 38.0, 26.4, 13.1; IR (neat) 3555 (br s), 2929 (s), 2784 (m), 1460 (m) cm$^{-1}$; MS (CI, CH$_4$ and NH$_3$) m/z (rel intensity) 202 [(M+H)$^+$, 70), 184 (100), 166 (10), 141 (11); HRMS (CI, CH$_4$ and NH$_3$) calcd for C$_{10}$H$_{19}$NO$_3$H [(M+H)$^+$] 202.1443, found 202.1438.

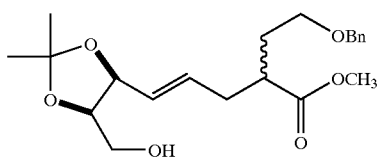

Methyl (E)-(2S,6S,7R)-2-[2-(Benzyloxy)ethyl]-8-hydroxy-6,7-O-isopropylidenedioxy-4-octenoate and Methyl (E)-(2R,6S,7R)-2-[2-(Benzyloxy)ethyl]-8-hydroyx-6,7-O-isopropylidenedioxy-4-octenoate (7a/b) 4-Benzyloxy-1,1,1-trimethoxybutane (10.1 g, 60% pure by GC analysis, 24 mmol) and propionic acid (150 mg, 2.0 mmol) were added to a solution of the allylic alcohol 5 (3.54 g, 11.7 mmol) in toluene (40 mL). The flask was fitted with a distillation head and was warmed to reflux, distilling off methanol as it formed. After 24 h, the mixture was cooled to room temperature and concentrated. The crude residue was dissolved in THF (40 mL), cooled to 0° C., and tetra-n-butylammonium fluoride (5.9 mL of a 1 M soln. in THF, 5.9 mmol) was added in a dropwise fashion. After 2 h, the solution was diluted with ether (100 mL) and washed with brine (2×50 mL). The aqueous layers wer back-extracted with EtOAc (100 mL), then the combined organic layers were dried (MgSO$_4$), and concentrated. Chromatography (6:1 to 2:1 hex/EtOAc gradient) provided 2.97 g (67%) of an inseparable mixture (1:1) of diastereomeric hydroxy esters 7a/b as a pale yellow oil. $R_f$=0.19 (2:1 hex/EtOAc); $^1$H NMR (CDCl$_3$, 360 MHz) δ 7.2–7.4 (m, 5H), 5.73 (m, 1H), 5.52 (dd, J=8.0, 15.4 Hz, 1H), 4.60 (m, 1H), 4.48 (s, 2H), 4.20 (m, 1H), 3.62 (m, 3H), 3.4–3.6 (m, 4H), 2.70 (m, 1H), 2.2–2.5 (m, 3H), 1.96 (m, 1H), 1.78 (m, 1H), 1.49 (s, 3H), 1.38 (s, 3H); $^{13}$C NMR (CDCl$_3$, 90 MHz) δ 175.3, 138.4, 131.7, 131.5, 128.2, 127.5, 127.4, 108.5, 78.5, 78.0, 77.9, 73.0, 68.0, 61.9, 51.3, 42.4, 42.3, 34.8, 34.7, 31.9, 31.7, 27.8, 25.3; IR (neat) 3490 (br m), 2934 (m), 2868 (m), 1732 (s), 1441 (m) cm$^{-1}$; MS (CI, CH$_4$ and NH$_3$) m/z (rel intensity) 321 (12), 213 (28), 195 (48), 107 (28), 91 (100); HRMS (CI, CH$_4$ and NH$_3$) calcd for C$_{21}$H$_{30}$O$_6$C$_2$H$_5$ [(M+C$_2$H$_5$)$^+$] 407.2434, found 407.2449. Anal. Calcd for C$_{21}$H$_{30}$O$_6$: C, 66.65; H, 7.99. Found C, 66.33; H, 8.29.

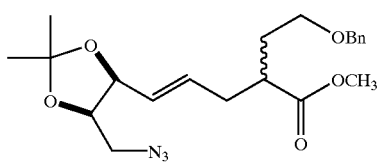

Methyl (E)-(2S,6S,7R)-8-Azido-2-[2-(benzyloxy)ethyl]-6,7-O-isopropylidenedioxy-4-octenoate and Methyl (E)-(2R,6S,7R)-8-Azido-2-[2-(benzyloxy)ethyl]-6,7-O-isopropylidenedioxy-4-octenoate (9a/b). Hydrazoic acid (12.3 mL of a 1.2 M solution in benzene, 14.8 mmol)$^{26}$ was added to a solution of the alcohol 7a/b (2.81 g, 7.42 mmol) and triphenylphosphine (2.91 g, 11.1 mmol) in benzene (29 mL). The mixture was cooled to 5° C. and diethyl azodicarboxylate (1.82 mL, 11.1 mmol) was added in a dropwise fashion. The solution was then allowed to warm to room temperature. After 1.5 h, TLC indicated that starting material was still present. More hydrazoic acid solution (6.2 mL, 7.5 mmol), triphenylphosphine (0.97 g, 3.71 mmol), and DEAD (0.61 mL, 3.71 mmol) were added and the mixture was allowed to stir at room temperature for another 1 h. The mixture was then poured into hexane (100 mL), resulting in the formation of a white precipitate. The mixture was filtered and the filtrate was concentrated. Chromatography (12:1 to 6:1 hexane/EtOAc gradient) provided 1.97 g (66%) of an inseparable mixture (1:1) of diastereomeric azides 9a/b as a colorless oil. $R_f$=0.31 (5:1 hex/EtOAc); $^1$H NMR (CDCl$_3$, 300 MHz) δ 7.2–7.4 (m, 5H), 5.73 (m, 1H), 5.46 (m, 1H), 4.59 (t, J=6.8 Hz, 1H), 4.47 (s, 2H), 4.23 (ddd, J=4.3, 6.7, 7.5 Hz, 1H), 3.62 (d, J=2.5 Hz, 3H), 3.46 (m, 2H), 3.24 (dd, J=7.6, 12.8 Hz, 1H), 3.13 (ddd, J=1.4, 4.3, 12.8 Hz, 1H), 2.68 (m, 1H), 2.39 (m, 1H), 2.30 (m, 1H), 1.95 (m, 1H), 1.77 (m, 1H), 1.51 (s, 3H), 1.37 (s, 3H); $^{13}$C NMR (CDCl$_3$, 75 MHz) δ 175.3, 138.2, 132.5, 132.3, 128.2, 127.5, 127.5, 126.8, 126.7 109.0, 77.8, 77.8, 76.9, 73.0, 67.9, 51.5, 42.2, 42.1, 34.9, 34.8, 31.9, 31.7, 27.8, 25.3; IR (neat) 2988 (w), 2936 (w), 2862 (w), 2101 (s), 1732 (s) cm$^{-1}$; MS (CI, NH$_3$) m/z (rel intensity) 421 (24), 376 (100), 318 (35), 106 (29); HRMS (CI, NH$_3$) calcd for C$_{21}$H$_{29}$N$_3$O$_5$NH$_4$ [(M+NH$_4$)$^+$] 421.2451, found 421.2428. Anal. Calcd for C$_{21}$H$_{29}$N$_3$O$_5$: C, 62.51; H, 7.24; N, 10.41. Found: C, 62.51; H, 7.23, N, 10.43.

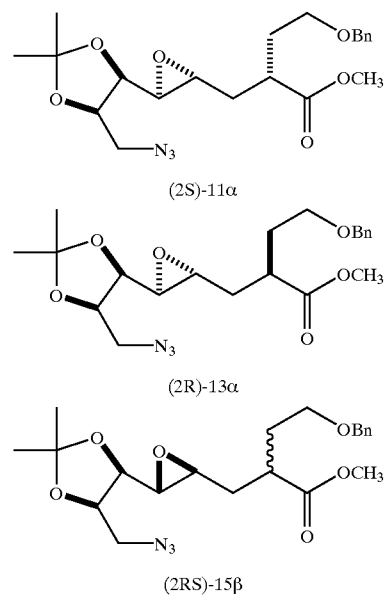

Methyl (2S,4R,5S,6R,7R)-8-Azido-2-[2-(benzyloxy)ethyl]-4,5-epoxy-6,7-O-isopropylidenedioxyoctanoate [(2S)-11α], Methyl (2R,4R,5S,6R,7R)-8-Azido-2-[2-(benzyloxy)ethyl]-4,5-epoxy-6,7-O-isopropylidenedioxyoctanoate [(2R)-13α], Methyl (2S,4S,5R,6R,7R)-8-Azido-2-[2-(benzyloxy)ethyl]-4,5-epoxy-6,7-O-isopropylidenedioxyoctanoate [(2S)-15β], and Methyl (2R,4S,5R,6R,7R)-8-Azido-2-[2-(benzyloxy)ethyl]-4,5-epoxy-6.7-O-isopropylidenedioxyoctanoate [(2R)-15β]. m-Chloroperbenzoic acid (2.30 g, technical grade, 1.84 g pure, 12.3 mmol) was added to a cooled (0° C.) solution of the azide 9a/b (1.72 g, 4.25 mmol) in CH$_2$Cl$_2$ (25 mL). After 24 h, the mixture was diluted with ether (100 mL) and washed with 1 M NaOH (2×50 mL). The aqueous layers were backed-extracted with ether (2×50 mL) and the combined organic layers were washed with saturated NaHCO$_3$ (100 mL) and brine (50 mL), then dried (MgSO$_4$), filtered, and concentrated. Chromatography (15:1 to 8:1 hex/EtOAc gradient—2 passes) provided 0.50 g (28%) of the epoxide isomer (2S)-11α as a pale yellow oil, followed by 0.50 g (28%) of the epoxide isomer (2R)-13α as a pale yellow oil, followed by 0.39 g (22%) of a mixture (1:1) of diastereomeric epoxide (2RS)-15βa/b.

Data for (2S)-11α: $R_f$=0.45 (6:1 hex/EtOAc—3 elutions); $[\alpha]^{23}_D$=+39.8 (c 1.25, CHCl$_3$); $^1$H NMR (CDCl$_3$, 300 MHz) δ 7.2–7.4 (m, 5H), 4.47 (s, 2H), 4.33 (td, J=4.1, 6.8 Hz, 1H), 3.68 (dd, J=6.5, 7.9 Hz, 1H), 3.64 (s, 3H), 3.4–3.6 (m, 4H), 2.88 (ddd, J=1.9, 4.9, 6.6 Hz, 1H), 2.79 (m, 2H), 2.01 (m, 2H), 1.82 (m, 1H), 1.67 (ddd, J=5.0, 6.6, 14.2 Hz, 1H), 1.51 (s, 3H), 1.34 (s, 3H); $^{13}$C NMR (CDCl$_3$, 75 MHz) δ 175.2, 138.2, 128.2, 127.5, 127.4, 109.8, 77.3, 76.6, 73.0, 67.7, 56.3, 55.2, 51.7, 50.5, 39.8, 34.0, 32.4, 27.6, 25.0; IR (neat) 2988 (w), 2936 (w), 2863 (w), 2102 (s), 1732 (s) cm$^{-1}$; MS (CI, NH$_3$) m/z (rel intensity) 437 [(M+NH$_4$)$^+$, 21], 392 (100), 360 (81), 224 (49), 142 (54), 131 (27), 108 (35); HRMS (CI, NH$_3$) calcd for C$_{21}$H$_{29}$N$_3$O$_6$NH$_4$ [(M+NH$_4$)$^+$] 437.2400, found 437.2379. Anal. Calcd for C$_{21}$H$_{29}$N$_3$O$_6$: C, 60.31; H, 6.97; N, 10.02. Found: C, 60.11; H, 6.98, N, 9.76.

Data for (2R)-13α: $R_f$=0.38 (6:1 hex/EtOAc—3 elutions); $[\alpha]^{23}_D$=+50.0° (c 0.80, CHCl$_3$); $^1$H NMR (CDCl$_3$, 360 MHz) δ 7.2–7.4 (m, 5H), 4.47 (s, 2H), 4.35 (dt, J=4.0, 7.0 Hz, 1H), 3.70 (dd, J=6.5, 7.8 Hz, 1H), 3.65 (s, 3H), 3.44–3.63 (m, 4H), 2.93 (ddd, J=1.9, 4.6, 6.9 Hz, 1H), 2.79 (m, 2H), 2.1 (m, 1H), 1.75–1.95 (m, 3H), 1.51 (s, 3H), 1.35 (s, 3H); $^{13}$C NMR (CDCl$_3$, 90 MHz) δ 175.5, 138.2, 128.3, 127.6, 127.6, 109.9, 77.3, 76.6, 73.0, 67.7, 56.1, 54.9, 51.8, 50.5, 39.9, 33.8, 31.7, 27.5, 25.0; IR (neat) 2988 (w), 2934 (w), 2862 (w), 2102 (s), 1732 (s) cm$^{-1}$; MS (CI, NH$_3$) m/z (rel intensity) 437 [(M+NH$_4$)$^+$, 25], 420 (24), 392 (100), 360 (17), 142 (21); HRMS (CI, NH$_3$) calcd for C$_{21}$H$_{29}$N$_3$O$_6$NH$_4$ [(M+NH$_4$)$^+$] 437.2400, found 437.2410. Anal. Calcd for C$_{21}$H$_{29}$N$_3$O$_6$: C, 60.31; H, 6.97; N, 10.02. Found: C, 60.06; H, 6.91, N, 9.77.

Data for (2RS)-15β: $R_f$=0.30 (6:1 hex/EtOAc—3 elutions); $^1$H NMR (CDCl$_3$, 360 MHz) δ 7.2–7.4 (m, 5H), 4.47 (s, 2H), 4.31 (dd, J=6.7, 12.0 Hz, 1H), 3.96 (ddd, J=4.9, 6.7, 11.1 Hz, 1H), 3.65 (d, J=3.7 Hz, 3H), 3.40–3.55 (m, 3H), 2.91 (m, 1H), 2.80 (m, 2H), 2.02 (m, 1.5H), 1.85 (m, 2H), 1.61 (m, 0.5H), 1.51 (s, 3H), 1.35 (s, 3H); $^{13}$C NMR (CDCl$_3$, 90 MHz) δ 175.5, 138.2, 128.3, 127.7, 127.6, 109.8, 76.9, 76.4, 75.9, 75.8, 73.0, 67.6, 55.9, 55.7, 52.9, 52.7, 51.8, 51.7, 51.0, 50.9, 39.8, 39.7, 33.9, 33.8, 32.4, 31.8, 27.2, 27.1, 25.2; IR (neat) 2986 (w), 2862 (w), 2102 (s), 1736 (s) cm$^{-1}$; MS (CI, NH$_3$) m/z (rel intensity_ 437 [(M+NH$_4$)$^+$, 24], 420 (22), 392 (100); HRMS (CI, NH$_3$) calcd for C$_{21}$H$_{29}$N$_3$O$_6$NH$_4$ [(M+NH$_4$)$^+$] 437.2400, found 437.2407. Anal. Calcd for C$_{21}$H$_{29}$N$_3$O$_6$: C, 60.31; H, 6.97; N, 10.02. Found: C, 60.29; H, 6.98, N, 9.97.

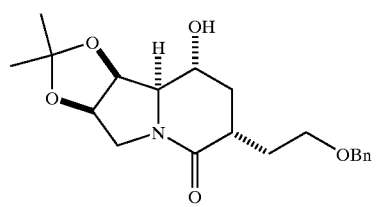

17

(1S,2R,6S,8R,8aR)-6-[2-(Benzyloxy)ethyl]-8-hydroxy-1,2-O-isopropylidenedi oxyindolizidin-5-one (17). The reductive double cyclization of (2S)-11α (300 mg, 0.72 mmol) was carried out as above. Chromatography (100:1 to 50:1 CH$_2$Cl$_2$/MeOH) provided 204 mg (79%) of the lactam 17 as an oil. Data for 17: $R_f$=0.15 (50:1 CHCl$_3$/MeOH); $[\alpha]^{23}_D$= 4.1° (c 1.03, CHCl$_3$); $^1$H NMR (CDCl$_3$, 360 MHz) δ 7.2–7.4 (m, 5H), 4.77 (dd, J=4.6, 6.0 Hz, 1H), 4.70 (t, J=5.2 Hz, 1H), 4.49 (ABq, J=11.9 Hz, Δv=17.5 Hz, 2H), 4.17 (d, J=13.6 Hz, 1H), 4.13 (m, 1H), 3.60 (m, 2H), 3.28 (dd, J=4.5, 8.8 Hz, 1H), 3.07 (dd, J=5.0, 13.6 Hz, 1H), 2.74 (br s, 1H), 2.54 (m, 1H), 2.35 (m, 1H), 2.22 (ddd, J=3.9, 5.9, 12.5 Hz, 1H), 1.6–1.8 (m, 2H), 1.41 (s, 3H), 1.32 (s, 3H); $^{13}$C NMR (CDCl$_3$, 90 MHz) δ 170.7, 138.4, 128.3, 127.6, 127.5, 112.0, 79.7, 77.6, 72.7, 67.9, 66.3, 64.9, 50.6, 37.0, 35.8, 31.3, 26.3, 24.6; IR (neat) 3330 (br w), 2934 (w), 2863 (w), 1621 (s), 1082 (s) cm$^{-1}$; MS (CI, NH$_3$) m/z (rel intensity) 362 [(M+H)$^+$, 100]. 270 (18), 227 (23); HRMS (CI, CH$_4$ and NH$_3$) calcd for C$_{20}$H$_{27}$NO$_5$H [(M+H)$^+$] 362.1967, found 362.1953.

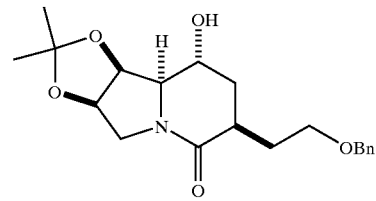

23

(1S,2R,6R,8R,8aR)-6-[2-(Benzyloxy)ethyl]-8-hydroxy-1,2-O-isopropylidenedi oxyindolizidin-5-one (23). The reductive double cyclization of (2R)-13α (405 mg, 0.97 mmol) was carried out as above. Chromatography (100:1 to 50:1 CH$_2$Cl$_2$/MeOH) provided 230 mg (66%) of the lactam 17 (see above for characterization) followed by 46 mg (13%) of lactam 19 as an oil. Epimerization at C(6) similar to that encountered in the C(6)-ethyl substituted series (see above) suggested that the benzyloxyethyl substituent in 17 most likely occupies an equatorial position and that the benzyloxyethyl substituent in 19 occupies an axial position. Data for 19: $R_f$=0.10 (50:1 CHCl$_3$/MeOH); $[\alpha]^{23}_D$=−11.9° (c 0.84, CHCl$_3$); $^1$H NMR (CDCl$_3$, 360 MHz) δ 7.2–7.4 (m, 5H), 4.77 (dd, J=4.4, 6.0 Hz, 1H), 4.72 (dd, J=4.5, 6.0 Hz, 1H), 4.51 (ABq, J=11.9 Hz, Δv=20.8 Hz, 2H), 4.29 (ddd, J=4.3, 7.5, 10.3 Hz, 1H), 4.16 (d, J=13.6 Hz, 1H), 3.64 (t, J=6.5 Hz, 2H), 3.29 (dd, J=4.3, 7.5 Hz, 1H), 3.08 (dd, J=4.9, 13.6 Hz, 1H), 2.66 (m, 1H), 2.2 (m, 1H), 2.04 (dt, J=4.3, 13.2 Hz, 1H), 1.95 (ddd, J=6.0, 10.1, 13.2 Hz, 1H), 1.74 (ddt, J=6.2, 8.1, 14.1 Hz, 1H), 1.39 (s, 3H), 1.32 (s, 3H); $^{13}$C NMR (CDCl$_3$, 90 MHz) δ 171.6, 138.4, 128.4, 127.7, 127.5, 111.9, 79.7, 77.6, 72.9, 68.5, 66.4, 62.6, 50.4, 36.6, 34.4, 32.5, 26.4, 24.6; IR (neat) 3390 (br w), 2934 (w), 2861 (w), 1622 (s), 1097 (s) cm$^{-1}$; MS (CI, CH$_4$) m/z (rel intensity) 362 [(M+H)$^+$, 69], 270 (100), 254 (57), 227 (92), 91 (74); HRMS (CI, CH$_4$) calcd for C$_{20}$H$_{27}$NO$_5$H [(M+H)$^+$] 362.1967, found 362.1960.

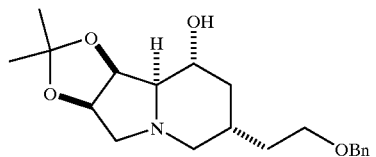

272

(1S,2R,6S,8R,8aR)-6-[2-(Benzyloxy)ethyl]-8-hydroxy-1,2-O-isopropylidenedi oxyindolizidine (21). Reduction of the lactam 17 (120 mg, 0.33 mmol) was carried out with borane-methyl sulfide complex. Chromatography (25:25:1 hex/EtOAc/EtOH) provided 108 mg (94%) of the indolizidine 17. $R_f$=0.20 (1:1 hex/EtOAc); $[\alpha]^{23}_D$=31.4° (c 0.87, CHCl$_3$); $^1$H NMR (CDCl$_3$, 300 MHz) δ 7.2–7.4 (m, 5H), 4.69 (dd, J=4.5, 6.2 Hz, 1H), 4.61 (dd, J=4.1, 6.3 Hz, 1H), 4.44 (s, 2H), 3.86 (m, 1H), 3.49 (t, J=6.6 Hz, 2H), 3.12 (d, J=10.7 Hz, 1H), 3.01 (dd, J=3.9, 10.6 Hz, 1H), 2.11 (m, 3H), 1.92 (m, 1H), 1.58 (m, 4H), 1.50 (s, 3H), 1.33 (s, 3H), 0.98 (dt, J=11.3, 12.0 Hz, 1H); $^{13}$C NMR (CDCl$_3$, 90 MHz) δ 138.4, 128.3, 127.6, 127.5, 111.4, 78.9, 78.5, 73.5, 72.9, 68.2, 66.9, 59.6, 57.5, 39.9, 33.8, 32.6, 26.0, 24.8; IR (neat) 3450 (br m), 2931 (w), 2855 (m), 2786 (m), 1453 (m), 1369 (m) cm$^{-1}$; MS (CI, CH$_4$ and NH$_3$) m/z (rel intensity) 348 [(M+H)$^+$, 100], 270 (13), 256 (11); HRMS (CI, CH$_4$ and NH$_3$) calcd for C$_{20}$H$_{29}$NO$_4$H [(M+H)$^+$] 348.2175, found 348.2168. Anal. Calcd for C$_{20}$H$_{29}$NO$_4$: C, 69.14; H, 8.41; N, 4.03. Found, C, 68.97; H, 8.61; N, 4.02.

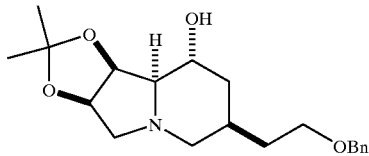

23

(1S,2R,6R,8R,8aR)-6-[2-(Benzyloxy)ethyl]-8-hydroxy-1,2-O-isopropylidenedi oxyindolizidine (23). Reduction of the lactam 19 (40 mg, 0.11 mmol) was carried out with borane-methyl sulfide complex. Chromatography (25:25:1 hex/EtOAc/EtOH) provided 36 mg (95%) of the indolizidine 19 as an oil. R$_f$=0.26 (1:1 hex/EtOAc); [α]$^{23}_D$=−14.2° (c 0.90, CHCl$_3$); $^1$H NMR (CDCl$_3$, 300 MHz) δ 7.2–7.4 (m, 5H), 4.68 (dd, J=4.3, 6.3 Hz, 1H), 4.60 (dd, J=4.2, 6.3 Hz, 1H), 4.49 (s, 2H), 3.98 (m, 1H), 3.50 (t, J=6.3 Hz, 2H), 3.03 (d, J=10.6 Hz, 1H), 2.81 (d, J=10.5 Hz, 1H), 1.85–2.15 (m, 6H), 1.74 (m, 1H), 1.58 (m, 1H), 1.47 (s, 3H), 1.40 (td, J=4.8, 12.5 Hz, 1H), 1.32 (s, 3H); $^{13}$C NMR (CDCl$_3$, 90 MHz) δ 138.6, 128.3, 127.6, 127.5, 111.6, 79.4, 78.4, 74.1, 72.8, 68.7, 64.1, 60.3, 54.8, 37.3, 32.3, 31.3, 26.2, 25.4; IR (neat) 3445 (br m), 2934 (s), 2858 (m), 2784 (m), 1378 (m) cm$^{-1}$; MS (CI, CH$_4$) m/z (rel intensity) 348 [(M+H)$^+$, 100], 256 (56), 240 (37), 107 (26), 91 (38); HRMS (CI, CH$_4$) calcd for C$_{20}$H$_{29}$NO$_4$H [(M+H)$^+$] 348.2175, found 348.2176.

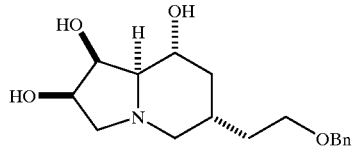

25

(1S,2R,6S,8R,8aR)-6-[2-(Benzyloxy)ethyl]-1,2,8-trihydroxyindolizidine [(6S)-6-(2-Benzyloxyethyl) swainsonine] (25). The acetonide of the indolizidine 21 (44 mg, 0.13 mmol) was hydrolyzed with 6 N HCl in THF. Chromatography (80:20:1 to 50:25:1 EtOAc/EtOH/Aq. NH$_4$OH) provided 38 mg (97%) of the title compound (25) as a colorless oil. R$_f$=0.26 (2:1 EtOAc/EtOH); [α]$^{23}_D$=−42.5° (c 0.89, MeOH); $^1$H NMR (CD$_3$OD, 300 MHz) δ 7.2–7.4 (m, 5H), 4.49 (s, 2H), 4.22 (ddd, J=2.0, 6.2, 13.3 Hz, 1H), 4.17 (dd, J=3.6, 6.1 Hz, 1H), 3.82 (ddd, J=4.6, 9.3, 11.1 Hz, 1H), 3.53 (t, J=6.4 Hz, 2H), 2.97 (dd, J=3.2, 11.1 Hz, 1H), 2.90 (dd, J=1.9, 10.4 Hz, 1H), 2.41 (dd, J=7.0, 10.4 Hz, 1H), 2.27 (m, 1H), 1.87 (m, 1H), 1.71 (dd, J=3.5, 9.2 Hz, 1H), 1.58 (m, 3H), 0.93 (dt, J=11.3, 12.2 Hz, 1H); $^{13}$C NMR (CD$_3$OD, 90 MHz) δ 140.0, 129.5, 129.0, 128.8, 75.2, 74.1, 70.6, 70.2, 69.2, 66.8, 63.0, 59.1, 41.3, 35.1, 33.3; IR (neat) 3780 (br s), 2941 (s), 2853 (m) cm$^{-1}$; MS (CI, CH$_4$ and NH$_3$) m/z (rel intensity) 306 [(M−H)$^+$, 3], 302 (3), 216 (100), 91 (40); HRMS (CI, CH$_4$ and NH$_3$) calcd for C$_{17}$H$_{24}$NO$_4$ [(M−H)$^+$] 306.1705, found 306.1717.

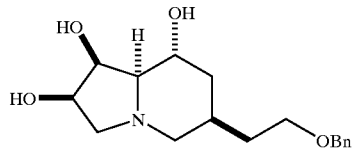

27

(1S,2R,6R,8R,8aR)-6-[2-(Benzyloxy)ethyl]-1,2,8-trihydroxyindolizidine [(6R)-6-(2-Benzyloxyethyl) swainsonine] (27). the acetonide of the indolizidine 23 (20 mg, 0.058 mmol) was hydrolyzed with 6 N HCl in THF. Chromatography (80:20:1 to 50:25:1 EtOAc/EtOH/Aq. NH$_4$OH) provided 13 mg (73%) of the title compound (27) as a colorless oil. R$_f$32 0.23 (10:1 CHCl$_3$/MeOH); [α]$^{23}_D$=−24.1° (c 0.56, MeOH); $^1$H NMR (CD$_3$OD, 300 MHz) δ 7.2–7.4 (m, 5H), 4.49 (s, 2H), 4.16 (m, 2H), 3.94 (ddd, J=4.6, 9.1 11.6 Hz, 1H), 3.54 (t, J=6.1 Hz, 2H), 2.86 (dd, J=1.7, 10.6 Hz, 1H), 2.81 (m, 1H), 2.34 (dd, J=6.8, 10.2 Hz, 1H), 1.91–2.01 (m, 3H), 1.87 (m, 1H), 1.75 (m, 1H), 1.64 (dd, J=3.4, 9.1 Hz, 1H), 1.35 (m, 1H); $^{13}$C NMR (CD$_3$OD, 90 MHz) δ 140.0, 129.4, 128.9, 128.6, 75.9, 74.0, 71.6, 70.5, 70.2, 64.4, 63.3, 57.0, 38.6, 33.6, 33.1; IR (neat) 3355 (br m), 2930 (m), 2850 (m), 2790 (m), 1097 (s) cm$^{-1}$; MS (CI, NH$_3$) m/z (rel intensity) 308 [(M+H)$^+$, 100], 270 (63), 254 (17), 218 (16); HRMS (CI, NH$_3$) calcd for C$_{17}$H$_{25}$NO$_4$H [(M+H)$^+$] 308.1861, found 308.1873.

PART II: Synthesis of 7-Substituted Swainsonine Analogs by Incorporation of the C(7) Substituent Using a Claisen Rearrangement.

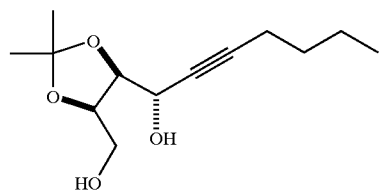

35

(2R,3S,4S)-1,4-Dihydroxy-2,3-O-isopropylidenedioxy-5-decyne (35). Addition of hexynylmagnesium bromide to 2,3-O-isopropylidene-D-erythrose has been reported by Mekki et al.,[18] 2,3-O-isopropylidene-D-erythrose was prepared via the diisobutylaluminum hydride reduction of 2,3-O-isopropylidene-D-erythronolactone. Hexynylmagnesium chloride was prepared by adding isopropylmagnesium chloride (13.3 mL of a 2 M soln. in ether, 26.6 mmol) to a cooled (0° C.) solution of 1-hexyne (3.0 mL, 2.15 g, 26.6 mmol) in THF (35 mL), and then allowing the solution to warm to room temperature. The hexynylmagnesium chloride solution was transferred via cannula into a cooled (−78° C.) solution of 2,3-O-isopropylidene-D-erythrose (1.70 g, 10.6 mmol). The resulting mixture was stirred for 30 min at −78° C., and was then allowed to warm slowly to 0° C. After 6 h, the reaction was quenched by addition of saturated aqueous NH$_4$Cl (100 mL). The mixture was extracted with ether (2×100 mL), the combined organic phases were washed with water (50 mL) and brine (50 mL), and then dried (MgSO$_4$), and concentrated to provide 2.47 g of the diol 35 that was used without further purification. The stereochemistry of 35 was assigned based on the results of Mekki et al.[18] [A small sample was purified by chromatography (3:1 to 2:1 hex/EtOAc gradient) to obtain an analytically pure sample. R$_f$=0.20 (2:1 hex/EtOAc): [α]$^{23}_D$−10.6° (c 0.85, CHCl$_3$); $^1$H NMR (CDCl$_3$, 360 MHz) δ 4.60 (br s, 1H), 4.32 (dt, J=4.6, 6.0 Hz, 1H), 4.21 (t, J=6.4 Hz, 1H), 3.94 (m, 2H), 3.76 (br s, 1H), 3.19 (br s, 1H), 2.23 (td, J=2.0, 7.0 Hz, 2H), 1.35–1.55 (m, 4H), 1.49 (s, 3H), 1.38 (s, 3H), 0.91 (t, J=7.3 Hz, 3H); $^{13}$C NMR (CDCl$_3$, 90 MHz) δ 108.6, 87.2, 79.2, 78.0, 77.1, 61.4, 60.4, 30.5, 27.3, 25.1, 21.9, 18.4, 13.5; IR (neat) 3380 (br, s), 1934 (s), 1380 (s) cm$^{-1}$; MS (CI, CH$_4$ and NH$_3$) m/z (rel intensity) 243 [(M+H)$^+$, 6], 225 (15), 185 (31), 167 (100), 125 (76); HRMS (CI, CH$_4$ and NH$_3$) calcd for C$_{13}$H$_{22}$O$_4$H [(M+H)$^+$] 243.1496, found 243.1596; Anal. Calcd for C$_{13}$H$_{22}$O$_4$: C, 64.44; H, 9.15. Found: C, 64.12; H, 9.12.]

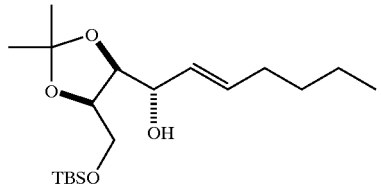

37

(E)-(2R,3S,4S)-1-tert-Butyldimethylsilyloxy-4-hydroxy-2,3-O-isopropylidene dioxy-5-decene (37). Sodium bis(2-methoxyethoxy)aluminum hydride (Red-Al) (6.0 mL of a 70% soln. in toluene, 21.5 mmol) was added in a dropwise fashion to a cooled (0° C.) solution of the diol 35 (1.30 g, 5.36 mmol) in ether (22 mL). The solution was allowed to warm to room temperature. After 2 h, the reaction was quenched by the slow droqwise addition of 1 N H$_2$SO$_4$ until no more H$_2$ evolution was observed. The mixture was then poured into ether (100 mL) and washed with water (3×50 mL). The aqueous layers were back-extracted with ether (100 mL). The combined organic layers were washed with brine (50 mL), dried (MgSO$_4$), and concentrated to give 1.25 g of of a pale yellow oil that was used without further purification [R$_f$=0.32 (2:1 hex/EtOAc)]. The crude oil was dissolved in THF/DMF (2:1, 30 mL) and the solution was cooled to 0° C. tert-Butyldimethylsilyl chloride (0.97 g, 6.43 mmol) and imidazole (0.95 g, 13.9 mmol) were added, and the solution was stirred at 0° C. for 2 h. The mixture was then diluted with ether (100 mL), and washed with 1 M HCl (2×50 mL), sat. NaHCO$_3$ (50 mL), and brine (50 mL). The organic layer was dried (MgSO$_4$) and concentrated. Chromatography (15:1 hex/EtOAc) provided 1.70 g (75% from the lactone) of the (E)-allylic alcohol 37 as a colorless oil. R$_f$=0.20 (15:1 hex/EtOAc); [α]$^{23}$$_D$=–19.3+ (c 0.90, CHCl$_3$); $^1$H NMR (CDCl$_3$, 300 MHz) δ 5.83 (dt, J=6.7, 15.4 Hz, 1H), 5.59 (dd, J=5.6, 15.4 Hz, 1H), 4.23 (m, 2H), 4.03 (dd, J=5.6, 9.0 Hz, 1H), 3.97 (m, 1H), 3.85 (t, J=10.0 Hz, 1H), 3.64 (br d, J=10.4 Hz, 1H), 2.09 (q, J=6.8 Hz, 2H), 1.38 (s, 3H), 1.32 (s, 3H), 1.25–1.45 (m, 6H), 0.92 (s, 9H), 0.89 (t, J=6.9 Hz, 3H), 0.12 (s, 4H); $^{13}$C NMR (CDCl$_3$, 75 MHz) δ 132.8, 129.0, 108.4, 80.9, 77.3, 69.6, 62.0, 32.1, 31.3, 28.0, 25.9, 25.4, 22.3, 18.3, 13.9, –5.5; IR (neat) 3470 (br m), 2930 (s), 2859 (s), 1472 (m), 1380 (m) cm$^{-1}$; MS (CI, NH$_3$) m/z (rel intensity) 376 [(M+NH$_4$)$^+$, 19], 359 [(M+H)$^+$, 100], 341 (97), 318 (28), 92 (22); HRMS (CI, NH$_3$) calcd for C$_{19}$H$_{38}$O$_4$SiH [(M+H)$^+$] 359.2618, found 359.2603; Anal. Calcd for C$_{19}$H$_{38}$O$_4$Si: C, 63.64; H, 10.68. Found: C, 63.62; H, 10.39.

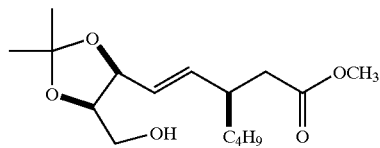

40

Methyl (E)-(3R,6S,7R)-3-Butyl-8-hydroxy-6,7-O-isopropylidenedioxy-4-octenoate (40). Trimethyl orthoacetate (2.85 g, 23.7 mmol) and propionic acid (70 mg, 0.95 mmol) were added to a solution of the (E)-allylic alcohol 37 (1.70 g, 4.74 mmol) in toluene (24 mL). The flask was fitted with a distillation head and the mixture was heated at reflux, distilling off methanol as it formed. GC was used to monitor the disappearance of starting material (t$_R$=5.4 min) and the appearance of product (t$_R$=7.1 min). After 16 h, the mixture was cooled to room temperature and concentrated to give 1.95 g of the desired E-γ,δ-unsaturated ester as a pale yellow oil that was used without further purification. None of the Z-alkene isomer was detected by $^1$H or $^{13}$C NMR. [Purification of a small sample by chromatography (15:1 hex/EtOAc) provided an analytically pure sample of the silyl ether of 40: R$_f$=0.17 (15:1 hex/EtOAc); [α]$^{23}$$_D$=–1.4° (c 0.35, CHCl$_3$); $^1$H NMR (CDCl$_3$, 300 MHz) δ 5.60 (dd, J=7.4, 15.4 Hz, 1H), 5.51 (dd, J=6.6, 15.4 Hz, 1H), 4.58 (t, J=6.5 Hz, 1H), 4.15 (dd, J=6.1, 11.9 Hz, 1H), 3.66 (s, 3H), 3.61 (dd, J=5.4, 10.9 Hz, 1H), 3.57 (dd, J=6.1, 10.8 Hz, 1H), 2.54 (m, 1H), 2.37 (dd, J=6.5, 15.0 Hz, 1H), 2.29 (dd, J=7.8, 15.0 Hz, 1H), 1.48 (s, 3H), 1.36 (s, 3H), 1.2–1.4 (m, 6H), 0.90 (m, 12H), 0.08 (s, 6H); $^{13}$C NMR (CDCl$_3$, 90 MHz) δ 172.8, 136.9, 126.0, 108.4, 78.9, 78.1, 62.8, 51.4, 39.9, 38.9, 34.1, 29.2, 27.9, 25.9, 25.4, 22.6, 18.3, 14.0, –5.3; IR (neat) 2930 (s), 2858 (s), 1742 (s) cm$^{-1}$; MS (CI, NH$_3$) m/z (rel intensity) 432 [(M+NH$_4$)$^+$, 100], 357 (18), 299 (9); HRMS (CI, NH$_3$) calcd for C$_{22}$H$_{42}$O$_5$SiNH$_4$ [(M+NH$_4$)$^+$] 432.3145, found 423.3131; Anal. Calcd for C$_{22}$H$_{42}$O$_5$Si: C, 63.73; H, 10.21. Found: C, 63.68; H, 10.08.]

The crude silyl ether from above was dissolved in THF (25 mL), tetra-n-butylammonium fluoride (5.2 mL of a 1 M soln. in THF, 5.2 mmol) was added, and the resulting mixture was stirred at room temperature. After 1 h, the mixture was diluted with ether (100 mL), washed with water (50 mL) and brine (50 mL), then dried (MgSO$_4$) and concentrated. Chromatography (3:1 to 2:1 hex/EtOAc) provided 1.05 g (74% from 37) of the title compound as a colorless oil. The C(3) stereochemistry of 40 was derived from analysis of the most favorable transition state for the Claisen rearrangement. R$_f$=0.34 (2:1 hex/EtOAc); [α]$^{23}$$_D$=+10.9° (c 0.52, CHCl$_3$); $^1$H NMR (CDCl$_3$, 360 MHz) δ 5.60 (dd, J=7.5, 15.4 Hz, 1H), 5.54 (dd, J=7.2, 15.4 Hz, 1H), 4.62 (t, J=6.7 Hz, 1H), 4.21 (dd, J=6.1, 12.1 Hz, 1H), 3.66 (s, 3H), 3.56 (t, J=6.6 Hz, 2H), 2.42 (dd, J=5.0, 15.0 Hz, 1H), 2.24 (dd, J=9.3, 15.0 Hz, 1H), 2.15 (br t, J=6.4 Hz, 1H), 1.49 (s, 3H), 1.38 (s, 3H), 1.2–1.4 (m, 6H), 0.88 (t, J=6.9 Hz, 3H); $^{13}$C NMR (CDCl$_3$, 90 MHz) δ 173.1, 138.2, 125.9, 108.6, 78.3, 78.1, 61.7, 51.6, 39.7, 39.2, 34.4, 29.1, 27.8, 25.2, 22.5, 13.9; IR (neat) 3500 (br s), 2932 (s), 1738 (s) cm$^{-1}$; MS (CI, NH$_3$) m/z (rel intensity) 318 [(M+NH$_4$)$^+$, 45], 243 (100), 230 (83), 207 (76); HRMS (CI, NH$_3$) calcd for C$_{16}$H$_{28}$O$_5$NH$_4$ [(M+NH$_4$)$^+$] 318.2280, found 318.2298; Anal. Calcd for C$_{16}$H$_{28}$O$_5$: C, 63.97; H, 9.40. Found: C, 63.80; H, 9.35.

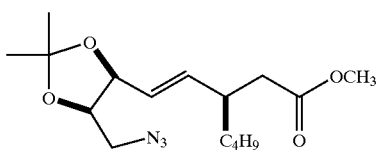

42

Methyl (E)-(3R,6S,7R)-8-Azido-3-butyl-6,7-O-isopropylidenedioxy-4-octenoate (42). Hydrazoic acid (8.3 mL of a 1.2 M solution in benzene, 10.0 mmol)[26] was added to a solution of the alcohol 292 (1.00 g, 3.33 mmol) and triphenylphosphine (1.75 g, 6.65 mmol) in benzene (17 mL). The mixture was cooled to 5° C. and diethyl azodicarboxylate (1.10 mL, 6.65 mmol) was added in a dropwise fashion. The solution was then allowed to warm to room temperature. After 2 h, TLC indicated that starting material was still present. More hydrazoic acid solution (2.8 mL, 3.4 mmol), triphenylphosphine (0.65 g, 2.5 mmol), and DEAD (0.41 mL, 2.5 mmol) were added and the mixture was allowed to stir at room temperature for another 1 h. The mixture was then poured into hexanes (100 mL), resulting in the formation of a white precipitate. The mixture was filtered, and the filtrate was concentrated. Chromatography (15:1 to 10:1 hexane/EtOAc) provided 0.915 g (84%) of the azide 42 as a colorless oil. $R_f$=0.30 (8:1 hex/EtOAc); $[\alpha]^{23}_D$=+52.7° (c 1.42, CHCl$_3$); $^1$H NMR (CDCl$_3$, 300 MHz) δ 5.60 (dd, J=8.3, 15.4 Hz, 1H), 5.47 (dd, J=7.6, 15.4 Hz, 1H), 4.61 (t, J=6.9 Hz, 1H), 4.25 (ddd, J=4.1, 6.7, 7.1 Hz, 1H), 3.64 (s, 3H), 3.27 (dd, J=7.8, 12.8 Hz, 1H), 3.16 (dd, J=4.1, 12.8 Hz, 1H), 2.58 (m, 1H), 2.40 (dd, J=5.6, 15.0 Hz, 1H), 224 (dd, J=8.8, 15.0 Hz, 1H), 1.52 (s, 3H), 1.39 (s, 3H), 1.2–1.5 (m, 6H), 0.89 (t, J=6.8 Hz, 3H); $^{13}$C NMR (CDCl$_3$, 75 MHz) δ 172.5, 138.2, 125.2, 109.1, 78.0, 77.2, 51.7, 51.5, 39.9, 39.1, 34.3, 29.2, 27.9, 25.4, 22.6, 14.0; IR (neat) 2932 (m), 2102 (s), 1738 (s) cm$^{-1}$; MS (CI, NH$_3$) m/z (rel intensity) 343 [(M+NH$_4$)$^+$, 15], 298 (100), 286 (62), 240 (18); HRMS (CI, NH$_3$) calcd for C$_{16}$H$_{27}$N$_3$O$_4$NH$_4$ [(M+NH$_4$)$^+$] 343.2345; found 343.2338; Anal. Calcd for C$_{16}$H$_{27}$N$_3$O$_4$: C, 59.06; H, 8.36; N, 12.91. Found: C, 59.33; H, 8.32; N, 13.11.

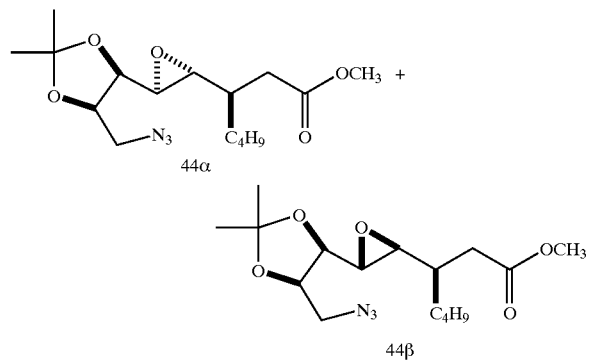

Methyl (3R,4R,5S,6R,7R)-8-Azido-3-butyl-4,5-epoxy-6,7-O-isopropylidenedioxyoctanoate (44α) and Methyl (3R,4S,5R,6R,7R)-8-Azido-3-butyl-4,5-epoxy-6,7-O-isopropylidenedioxyoctanoate (44β). m-Chloroperbenzoic acid (1.48 g, technical grade, 1.18 g pure, 6.8 mmol) was added to a cooled (0° C.) solution of the azide 42 (0.89 g., 2.73 mmol) in CH$_2$Cl$_2$ (14 mL). After 24 h, the mixture was diluted with ether (50 mL) and washed with 1 M NaOH (2×25 mL). The aqueous layers were back-extracted with ether (2×25 mL) and the combined organic layers were washed with saturated NaHCO$_3$ (50 mL) and brine (25 mL), then dried (MgSO$_4$), filtered, and concentrated to provide 0.91 (98% crude) of a mixture (3.5:1 by $^1$H NMR integration) of diastereomeric epoxides that were used without further purification. Purification of a small sample by chromatography (10:1 hex/EtOAc gradient) provided an analytically pure sample of the major diastereomer 44α. Data for 44α: $R_f$=0.23 [8:1 hex/EtOAc (2 elutions)]; $[\alpha]^{23}_D$=+43.3° (c 0.70, CHCl$_3$); $^1$H NMR (CDCl$_3$, 360 MHz) δ 4.36 (td, J=4.5, 6.7 Hz, 1H), 3.68 (s, 3H), 3.65 (dd, J=6.2, 8.5 Hz, 1H), 3.61 (dd, J=4.4, 13.0 Hz, 1H), 3.57 (dd, J=6.9, 13.0 Hz, 1H), 2.84 (dd, J=2.0, 8.5 Hz, 1H), 2.73 (dd, J=2.0, 8.2 Hz, 1H), 2.48 (dd, J=6.1, 15.2 Hz, 1H), 2.35 (dd, J=7.1, 15.2 Hz, 1H), 1.71 (m, 1H), 1.52 (s, 3H), 1.45 (m, 3H), 1.37 (s, 3H), 1.34 (m, 3H), 0.90 (t, J=7.1 Hz, 3H); $^{13}$C NMR (CDCl$_3$, 90 MHz) δ 172.7, 109.9, 77.9, 76.6, 60.9, 55.6, 51.6, 50.2, 38.1, 37.0, 31.3, 29.1, 27.7, 25.2, 13.9; IR (neat) 2934 (m), 2104 (s), 1738 (s) cm$^{-1}$; MS (CI, NH$_3$) m/z (rel intensity) 359 [(M+NH$_4$)$^+$, 43], 342 [(M+H)$^+$, 22], 314 (100), 142 (42); HRMS (CI, NH$_3$) calcd for C$_{16}$H$_{27}$N$_3$O$_5$H [(M+H)$^+$] 342.2029; found 342.2018; Anal. Calcd for C$_{16}$H$_{27}$N$_3$O$_5$: C, 56.29; H, 7.97; N, 12.31. Found: C, 56.66; H, 8.02; N, 12.12.

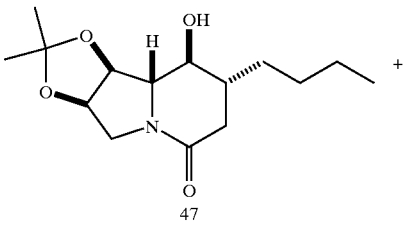

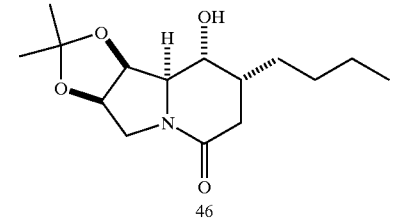

(1S,2R,7R,8S,8aS)-7-Butyl-8-hydroxy-1,2-O-isopropylidenedioxyindolizidin-5-one (299) and (1S,2R,7R, 8R,8aR)-7-Butyl-8-hydroxy-1,2-O-isopropylidenedioxy indolizidin-5-one (46). Palladium hydroxide on carbon (125 mg) was added to a solution of the epoxides 44αβ (3.5:1, 840 mg, 2.5 mmol) in MeOH/EtOAc (1:1, 35 mL). The flask was evacuated (aspirator) and purged with hydrogen three times, and the resulting heterogeneous mixture was stirred under a balloon of hydrogen. After 3 h, the hydrogen was evacuated, the mixture was filtered, and the filtrate was concentrated. The residue was redissolved in MeOH (35 mL), sodium methoxide (66 mg, 1.2 mmol) was added, and the mixture was warmed to reflux. Reaction progress was monitored by IR for the disappearance of the ester and lactone carbonyl stretches at 1730 cm$^{-1}$ and 1780 cm$^{-1}$ and appearance of the lactam carbonyl stretch at 1625 cm$^{-1}$. After 60 h, the mixture was cooled to room temperature and concentrated. The residue was dissolved in CH$_2$Cl$_2$/MeOH (20:1, 10 mL), Florisil (1 g) was added, and the mixture was stirred for 15 min. The suspension was then filtered throgh Celite and the filtrate was concentrated. Chromatography (100:1 to 50:1 CH$_2$Cl$_2$/MeOH) provided 127 mg (18%) of the lactam 47 as a white crystalline solid followed by 415 mg (60%) of the lactam 46 as a white crystalline solid.

Data for 47 (minor): $R_f$=0.31 (20:1 CHCl$_3$/MeOH); $[\alpha]^{23}_D$=−60.0° (c 0.45, CHCl$_3$); mp 194° C.; $^1$H NMR (CDCl$_3$, 300 MHz) δ 4.74 (td, J=2.5, 6.3 Hz, 1H), 4.51 (t, J=6.0 Hz, 1H), 4.18 (dd, J=6.4, 13.7 Hz, 1H), 3.42 (dd, J=2.3, 13.6 Hz, 1H), 3.35 (m, 2H), 2.65 (dd, J=5.2, 17.2 Hz, 1H), 2.4 (br s, 1H), 1.97 (dd, J=11.2, 17.2 Hz, 1H), 1.7–2.0 (m, 3H), 1.57 (s, 3H), 1.38 (s, 3H), 1.05–1.4 (m, 6H), 0.90 (t, J=6.9 Hz, 3H); $^{13}$C NMR (CDCl$_3$, 90 MHz) δ 167.9, 114.1, 84.1, 73.9, 67.5, 49.1, 39.6, 35.8, 30.9, 28.1, 27.7, 25.5, 22.7, 14.0; IR (neat) 3310 (br m), 2931 (m), 1604 (s) cm$^{-1}$; MS (CI, NH$_3$) m/z (rel intensity) 284 [(M+H)$^+$, 100], 226 (20), 208 (12); HRMS (CI, NH$_3$) calcd for C$_{15}$H$_{25}$NO$_4$H [(M+H)$^+$] 284.1862; found 284.1866; Anal. Calcd for C$_{15}$H$_{25}$NO$_4$: C, 63.58; H, 8.89; N, 4.94. Found: C, 63.52; H, 8.86; N, 4.85.

Data for 46 (major): $R_f$=0.26 (20:1 CHCl$_3$/MeOH): $[\alpha]^{23}_D$=−40.0° (c 0.55, CHCl$_3$): mp 131° C.; $^1$H NMR (CDCl$_3$, 300 MHz) δ 4.76 (dd, J=4.1, 5.9 Hz, 1H), 4.71 (t, J=5.9 Hz, 1H), 4.26 (m, 1H), 4.22 (d, J=13.4 Hz, 1H), 3.38 (dd, J=4.0, 6.4 Hz, 1H), 3.25 (br s, 1H), 3.02 (dd, J=4.7, 13.5 Hz, 1H), 2.44 (dd, J=5.7, 17.2 Hz, 1H), 2.33 (dd, J=4.8, 17.2 Hz, 1H), 2.01 (m, 1H), 1.72 (m, 1H), 1.39 (s, 3H), 1.32 (s, 3H), 1.1–1.5 (m, 5H), 0.90 (t, J=6.8 Hz, 3H): $^{13}$C NMR (CDCl$_3$, 90 MHz) δ 168.7, 111.7, 79.9, 77.6, 66.3, 63.8, 50.1, 38.0, 33.8, 29.5, 27.4, 26.3, 24.6, 22.7, 14.0; IR (neat) 3280 (br m), 2922 (m), 1621 (s) cm$^{-1}$; MS (CI, NH$_3$) m/z (rel intensity) 284 [(M+H)$^+$, 100], 206 (4); HRMS (CI, NH$_3$) calcd for C$_{15}$H$_{25}$NO$_4$H [(M+H)$^+$] 284.1862; found 284.1856; Anal. Calcd for C$_{15}$H$_{25}$NO$_4$: C, 63.58; H, 8.89; N, 4.94. Found: C, 63.29; H, 8.88; N, 4.92.

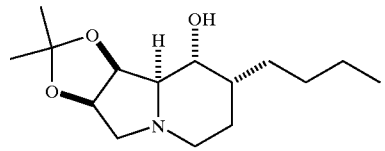

50

(1S,2R,7R,8R,8aR)-7-Butyl-8-hydroyx-1,2-O-isopropylidenedioxy-indolizidine (50) Reduction of the lactam 46 (300 mg, 1.06 mmol) was carried out with borane-methyl sulfide complex. Chromatography (100:1 to 50:1 CH$_2$Cl$_2$/MeOH gradient) provided 280 mg (98%) of the indolizidine 50 as a white crystalline solid. $R_f$=0.22 (20:1 CHCl$_3$/MeOH); $[\alpha]^{23}_D$=−56.8° (c 0.74, CHCl$_3$); mp 38° C.; $^1$H NMR (CDCl$_3$, 300 MHz) δ 4.63 (dd, J=4.2, 6.2 Hz, 1H, H$_1$), 4.60 (dd, J=4.0, 6.2 Hz, 1H, H$_2$), 3.99 (m, 1H, H$_8$), 3.12 (d, J=10.7 Hz, 1H, H$_{3eq}$), 2.75 (ddd, J=2.7, 4.2, 10.9 Hz, 1H, H$_{5eq}$), 2.15 (dd, J=3.9, 10.7 Hz, 1H, H$_{3ax}$), 2.10 (dt, J=4.2, 11.0 Hz, 1H, H$_{5ax}$), 1.93 (m, 3H, H$_{8a}$+H$_7$+H$_{OH}$), 1.5–1.8 (m, 3H), 1.51 (s, 3H), 1.33 (s, 3H), 1.1–1.4 (m, 5H), 0.90 (t, J=7.0 Hz, 3H, H$_{12}$); $^{13}$C NMR (CDCl$_3$, 75 MHz) δ 111.3, 79.6, 78.4, 69.9, 67.1, 59.9, 46.3, 38.3, 30.5, 27.4, 26.1, 25.0, 23.7, 23.1, 14.2; IR (neat) 3450 (br m), 2930 (s), 2870 (m), 2788 (m), 1377 (m) cm$^{-1}$; MS (CI, NH$_3$) m/z (rel intensity) 270 [(M+H)$^+$, 100], 252 (46), 194 (36); HRMS (CI, NH$_3$) calcd for C$_{15}$H$_{27}$NO$_3$H [(M+H)$^+$] 270.2069; found 270.2061; Anal. Calcd for C$_{15}$H$_{27}$NO$_3$: C, 66.88; H, 10.10; N, 5.20. Found: C, 66.53; H, 10.39; N, 5.27.

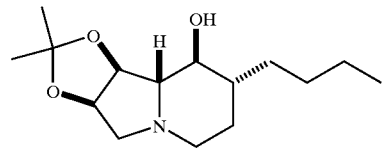

54

(1S,2R,7R,8S,8aS)-7-Butyl-8-hydroxy-1,2-O-isopropylidenedioxyindolizidine (54) Reduction of the lactam 47 (120 mg, 0.42 mmol) was carried out with borane-methyl sulfide complex. Chromatography (100:1 to 50:1 CH$_2$Cl$_2$/MeOH gradient) provided 105 mg (92%) of the indolizidine 54 as a white crystalline solid. $R_f$=0.31 (20:1 CHCl$_3$/MeOH); $[\alpha]^{23}_D$=−65.1° (c 0.37, CHCl$_3$); mp 82° C.; $^1$H NMR (CDCl$_3$, 300 MHz) δ 4.71 (td, J=5.2, 6.6 Hz, 1H, H$_2$), 4.44 (dd, J=6.1, 7.3 Hz, 1H, H$_1$), 3.37 (dd, J=6.4, 9.3 Hz, 1H, H$_{3eq}$), 3.11 (br t, J=8.6 Hz, 1H, H$_8$), 2.90 (m, 1H, H$_{5eq}$), 2.38 (dd, J=5.1, 9.3 Hz, 1H, H$_{3ax}$), 2.17 (td, J=2.8, 11.3 Hz, 1H, H$_{5ax}$), 2.06 (br s, 1H, H$_{OH}$), 2.01 (dd, J=6.0, 9.1 Hz, 1H, H$_{8a}$), 1.79 (m, 2H), 1.53 (s, 3H), 1.34 (s, 3H), 1.1–1.5 (m, 7H), 0.90 (t, J=7.0 Hz, 3H, H$_{12}$); $^{13}$C NMR (CDCl$_3$, 75 MHz) δ 114.3, 83.6, 77.9, 75.3, 74.1, 59.6, 51.3, 43.7, 31.1, 29.4, 28.9, 27.2, 25.1, 23.0, 14.1; IR (neat) 3335 (br m), 2913 (s), 2858 (m), 2805 (m), 1381 (m) cm$^{-1}$; MS (CI, CH$_4$ and NH$_3$) m/z (rel intensity) 270 [(M+H)$^+$, 100], 252 (27), 194 (31); HRMS (CI, CH$_4$ and NH$_3$) calcd for C$_{15}$H$_{27}$NO$_3$H [(M+H)$^+$] 270.2069; found 270.2080; Anal. Calcd for C$_{15}$H$_{27}$NO$_3$: C, 66.88; H, 10.10; N, 5.20. Found: C, 66.76; H, 10.36; N, 5.20.

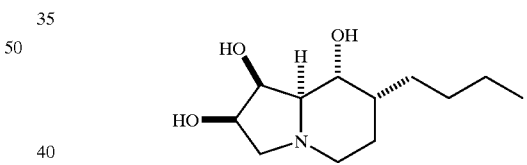

52

(1S,2R,7R,8R,8aR)-7-Butyl-1,2,8-trihydroxyindolizidine [(7R)-7-Butyl-swainsonine] (52). A solution of the indolizidine 50 (97 mg, 0.33 mmol) in THF (2 mL) was treated with 6 N HCl (2 mL). After 24 h, the solution was concentrated. The residue was dissolved in MeOH (5 mL). Dowex 1×8 200 OH$^-$ resin (500 mg) was added, and the mixture was stirred at room temperature. After 15 min, the mixture was filtered, and the filtrate concentrated to give a white solid. Recrystallization from EtOAc provided 61 mg (81%) of the title compound (52) in three crops. $R_f$=0.23 (50:25:1 EtOAc/EtOH/Aq. NH$_4$OH); $[\alpha]^{23}_D$=−88.1° (c 0.75, MeOH): mp 156° C.; $^1$H NMR (CD$_3$OD, 360 MHz) δ 4.19 (m, 1H), 4.09 (dd, J=3.5, 5.5 Hz, 1H), 3.94 (dd, J=4.8, 10.1 Hz, 1H), 3.28 (m, 1H), 2.85 (d, J=10.3 Hz, 1H), 2.66 (m, 1H), 2.42 (dd, J=7.9, 9.9 Hz, 1H), 2.1 (m, 1H), 1.98 (dd, J=2.9, 10.0 Hz, 1H), 1.87 (m, 1H), 1.56–1.72 (m, 3H), 1.15–1.45 (m, 5H), 0.90 (t, J=6.7 Hz, 3H); $^{13}$C NMR (CD$_3$OD, 90 MHz) δ 71.1, 70.1, 69.8, 68.6, 63.2, 47.8, 39.8, 31.8, 27.7, 24.8, 24.3, 14.6; IR (neat) 3370 (br m), 2934 (s), 2880 (m), cm$^{-1}$; MS (CI, CH$_4$ and NH$_3$) m/z (rel intensity) 230 [(M+H)$^+$, 100], 212 (67), 194 (30), 176 (21); HRMS (CI, CH$_4$ and NH$_3$) calcd for C$_{12}$H$_{23}$NO$_3$H [(M+H)$^+$] 230.1756; found 230.1746; Anal. Calcd for C$_{12}$H$_{23}$NO$_3$: C, 62.84; H, 10.11; N, 6.11. Found: C, 62.46; H, 10.08; N, 6.09.

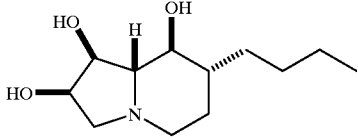

56

(1S,2R,7R,8S,8aS)-7-Butyl-1,2,8-trihydroxyindolizidine [(7R)-7-Butyl-8,8a-deipiswainsonine] (56). The acetonide of the indolizidine 54 (80 mg, 0.27 mmol) was hydrolyzed with 6 N HCl in THF as above. Recrystallization from EtOAc provided 51 mg (83%) of the title compound (45) in three crops. $R_f$=0.37 (50:25:1 EtOAc/EtOH/Aq. NH$_4$OH); $[\alpha]^{23}_D$=−60.6° (c 1.30, MeOH); mp 120° C.; $^1$H NMR (CDCl$_3$, 360 MHz) δ 4.21 (dd, J=6.4, 11.9 Hz, 1H), 3.7–4.3 (br m, 3H, D$_2$O exchangeable), 3.91 (t, J=7.3 Hz, 1H), 3.46 (dd, J=6.8, 9.8 Hz, 1H), 3.19 (t, J=9.0 Hz, 1H), 2.91 (d, J=11.2 Hz, 1H), 2.22 (dd, J=4.9, 9.9 Hz, 1H), 2.08 (dt, J=3, 11 Hz, 1H), 1.90 (t, J=8.2 Hz, 1H), 1.82 (m, 2H), 1.0–1.5 (m, 7H), 0.90 (t, J=7.0 Hz, 3H); $^{13}$C NMR (CDCl$_3$, 90 MHz) δ 75.0, 71.6, 67.8, 61.2, 51.7, 43.5, 31.1, 29.6, 28.9, 23.1, 14.1; IR (neat) 3300 (br s), 2929 (s), 2860 (m), 2805 (m), 1466 (m) cm$^{-1}$; MS (CI, CH$_4$ and NH$_3$) m/z (rel intensity) 230 [(M+H)$^+$, 58], 212 (100), 194 (14); HRMS (CI, NH$_3$) calcd for C$_{12}$H$_{23}$NO$_3$H [(M+H)$^+$] 230.1756; found 230.1759; Anal. Calcd for C$_{12}$H$_{23}$NO$_3$: C, 62.84; H, 10.11; N, 6.11. Found: C, 62.47; H, 10.11; N, 6.13.

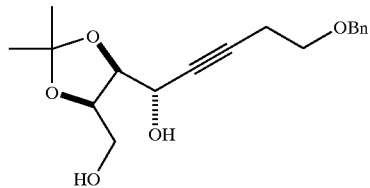

36

(5S,6S,7R)-1-Benzyloxy-5,8-dihydroyx-6,7-O-isopropylidenedioxy-3-octyne (288). 2,3-O-Isopropylidene-D-erythrose was prepared via the diisobutylaluminum hydride reduction of 2,3-O-isopropylidene-D-erythronolactone. 4-Benzyloxybutynylmagnesium chloride was prepared by adding isopropylmagnesium chloride (10.0 mL of a 2 M soln. in ether, 20 mmol) to a cooled (0° C.) solution of 4-benzyloxy-1-butyne (3.20 g, 20.0 mmol) in THF (20 mL) and then allowing the solution to warm to room temperature. The 4-benzyloxybutynyl-magnesium chloride solution was transferred via cannula into a cooled (−78° C.) solution of 2,3-O-isopropylidene-D-erythrose (1.30 g, 8.1 mmol). The resutling mixture was stirred for 30 min at −78° C., and was then allowed to warm slowly to 0° C. After 6 h, the reaction was quenched by the addition of saturated aqueous NH$_4$Cl (100 mL). The mixture was extracted with ether (2×100 mL). The combined organic phases were washed with water (50 mL) and brine (50 mL), and then dried (MgSO$_4$), and concentrated. Chromatography (3:1 to 1:1 hex/EtOAc gradient) provided 2.62 g (100%) of the title compound as a colorless oil. The stereochemistry of 36 was assigned based on analogy to the results reported by Mekki et al. on the addition of similar alkynyl Grignard reagents to 2,3-O-iropropylidene-D-erythrose.[18]s $R_f$=0.10 (2:1 hex/EtOAc); $[\alpha]^{23}_D$=−18.0° (c 0.95, CHCl$_3$); $^1$H NMR (CDCl$_3$, 300 MHz) δ 7.2–7.4 (m, 5H), 4.54 (s, 2H), 4.52 (m, 1H), 4.29 (td, J=4.3, 6.0 Hz, 1H), 4.19 (t, J=6.3 Hz, 1H), 3.88 (m, 3H), 3.60 (t, J=6.8 Hz, 2H), 3.10 (m, 1H), 2.54 (td, J=1.9, 6.8 Hz, 2H), 1.48 (s, 3H), 1.37 (s, 3H); $^{13}$C NMR (CDCl$_3$, 75 MHz) δ 137.9, 128.3, 127.7, 108.5, 83.8, 79.5, 79.2, 77.2, 73.0, 68.2, 61.7, 60.4, 27.4, 25.2, 20.3; IR (neat) 3390 (br s), 2985 (m), 2871 (m), 1371 (s) cm$^{-1}$; MS (CI, NH$_3$) m/z (rel intensity) 338 [(M+NH$_4$)$^+$, 93], 280 (100), 203 (77), 185 (60); HRMS (CI, NH$_3$) calcd for C$_{18}$H$_{24}$O$_5$NH$_4$ [(M+NH$_4$)$^+$] 338.1967; found 338.1961; Anal. Calcd for C$_{18}$H$_{24}$O$_5$: C, 67.48; H, 7.55. Found: C, 67.137; H, 7.59.

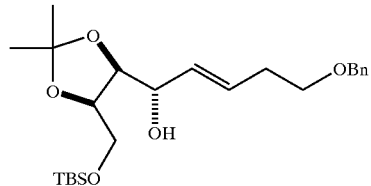

38

(E)-(5S,6S,7R)-1-Benzyloxy-8-tert-butyldimethylsilyloxy-4-hydroxy-2,3-O-isopropylidenedioxy-3-octene (38). Sodium bis(2-methoxyethoxy)-aluminum hydride (Red-Al) (3.77 mL of a 70% soln. in toluene. 12.2 mmol) was added in a dropwise fashion to a cooled (0° C.) solution of the diol 36 (1.20 g, 3.75 mmol) in ether (12 mL). The solution was allowed to warm to room temperature. After 3 h, the mixture was again cooled to 0° C. and the reaction was quenched by the slow dropwise addition of 1N H$_2$SO$_4$ until no more bubbling was observed. The mixture was poured into ether (100 mL) and washed with water (3×50 mL). The aqueous layers were back-extracted with ether (100 mL). The combined organic layers were washed with brine (50 mL), then dried (MgSO$_4$), and concentrated to give 1.10 g of crude (E)-alkene that was used without further purification [A small sample was purified by chromatography (4:1 hex/EtOAc) to obtain an analytically pure sample of (E)-(5S,6S,7R)-1-Benzyloxy-2,3-O-isopropylidene-1,2,3,4-tetrahydroxy-3-octene: $R_f$=0.32 (2:1 hex/EtOAc—3 elutions); $[\alpha]^{23}_D$=−25.3° (c 0.75, CHCl$_3$); $^1$H NMR (CDCl$_3$, 300 MHz) δ 7.2–7.4 (m, 5H), 5.81 (dt, J=6.5, 15.6 Hz, 1H), 5.67 (dd, J=6.0, 15.5 Hz, 1H), 4.51 (s, 2H), 4.27 (m, 2H), 4.01 (dd, J=5.8, 8.3 Hz, 1H), 3.7–3.9 (m, 2H), 3.54 (t, J=6.6 Hz, 2H), 3.22 (m, 2H), 2.41 (q, J=6.5 Hz, 2H), 1.41 (s, 3H), 1.34 (s, 3H); $^{13}$C NMR (CDCl$_3$, 75 MHz) δ 138.2, 131.2, 130.0, 128.3, 127.6, 127.5, 108.3, 79.6, 77.4, 72.9, 70.5, 69.6, 60.8, 32.8, 27.8, 25.3; IR (neat) 3375 (br s), 2985 (m), 2934 (s), 2868 (s), 1380 (m) cm$^{-1}$; MS (CI, NH$_3$) m/z (rel intensity) 340 [(M+NH$_4$)$^+$, 68], 322 (68), 282 (100), 247 (44), 91 (50); HRMS (CI, NH$_3$) calcd for C$_{18}$H$_{26}$O$_5$NH$_4$ [(M+NH$_4$)$^+$] 340.2124, found 340.2137; Anal. Calcd for C$_{18}$H$_{26}$O$_5$: C, 67.06; H, 8.13. Found: C, 66.93; H, 8.05.]

The crude E-alkenyl diol was dissolved in THF/DMF (2:1, 15 mL), and the solution was cooled to 0° C. tert-Butyldimethylsilyl chloride (0.59 g, 3.9 mmol) and imidazole (0.58 g, 8.5 mmol) were added, and the solution was stirred at 0° C. for 2 h. The mixture was then diluted with ether (100 mL) and washed with 1 M HCl (2×50 mL), sat. NaHCO$_3$ (50 mL), and brine (50 mL). The organic layer was dried (MgSO$_4$) and concentrated. Chromatography (10:1 hex/EtOAc) provided 1.15 g (73% from 36) of the (E)-allylic alcohol 38 as a colorless oil. $R_f$=0.66 (2:1 hex/EtOAc); $[\alpha]^{23}_D$=−17.6° (c 1.06, CHCl$_3$); $^1$H NMR (CDCl$_3$, 300 MHz) δ 7.2–7.4 (m, 5H), 5.86 (dtd, J=1.1, 6.7, 15.6 Hz, 1H), 5.70 (dd, J=5.3, 15.5 Hz, 1H), 4.51 (s, 2H), 4.27 (m, 1H), 4.23 (ddd, J=3.8, 5.4, 9.7 Hz, 1H), 4.13 (d, J=3.2 Hz, 1H), 4.03 (dd, J=5.5, 9.1 Hz, 1H), 3.84 (t, J=10.4 Hz, 1H), 3.63 (dd, J=3.6, 10.5 Hz, 1H), 3.54 (t, J=7.0 Hz, 2H), 2.42 (q, J=6.8 Hz, 2H), 1.38 (s, 3H), 1.32 (s, 3H), 0.91 (s, 9H), 0.12 (s, 6H); $^{13}$C NMR (CDCl$_3$, 75 MHz) δ 138.5, 131.0, 128.5, 128.2, 127.5, 127.3, 108.4, 80.7, 77.2, 72.8, 69.8, 69.4, 61.9, 32.9, 28.0, 25.8, 25.3, 18.2, −5.5; IR (neat) 3450 (br m), 2934 (s), 2858 (s) cm$^{-1}$; MS (CI, NH$_3$) m/z (rel intensity) 454 [(M+NH$_4$)$^+$, 6], 437 [(M+H)$^+$, 4], 419 (100), 396 (43), 361 (43); HRMS (CI, NH$_3$) calcd for C$_{24}$H$_{40}$O$_5$H [(M+H)$^+$] 437.2723 found 437.2728; Anal. Calcd for C$_{24}$H$_{40}$O$_5$Si: C, 66.02; H, 9.23. Found: C, 65.81; H, 9.08.

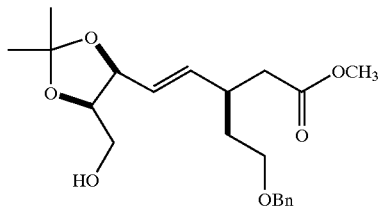

41

Methyl E-(3R,6S,7R)-3-[2-(Benzyloxy)ethyl]-8-hydroxy-6,7-O-isopropylidenedioxy-4-octenoate (41). Trimethyl orthoacetate (1.15 g, 9.6 mmol) and propionic acid (30 mg, 0.38 mmol) were added to a solution of the E-allylic alcohol 38 (0.840 g, 1.92 mmol) in toluene (10 mL). The flask was fitted with a distillation head, and the mixture was heated at reflux, distilling off methanol as it formed. After 16 h, the mixture was cooled to room temperature and concentrated. Chromatography (10:1 to 8:1 hex/EtOAc gradient) provided 0.930 g (88%) of the silyl ether protected E-γ,δ-unsaturated ester as a colorless oil. None of the Z-alkenyl isomer was detected by $^1$H or $^{13}$C NMR. [R$_f$=0.33 (8:1 hex/EtOAc); [α]$^{23}_D$=+8.1° (c 1.71, CHCl$_3$); $^1$H NMR (CDCl$_3$, 300 MHz) δ 7.2–7.4 (m, 5H), 5.62 (dd, J=7.4, 15.4 Hz, 1H), 5.54 (dd, J=6.6, 15.4 Hz, 1H), 4.55 (t, J=6.5 Hz, 1H), 4.47 (s, 2H), 4.14 (dd, J=5.9, 12.1 Hz, 1H), 3.63 (s, 3H), 3.58 (d, J=5.8 Hz, 2H), 3.49 (m, 2H), 2.77 (m, 1H), 2.41 (dd, J=6.3, 15.2 Hz, 1H), 2.31 (dd, J=7.8, 15.2 Hz, 1H), 1.78 (m, 1H), 1.63 (m, 1H), 1.46 (s, 3H), 1.36 (s, 3H), 0.90 (s, 9H), 0.08 (s, 6H); $^{13}$C NMR (CDCl$_3$, 90 MHz) δ 172.2, 138.4, 136.1, 128.2, 127.5, 127.4, 126.6, 108.4, 78.9, 78.1, 72.9, 68.0, 62.7, 51.3, 39.7, 36.0, 34.3, 27.9, 25.9, 25.4, 18.3, −5.2; IR (neat) 2930 (s), 2856 (s), 1741 (s) cm$^{-1}$; MS (CI, NH$_3$) m/z (rel intensity) 510 [(M+NH$_4$)$^+$, 27], 452 (55), 435 (100), 327 (84), 195 (84); HRMS (CI, NH$_3$) calcd for C$_{27}$H$_{44}$O$_6$SiNH$_4$ [(M+NH$_4$)$^+$] 510.3251, found 510.3237; Anal. Calcd for C$_{27}$H$_{44}$O$_6$Si: C, 65.82; H, 9.00. Found: C, 65.86; H, 8.78.]

Tetra-n-butylammonium fluoride (2.0 mL of a 1 M soln. in THF, 2.0 mmol) was added to a solution of the alkenyl ester (0.90 g, 1.83 mmol) in THF (9 mL). After 1 h, the mixture was diluted with ether (50 mL), washed with water (25 mL) and brine (25 mL), then dried (MgSO$_4$) and concentrated. Chromatography (2:1 hex/EtOAc) provided 0.62 g (90%) of the alcohol 41 as a colorless oil. R$_f$=0.10 (2:1 hex/EtOAc); [α]$^{23}_D$=+28.8° (c 0.80, CHCl$_3$); $^1$H NMR (CDCl$_3$, 360 MHz) δ 7.2–7.4 (m, 5H), 5.60 (dd, J=7.7, 15.4 Hz, 1H), 5.54 (dd, J=7.2, 15.4 Hz, 1H), 4.59 (t, J=6.8 Hz, 1H), 4.47 (s, 2H), 4.19 (dd, J=6.0, 12.4 Hz, 1H), 3.64 (s, 3H), 3.52 (t, J=6.2 Hz, 2H), 3.47 (m, 2H), 2.77 (m, 1H), 2.45 (dd, J=5.1, 15.2 Hz, 1H), 2.38 (t, J=6.4 Hz, 1H), 2.28 (dd, J=9.2, 15.2 Hz, 1H), 1.74 (m, 1H), 1.63 (m, 1H), 1.48 (s, 3H), 1.37 (s, 3H); $^{13}$C NMR (CDCl$_3$, 90 MHz) δ 172.7, 138.2, 136.8, 128.2, 127.5, 127.4, 126.4, 108.5, 78.2, 77.8, 72.8, 67.7, 61.5, 51.5, 39.5, 36.1, 34.3, 27.7, 25.1; IR (neat) 3488 (m), 2934 (s), 2868 (s), 1737 (s) cm$^{-1}$; MS (CI, NH$_3$) m/z (rel intensity) 396 [(M+NH$_4$)$^+$, 32], 321 (73), 303 (63), 213 (64), 195 (100); HRMS (CI, NH$_3$) calcd for C$_{21}$H$_{30}$O$_6$NH$_4$ [(M+NH$_4$)$^+$] 396.2386, found 396.2398; Anal. Calcd for C$_{21}$H$_{30}$O$_6$: C, 66.65; H, 7.99. Found: C, 66.79; H, 7.92.

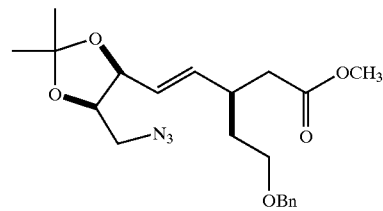

43

Methyl E-(3R,6S,7R)-8-Azido-3-[2-(benzyloxy)ethyl]-6,7-O-isopropylidenedi oxy-4-octenoate (43). Hydrazoic acid (4.0 mL of a 1.2 M solution in benzene, 4.8 mmol)$^{26}$ was added to a solution of the alcohol 41 (0.60 g, 1.6 mmol) and triphenylphosphine (0.84 g, 3.2 mmol) in benzene (8 mL). The mixture was cooled to 5° C. and diethyl azodicarboxylate (0.55 mL, 3.2 mmol) was added in a dropwise fashion. The solution was then allowed to warm to room temperature. After 2 h, TLC indicated that starting material was still present. More hydrazoic acid solution (1.3 mL, 1.6 mmol), triphenylphosphine (0.31 g, 1.2 mmol), and DEAD (0.20 mL, 1.2 mmol), were added and the mixture was allowed to stir at room temperature for another 1 h. The mixture was then poured into hexanes (50 mL), resulting in the formation of a white precipitate. The mixture was filtered, and the filtrate was concentrated. Chromatography (8:1 to 6:1 hexane/EtOAc) provided 0.560 g (87%) of the azide 43 as a colorless oil. R$_f$=0.17 (6:1 hex/EtOAc); [α]$^{23}_D$=+52.2° (c 1.25, CHCl$_3$); $^1$H NMR (CDCl$_3$, 360 MHz) δ 7.2–7.4 (m, 5H), 5.62 (dd, J=8.6, 15.4 Hz, 1H), 5.47 (dd, J=7.6, 15.4 Hz, 1H), 4.59 (t, J=7.1 Hz, 1H), 4.59 (ABq, J=12.0 Hz, Δν=13.0 Hz, 2H), 4.23 (ddd, J=4.1, 6.6, 7.8 Hz, 1H), 3.64 (s, 3H), 3.21 (dd, J=7.8, 12.8 Hz, 1H), 3.09 (dd, J=4.0, 12.8 Hz, 1H), 2.79 (m, 1H), 2.44 (dd, J=5.5, 15.2 Hz, 1H), 2.29 (dd, J=8.8, 15.2 Hz, 1H), 1.77 (m, 1H), 1.65 (m, 1H), 1.51 (s, 3H), 1.37 (s, 3H); $^{13}$C NMR (CDCl$_3$, 90 MHz) δ 162.3, 138.3, 137.4, 128.3, 127.6, 127.5, 125.7, 109.1, 77.8, 77.1, 72.9, 67.8, 51.5, 39.6, 36.1, 34.3, 27.8, 25.2; IR (neat) 2988 (m), 2935 (m), 2862 (m), 2101 (s), 1738 (s) cm$^{-1}$; MS (CI, NH$_3$) m/z (rel intensity) 421 [(M+NH$_4$)$^+$, 3], 376 (100), 318 (18); HRMS (CI, NH$_3$) calcd for C$_{21}$H$_{29}$N$_3$O$_5$NH$_4$ [(M+NH$_4$)$^+$] 421.2451; found 421.2444; Anal. Calcd for C$_{21}$H$_{29}$N$_3$O$_5$: C, 62.51; H, 7.24; N, 10.41. Found: C, 62.62; H, 7.36; N, 10.54.

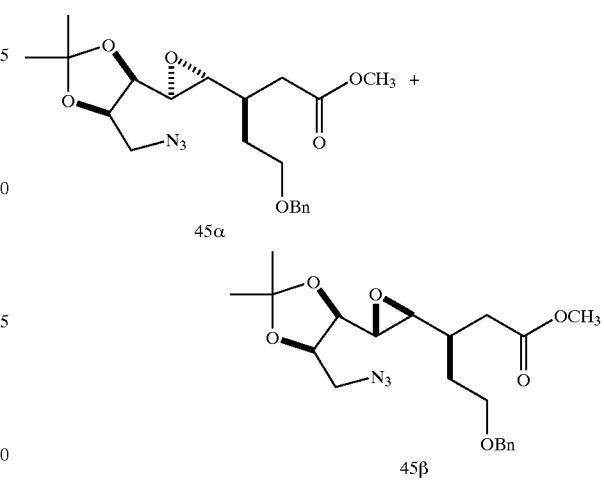

Methyl (3R,4R,5S,6R,7R)-8-Azido-3-[2-(benzyloxy) ethyl]-4,5-epoxy-6,7-O-isopropylidenedioxyoctanoate (45α) and Methyl (3R,4S,6R,6R,7R)-8-Azido-3-[2-(benzyloxy)ethyl]-4,5-epoxy-6,7-O-isopropylidenedioxyoctanoate (45β). m-Chloroperbenzoic acid (0.67 g, technical grade, 0.54 g pure, 3.1 mmol) was added to a cooled (0° C.) solution of the azide 43 (0.50 g, 1.2 mmol) in CH$_2$Cl$_2$ (6 mL). After 24 h, the mixture was diluted with ether (50 mL) and washed with 1 M NaOH (2×25 mL). The aqueous layers were back-extracted with ether (2×25 mL), and the combined organic layers were washed with saturated NaHCO$_3$ (25 mL) and brine (25 mL), then dried (MgSO$_4$), filtered, and concentrated. Chromatography (4:1 hex/EtOAc) provided 475 mg (91%) of a mixture (3:1 by $^1$H NMR integration) of epoxides 45α and 45β. R$_f$=0.30 [6:1 hex/EtOAc (3 elutions)]; $^1$H NMR (CDCl$_3$, 360 MHz, major isomer) δ 7.2–7.4 (m, 5H), 4.50 (s, 2H), 4.34 (ddd, J=3.9, 6.5, 7.2 Hz, 1H), 3.66 (s, 3H), 3.65 (dd, J=5.7, 8.9 Hz, 1H), 3.58 (m, 3H), 3.50 (dd, J=7.3, 13.1 Hz, 1H), 2.83 (m, 2H), 2.49 (dd, J=6.2, 15.4 Hz, 1H), 2.42 (dd, J=6.7, 15.4 Hz, 1H), 1.75 (m, 1H), 1.80 (m, 2H), 1.50 (s, 3H), 1.35 (s, 3H); $^{13}$C NMR (CDCl$_3$, 90 MHz, major isomer) δ 172.4, 138.3, 128.3, 127.54, 127.47, 109.9, 77.7, 76.6, 72.8, 67.2, 60.5, 55.3, 51.6, 50.4, 36.6, 35.1, 31.2, 27.5, 25.0; IR (neat) 2988 (m), 2102 (s), 1738 (s) cm$^{-1}$; MS (CI, NH$_3$) m/z (rel intensity) 437 [(M+NH$_4$)$^+$, 34], 392 (100), 360 (60), 143 (14), 108 (50); HRMS (CI, NH$_3$) calcd for C$_{21}$H$_{29}$N$_3$O$_6$NH$_4$ [(M+NH$_4$)$^+$] 437.2400; found 437.2382; Anal. Calcd for C$_{21}$H$_{29}$N$_3$O$_6$: C, 60.13; H, 6.97; N, 10.02. Found: C, 60.11; H, 7.04; N, 9.96.

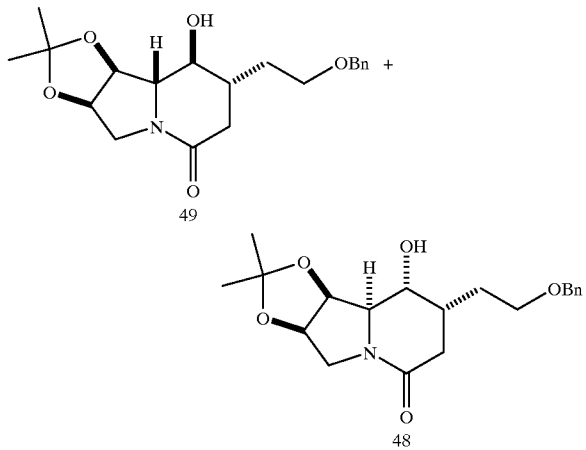

49

48

(1S,2R,7R,8S,8aS)-7-[2-(Benzyloxy)ethyl]-8-hydroxy-1,2-O-isopropylidenedioxyindolizidin-5-one (49) and (1S,2R,7R,8R,8aR)-7-[2-(Benzyloxy)ethyl]-8-hydroxy-1,2-O-isopropylidenedioxyindolizidin-5-one (48). Palladium hydroxide on carbon (50 mg) was added to a solution of the epoxides 45αβ (320 mg, 0.76 mmol) in MeOH/EtOAc (1:1, 12 mL). The flask was evacuated (aspirator) and purged with hydrogen three times, and the resulting heterogeneous mixture was stirred under a balloon of hydrogen. After 3 h, the hydrogen was evacuated, the mixture was filtered, and the filtrate was concentrated. The residue was redissolved in MeOH (12 mL), sodium methoxide (21 mg, 0.38 mmol) was added, and the mixture was warmed to reflux. Reaction progress was monitored by IR for the disappearance of the ester and lactone carbonyl stretches at 1730 cm$^{-1}$ and 1780 cm$^{-1}$ and appearance of the lactam carbonyl stretch at 16.25 cm$^{-1}$. After 48 h, the mixture was cooled to room temperature and concentrated. The residue was dissolved in CH$_2$Cl$_2$/MeOH (20:1, 10 mL), Florisil (1 g) was added, and the mixture was stirred for 15 min. The suspension was then filtered through Celite and the filtrate was concentrated. Chromatography (100:1 to 50:1 CH$_2$Cl$_2$/MeOH) provided 47 mg (17%) of the lactam 49 as a white crystalline solid followed by 188 mg (68%) of the lactam 48 as a colorless oil that crystallized upon standing.

Data for 49 (minor): R$_f$=0.28 (20:1 CHCl$_3$/MeOH); [α]$^{23}_D$=−33.3° (c 0.45, CHCl$_3$); mp 109° C.; $^1$H NMR (CDCl$_3$, 300 MHz) δ 7.2–7.4 (m, 5H), 4.72 (td, J=2.9, 6.5 Hz, 1H), 4.54 (m, 1H), 4.53 (ABq, J=12.0 Hz, Δν=27.4 Hz, 2H), 4.19 (dd, J=6.5, 13.6 Hz, 1H), 3.61 (ddd, J=3.6, 6.0, 9.6 Hz, 1H), 3.51 (ddd, J=3.3, 8.3, 9.6 Hz, 1H), 3.38 (m, 3H), 2.54 (m, 1H), 1.95–2.15 (m, 2H), 1.7–1.9 (m, 2H), 1.58 (s, 3H), 1.36 (s, 3H); $^{13}$C NMR (CDCl$_3$, 75 MHz) δ 167.3, 137.0, 128.5, 127.9, 127.8, 113.9, 84.1, 76.9, 73.6, 73.4, 67.8, 67.7, 49.3, 39.4, 36.9, 32.9, 27.7, 25.4; IR (neat) 3330 (br m), 2936 (m), 1621 (s) cm$^{-1}$; MS (CI, NH$_3$) m/z (rel intensity) 362 [(M+H)$^+$, 100]; HRMS (CI, NH$_3$) calcd for C$_{20}$H$_{27}$NO$_5$H [(M+NH$_4$)$^+$] 362.1967; found 362.1965; Anal. Calcd for C$_{20}$H$_{27}$NO$_5$: C, 66.46; H, 7.53; N, 3.88. Found: C, 66.39; H, 7.54; N, 3.91.

Data for 48 (major): R$_f$=0.25 (20:1 CHCl$_3$/MeOH); [α]$^{23}_D$=−36.4° (c 0.55, CHCl$_3$); mp 96–98° C.; $^1$H NMR (CDCl$_3$, 300 MHz) δ 7.2–7.4 (m, 5H), 4.71 (m, 2H), 4.55 (s, 2H), 4.25 (m, 1H), 4.22 (d, J=13.3 Hz, 1H), 3.85 (d, J=5.9 Hz, 1H), 3.64 (ddd, J=4.1, 5.3, 9.5 Hz, 1H), 3.56 (td, J=3.2, 9.4 Hz, 1H), 3.35 (dd, J=4.0, 6.3 Hz, 1H), 3.01 (dd, J=4.7, 13.5 Hz, 1H), 2.39 (d, J=5.4 Hz, 2H), 2.23 (m, 1H), 1.97 (m, 1H), 1.61 (m, 1H), 1.39 (s, 3H), 1.31 (s, 3H); $^{13}$C NMR (CDCl$_3$, 75 MHz) δ 168.2, 137.3, 128.5, 127.9, 127.8, 111.8, 80.0, 77.6, 73.4, 68.7, 66.0, 63.9, 50.1, 37.1, 35.5, 29.8, 26.4, 24.7; IR (neat) 3370 (br m), 2935 (m), 2864 (m), 1633 (s) cm$^{-1}$; MS (CI, NH$_3$) m/z (rel intensity) 362 [(M+H)$^+$, 100], 272 (18); HRMS (CI, NH$_3$) calcd for C$_{20}$H$_{27}$NO$_5$H [(M+H)$^+$] 362.1967; found 362.1958; Anal. Calcd for C$_{20}$H$_{27}$NO$_5$: C, 66.46; H, 7.53; N, 3.88. Found: C, 66.57; H, 7.41; N, 3.87.

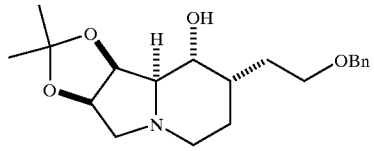

51

(1S,2R,7R,8R,8aR)-7-[2-(Benzyloxy)ethyl]-8-hydroxy-1,2-O-isopropylidenedioxyindolizidine (51) Reduction of the lactam 48 (75 mg, 0.21 mmol) was carried out with borane-methyl sulfide complex. Chromatography (100:1 to 50:1 CH$_2$Cl$_2$/MeOH gradient) provided 55 mg (76%) of the indolizidine 51 as a colorless oil. R$_f$=0.31 (20:1 CHCl$_3$/MeOH); [α]$^{23}_D$=−61.8° (c 0.66, CHCl$_3$); $^1$H NMR (CDCl$_3$, 300 MHz) δ 7.2–7.4 (m, 5H), 4.68 (dd, J=4.4, 6.2 Hz, 1H, H$_1$), 4.59 (dd, J=4.2, 6.2 Hz, 1H, H$_2$), 4.52 (ABq, J=11.9 Hz, Δν=14.9 Hz, 2H), 3.96 (m, 1H, H$_8$), 3.60 (m, 1H, H$_{10}$), 3.47 (dt, J=4.6, 9.1 Hz, 1H, H$_{10}'$), 3.12 (d, J=10.6 Hz, 1H, H$_{3eq}$), 3.03 (d, J=3.7 Hz, 1H, H$_{OH}$), 2.79 (ddd, J=2.7, 4.1 10.8 Hz, 1H, H$_{5eq}$), 2.0=2.2 (m, 4H, H$_{3ax,5ax,7,9}$), 1.8–1.9 (m, 2H, H$_6$), 1.60 (m, 1H, H$_{8a}$), 1.51(s,3H), 1.44 (m, 1H, H$_9$), 1.33 (s, 3H); $^{13}$C NMR (CDCl$_3$, 75 MHz) δ 137.9, 128.4, 127.8, 127.7, 111.1, 79.6, 78.2, 73.2, 70.0, 69.0, 67.6, 59.9, 46.7, 36.6, 30.2, 27.8, 26.8, 26.0, 24.7; IR (neat) 3465 (br m), 2933 (s), 2856 (m), 2789 (m), 1372 (m) cm$^{-1}$; MS (CI, NH$_3$) m/z (rel intensity) 348 [(M+H)$^+$, 100], 256 (15), 106 (17); HRMS (CI, NH$_3$) calcd for C$_{20}$H$_{29}$NO$_4$H [(M+H)$^+$] 348.2175; found 348.2172; Anal. Calcd for C$_{20}$H$_{29}$NO$_4$: C, 69.14; H, 8.41; N, 4.03. Found: C, 68.68; H, 8.29; N, 4.04.

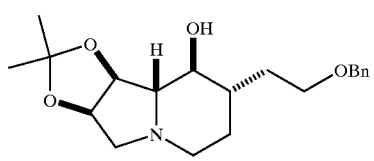

55

(1S,2R,7R,8S,8aS)-7-[2-(Benzyloxy)ethyl]-8-hydroyx-1,2-O-isopropylidenedioxyindolizidine (55) Reduction of the lactam 49 (50 mg, 0.14 mmol) was carried out with borane-methyl sulfide complex. Chromatography (50:50:1 to 25:50:1 hex/EtOAc/MeOH gradient) provided 47 mg (99%) of the indolizidine 55 as a colorless oil. $R_f$=-0.36 (20:1 CHCl$_3$/MeOH); $[\alpha]^{23}_D$=-20.4° (c 0.78, CHCl$_3$); $^1$H NMR (CDCl$_3$, 300 MHz) δ 7.2–7.4 (m, 5H), 4.71 (m, 1H, H$_2$), 4.54 (ABq, J=12.2 Hz, Δv=34.5 Hz, 2H), 4.51 (dd, J=5.8, 7.4 Hz, 1H, H$_1$), 4.11 (m, 1H, H$_{OH}$), 3.61 (ddd, J=4.0, 5.4, 9.5 Hz, 1H, H$_{10}$), 3.51 (td, J=3.2, 9.4 Hz, 1H, H$_{10}$), 3.36 (dd, J=6.3, 9.1 Hz, 1H, H$_{3eq}$), 3.16 (td, J=2.8, 9.1 Hz, 1H, H$_8$), 2.86 (ddd, J=2.2, 4.3, 9.2 Hz, 1H, H$_{5eq}$), 2.38 (dd, J=5.5, 9.2 Hz, 1H, H$_{3ax}$), 2.19 (td, J=3.0, 11.5 Hz, 1H, H$_{5ax}$), 2.06 (dd, J=5.8, 9.1 Hz, 1H, H$_{8a}$), 1.83 (m, 1H, H$_9$), 1.58–1.68 (m, 2H, H$_{6,9}$), 1.54 (s, 3H), 1.35–1.52 (m, 2H, H$_{6,7}$), 1.34 (s, 3H); $^{13}$C NMR (CDCl$_3$, 90 MHz) δ 137.5, 128.4, 127.8, 114.3, 83.6, 77.8, 75.3, 74.0, 73.1, 69.0, 59.7, 51.1, 43.2, 34.2, 31.4, 27.1, 24.9; IR (neat) 3432 (br m), 2855 (m), 1372 (m) cm$^{-1}$; MS (CI, NH$_3$) m/z (rel intensity) 348 [(M+H)$^+$, 100], 256 (16); HRMS (CI, NH$_3$) calcd for C$_{20}$H$_{29}$NO$_4$H [(M+H)$^+$] 348.2175; found 348.2159; Anal. Calcd for C$_{20}$H$_{29}$NO$_4$: C, 69.14; H, 8.41; N, 4.03. Found: C, 68.85; H, 8.38; N, 3.95.

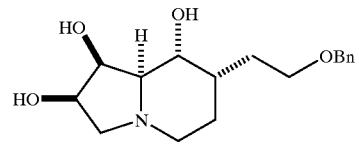

305

(1S,2R,7S,8R,8aR)-7-[2-(Benzyloxy)ethyl]-1,2,8-trihydroxyindolizidine [(7S)-7-(2-Benzyloxyethyl) swainsonine] (53). The acetonide of the indolizidine 51 (65 mg, 0.19 mmol) was hydrolyzed with 6 N HCl in THF. Chromatography (75:25:1 EtOAc/EtOH/Aq. NH$_4$OH) provided 44 mg (80%) of the title compound as a white solid. $R_f$=0.25 (50:25:1 EtOAc/EtOH/Aq. NH$_4$OH); $[\alpha]^{23}_D$=-59.0° (c, 0.95, CH$_3$OH); $^1$H NMR (CD$_3$OD, 360 MHz) δ 7.2–7.4 (m, 5H), 4.50 (ABq, J=11.8 Hz, Δv=15.8 Hz, 2H), 4.21 (m, 1H, H$_2$), 4.13 (dd, J=3.6, 6.0 Hz, 1H, H$_1$), 3.97 (dd, J=5.2, 9.9 Hz, 1H, H$_8$), 3.56 (t, J=6.6 Hz, 2H, H$_{10}$), 2.88 (dd, J=1.9, 10.4 Hz, 1H, H$_3$), 2.69 (dt, J=3.3, 11.6 Hz, 1H, H$_5$), 2.45 (dd, J=7.5, 10.4 Hz, 1H, H$_3$), 2.1 (m, 2H, H$_5$ and H$_7$), 1.98 (m, 2H, H$_6$), 1.52 (m, 1H, H$_9$); $^{13}$C NMR (CD$_3$OD, 90 MHz) δ 139.9, 129.5, 129.0, 128.8, 74.0, 71.1, 70.9, 70.1, 69.4, 68.7, 63.1, 48.0, 36.9, 28.7, 26.0; IR (neat) 3380 (br s), 2942 (s), 2879 (m), 2819 (m), 1097 (s) cm$^{-1}$; MS (CI, NH$_3$) m/z (rel intensity) 308 [(M+H)$^+$, 100], 216 (33), 156 (14), 91 (19); HRMS (CI, CH$_4$ and NH$_3$) calcd for C$_{17}$H$_{25}$NO$_4$H [(M+H)$^+$] 308.1862; found 308.1859.

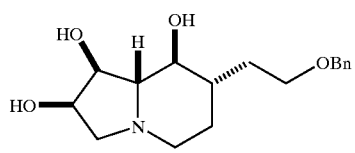

57

(1S,2R,7S,8S,8aS)-7-[2-(Benzyloxy)ethyl]-1,2,8-trihydroxyindolizidine [(7S)-7-(2-Benzyloxyethyl)-8,8a-diepiswainsonine] (57). The acetonide of the indolizidine 55 (25 mg, 0.07 mmol) was hydrolyzed with 6 N HCl in THF. Recrystallization from EtOAc provided 15 mg (68%) of the title compound. $R_f$=0.34 (50:25:1 EtOAc/EtOH/Aq. NH$_4$OH); mp 100° C.; $^1$H NMR (CD$_3$OH, 360 MHz) δ 7.2–7.4 (m, 5H), 4.50 (ABq, J=11.8 Hz, Δv=19.6 Hz, 2H), 4.10 (dd, J=6.6, 13.6 Hz, 1H, H$_2$), 3.82 (t, J=7.4 Hz, 1H, H$_1$), 3.58 (m, 2H, H$_{10}$), 3.35 (dd, J=6.7, 9.6 Hz, 1H, H$_3$), 3.09 (t, J=9.2 Hz, 1H, H$_8$), 2.89 (ddd, J=2.1, 4.2, 11.0 Hz, 1H, H$_5$), 2.17 (m, 2H, H$_3$ and H$_9$), 2.08 (td, J=2.8;12.0 Hz, 1H, H$_5$), 1.89 (dd, J=7.7, 9.0 Hz, 1H, H$_{8a}$), 1.79 (m, 1H, H$_6$), 1.42 (m, 2H, H$_7$ and H$_9$), 1.29 (m, 1H, H$_6$); $^{13}$C NMR (CD$_3$OD, 90 MHz) δ 139.9, 129.5, 129.1, 128.8, 76.9, 75.5, 74.5, 74.0, 69.7, 69.0, 62.0, 52.9, 42.7, 33.1, 31.3; IR (neat) 3350 (br s), 2926 (m), 2800 (m), 1098 (s) cm$^{-1}$; MS (CI, NH$_3$) m/z (rel intensity) 308 [(M+H)$^+$, 100], 290 (21), 216 (43), 156 (17), 91 (22); HRMS (CI, CH$_4$ and NH$_3$) calcd for C$_{17}$H$_{25}$NO$_4$H [(M+H)$^+$] 308.1862; found 308.1869.

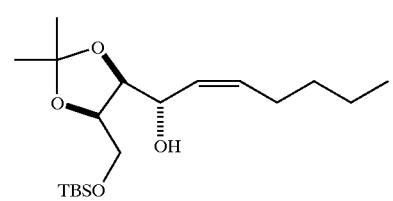

58

(Z)-(2R,3S,4S)-1-tert-Butyldimethylsilyloxy-4-hydroxy-2,3-O-isopropylidenedioxy-5-decene (58). Palladium on calcium carbonate, poisoned with lead (Lindlar's catalyst, 130 mg), and quinoline (250 mg, 1.07 mmol), were added to solution of the diol 35 (1.17 g, 4.83 mmol) in EtOAc (22 mL). The flask was evacuated (aspirator) and purged with hydrogen three times, and the resulting heterogeneous mixture was stirred under a balloon of hydrogen. After 2 h, the hydrogen was evacuated, and the mixture was filtered through Celite, rinsing with EtOAc. The filtrate was diluted with EtOAc (50 mL) and washed with 1 M HCl (2×25 mL), followed by saturated NaHCO$_3$ (25 mL) and brine (25 mL). The organic layer was then dried (MgSO$_4$), and concentrated to give 1.06 g (90% crude) of a pale yellow oil that was used without further purification.

The crude oil was dissolved in THF/DMF (2:1, 30 mL) and the solution was cooled to 0° C. tert-Butyldimethylsilyl chloride (0.73 g, 4.83 mmol) and imidazole (0.82 g, 13.9 mmol) were added, and the solution was stirred at 0° C. for 2 h. The mixture was then diluted with ether (100 mL), and washed with 1 M HCl (2×50 mL), sat. NaHCO$_3$ (50 mL), and brine (50 mL). The organic layer was dried (MgSO$_4$), and concentrated. Chromatography (15:1 hex/EtOAc) provided 1.40 g (68% from the lactone) of the (Z)-allylic alcohol 58 as a colorless oil. $R_f$=0.18 (15:1 hex/EtOAc); $[\alpha]^{23}_D$=+15.9° (c 0.80, CHCl$_3$); $^1$H NMR (CDCl$_3$, 300 MHz) δ 5.69 (dt, J=7.4, 10.9 Hz, 1H), 5.48 (m, 1H), 4.61 (td, J=3.1, 8.8 Hz, 1H), 4.26 (ddd, J=3.6, 5.6, 9.5 Hz, 1H), 4.11 (dd, J=5.6, 8.9 Hz, 1H), 4.00 (d, J=3.1 Hz, 1H), 3.86 (t, J=10.2 Hz, 1H), 3.67 (dd, J=3.6, 10.5 Hz, 1H), 2.14 (m, 2H), 1.37 (s, 3H), 1.32 (s, 3H), 1.3–1.5 (m, 4H), 0.90 (m, 12H), 0.15 (s, 3H), 0.14 (s, 3H); $^{13}$C NMR (CDCl$_3$ 75 MHz) δ 134.6, 128.8, 108.3, 80.6, 77.2, 65.3, 62.1, 31.8, 27.9, 25.9, 25.3, 22.4, 18.3, 14.0, −5.5; IR (neat) 3470 (br m), 2931 (s), 1472 (m), 1380 (m) cm$^{-1}$; MS (CI, CH$_4$ and NH$_3$) m/z (rel intensity) 376 [(M+NH$_4$)$^+$, 19], 359 [(M+H)$^+$, 5], 341 (56), 283 (100), 167 (51), 151 (49); HRMS (CI, NH$_3$) calcd for C$_{19}$H$_{38}$O$_4$SiH [(M+H)$^+$] 359.2618, found 359.2634; Anal. Calcd for C$_{19}$H$_{38}$O$_4$Si: C, 63.64; H, 10.68. Found: C, 63.50; H, 10.47.

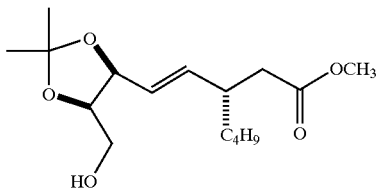

61

Methyl E-(3S,6S,7R)-3-Butyl-8-hydroxy-6,7-O-isopropylidenedioxy-4-octenoate (61). Trimethyl orthoacctate (2.18 g, 18.2 mmol) and propionic acid (54 mg, 0.73 mmol) were added to a solution of the (Z)-allylic alcohol 58 (1.40 g, 3.63 mmol) in toluene (18 mL). The flask was fitted with a distillation head, and the mixture was heated at reflux, distilling off methanol as it formed. GC was used to monitor the disappearance of starting material (t$_R$=5.2 min) and the appearance of product (t$_R$=7.1 min). After 6 h, the mixture was cooled to room temperature and concentrated to give 1.49 g of the desired E-γ,δ-unsaturated ester as a pale yellow oil that was used without further purification. None of the Z-alkenyl isomer was detected by $^1$H or $^{13}$C NMR. [Purification of a small sample by chromatography (15:1 hex/EtOAc) provided an analytically pure sample of methyl (E)-(3S,6S,7R)-3-butyl-8-tert-butyldimethylsilyloxy-6,7-O-isopropylidene-6,7-dihydroxy-4-octenoate. R$_f$=0.22 (15:1 hex/EtOAc); [α]$^{23}$$_D$=0.4° (c 1.35, CHCl$_3$); $^1$H NMR (CDCl$_3$, 300 MHz) δ8.59 (dd, J=7.5, 15.5 Hz, 1H), 5.50 (dd, J=6.8, 15.5 Hz, 1H), 4.54 (t, J=6.6 Hz, 1H), 4.14 (dd, J=5.9, 11.7 Hz, 1H), 3.63 (s, 3H), 3.60 (m, 2H), 2.52 (m, 1H), 2.36 (dd, J=6.6, 15.0 Hz, 1H), 2.30 (dd, J=7.7, 15.0 Hz, 1H), 1.47 (s, 3H), (1.35 (s, 3H), 1.2–1.4 (m, 6H), 0.90 (m, 12H), 0.07 (s, 6H), $^{13}$C NMR (CDCl$_3$, 90 MHz) δ172.6, 136.8, 126.2, 108.4, 79.0, 78.3, 62.8, 51.3, 39.9, 39.0, 34.2, 29.3, 27.9, 26.0, 25.5, 22.6, 18.4, 13.9, −5.2; IR (neat) 2930 (s), 2858 (s), 1742 (s) cm$^{-1}$; MS (CI, CH$_4$ and NH$_3$) m/z (rel intensity) 432 [(M+NH$_4$)$^+$, 25], 374 (81), 357 (100), 327 (45), 207 (56); HRMS (CI, NH$_3$) calcd for C$_{22}$H$_{42}$O$_5$SiNH$_4$ [(M+ NH$_4$)$^+$]432.3145, found 423.3135; Anal. Calcd for C$_{22}$H$_{42}$O$_5$Si: C, 63.73; H, 10.21. Found: C, 63.76; H, 9.97.]

The crude γ,δ-unsaturated ester was dissolved in THF (18 mL, tetra-n-butylammonium fluoride (4.0 mL of a 1 M soln. in THF, 4.0 mmol) was added, and the resulting mixture was stirred at room temperature. After 1 h, the mixture was diluted ether (100 mL) and washed with water (50 mL) and brine (50 mL), then dried (MgSO$_4$) and concentrated. Chromatography (4:1 to 3:1 hex/EtOAc) provided 0.78 g (75% from 58) of the title compound as a colorless oil. The C(3) stereochemistry of 61 was derived from analysis of the most favorable transition state for the Claisen rearrangement R$_f$=0.28 (2:1 hex/EtOAc); [α]$^{23}$$_D$=+26.9° (c 0.52, CHCl$_3$); $^1$H NMR (CDCl$_3$, 300 MHz) δ5.66 (dd, J=7.9, 15.5 Hz, 1H), 5.52 (dd, J=7.1, 15.5 Hz, 1H), 4.64 (t, J=6.8 Hz, 1H), 4.21 (dd, J=5.9, 12.3 Hz, 1H), 3.66 (s, 3H), 3.52 (t, J=5.9 Hz, 2H), 2.54 (m, 1H), 2.41 (dd, J=5.7, 15.2 Hz, 1H), 2.33 (dd, J=8.5, 15.2 Hz, 1H), 2.11 (t, J=6.2 Hz, 1H), 1.49 (s, 3H), 1.38 (s, 3H), 1.15–1.45 (m, 6H), 0.89 (t, J=6.9 Hz, 3H); $^{13}$C NMR (CDCl$_3$, 75 MHz) δ172.9, 137.1, 125.2, 108.5, 78.4, 77.7, 62.0, 51.5, 39.6, 38.9, 34.3, 29.3, 25.3, 22.6, 14.0; IR (neat) 3480 (br s), 2931 (s), 1737 (s) cm$^{-1}$; MS (CI, and CH$_4$ and NH$_3$) m/z (rel intensity) 318 [(M+NH$_4$)$^+$, 21], 243 (49), 230 (100), 207 (39); HRMS (CI, NH$_3$) calcd for C$_{16}$H$_{28}$O$_5$NH$_4$ [(M+NH$_4$)$^+$]318.2280, found 318.2289; Anal. Calcd for C$_{16}$H$_{28}$O$_5$: C, 63.97; H, 9.40. Found: C, 63.43; H, 9.23.

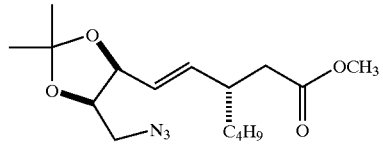

63

Methyl (E)-(3S,6S,7R)-8-Azido-3-butyl-6,7-O-isopropylidenedioxy-4-octenoate (63). Hydrazoic acid (6.5 mL of a 1.2 M solution in benzene, 7.7 mmol) was added to a solution of the alcohol 61 (0.78 g, 2.6 mmol) and triphenylphosphine (1.35 g, 5.2 mmol) in benzene (13 mL). The mixture was cooled to 5° C., and diethyl azodicarboxylate (0.85 mL, 5.2 mmol) was added in a dropwise fashion. The solution was then allowed to warm to room temperature. After 2 h, TLC indicated that starting material was still present. More hydrazoic acid solution (2.2 mL, 2.6 mmol), triphenylphosphine (0.51 g, 1.9 mmol), and DEAD (0.32 mL, 1.9 mmol) was added, and the mixture was allowed to stir at room temperature for another 1 h. The mixture was then poured into hexanes (100 mL), resulting in the formation of a white precipitate. The mixture was filtered and the filtrate was concentrated. Chromatography (15:1 to 10:1 hexane/BtOAc) provided 0.645 g (77%) of the azide 63 as a colorless oil. R$_f$=0.23 (8:1 hex/EtOAc); [α]$^{23}$$_D$=+56.3° (c 0.86, CHCl$_3$); $^1$H NMR (CDCl$_3$, 300 MHz) δ5.68 (dd, J=8.2, 15.5 Hz, 1H), 5.44 (dd, J=7.4, 15.4 Hz, 1H), 4.62 (t, J=6.9 Hz, 1H), 4.26 (ddd, J=4.2, 6.6, 7.8 Hz, 1H), 3.66 (s, 3H), 3.27 (dd, J=7.8, 12.8 Hz), 1H), 3.13 (dd, J=4.2, 12.8 Hz, 1H), 2.57 (m, 1H), 2.39 (dd, J=6.1, 15.0 Hz, 1H), 2.32 (dd, J=8.1, 15.0 Hz, 1H), 1.52 (s, 3H), 1.39 (s, 3H), 1.15–1.45 (m, 6H), 0.89 (t, J=6.8 Hz, 3H); $^{13}$C NMR (CDCl$_3$, 75 MHz) δ172.5, 137.9, 124.7, 109.1, 77.8, 77.0, 51.7, 51.4, 39.6, 38.9, 34.2, 29.3, 27.9, 25.4, 22.6, 14.0; IR (neat) 2932 (m), 2102 (s), 1738 (s) cm$^{-1}$; MS (CI, NH$_3$) m/z (rel intensity) 343 [(M+NH$_4$)$^+$, 9], 298 (97), 268 (100), 240 (20); HRMS (CI, NH$_3$) calcd for C$_{16}$H$_{27}$N$_3$O$_4$NH$_4$ [(M+NH$_4$)$^+$] 343.2345; found 343.2331; Anal. Calcd for C$_{16}$H$_{27}$N$_3$O$_4$: C, 59.06; H, 8.36; N, 12.91. Found: C, 59.43; H, 8.35; N, 12.86.

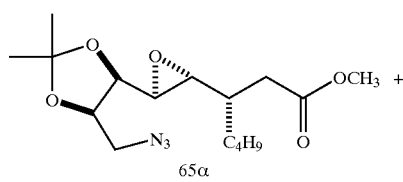

65α

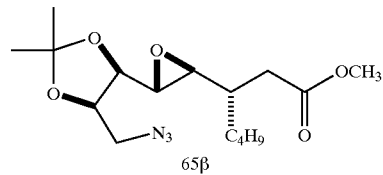

65β

Methyl (3S,4R,5S,6R,7R)-8-Azido-3-butyl-4,5-epoxy-6,7-O-isopropylidenedioxyoctanoate (65α) and Methyl (3S, 4S,5R,6R,7R)-8-Azido-3-butyl-4,5-epoxy-6,7-O-isopropylidenedioxyoctanoate (65β). m-Chloroperbenzoic acid (1.05 g, technical grade, 0.84 g pure, 4.9 mmol) was added to a cooled (0° C.) solution of the azide 63 (0.63 g, 1.9 mmol) in CH$_2$Cl$_2$ (10 mL). After 24 h, the mixture was diluted with ether (50 mL) and washed with 1 M NaOH (2×25 mL). The aqueous layers were back-extracted with ether (2×25 mL), and the combined organic layers were washed with saturated NaHCO$_3$ (50 mL) and brine (25 mL), then dried (MgSO$_4$) filtered, and concentrated to provide 0.64 g (96% crude) of a mixture (2:1 by $^1$H NMR integration) of diastereomeric epoxides 65α and 65β that were used without further purification. Purification of a small sample by chromatography (20:1 to 15:1 hex/EtOAc gradient) provided analytically pure samples of the epoxides 65α and 65β.

Data for 65α: R$_f$=0.29 [8.1 hex/EtOAc (2 elutions)]; [α]$^{21}_D$=+57.7° (c 0.65, CHCl$_3$); $^1$H NMR (CDCl$_3$, 360 MHz) δ4.34 (td, J=4.3, 6.7 Hz, 1H), 3.68 (s, 3H), 3.65 (dd, J=6.4, 8.1 Hz, 1H), 3.59 (dd, J=4.3, 13.1 Hz, 1H), 3.53 (dd, J=6.9, 13.1 Hz, 1H), 2.86 (dd, J=2.0, 8.2 Hz, 1H), 2.74 (dd, J=2.0, 7.7 Hz, 1H), 2.39 (dd, J=6.5, 15.6 Hz, 1H), 2.31 (dd, J=7.6, 15.6 Hz, 1H), 1.85 (m, 1H), 1.52 (s, 3H), 1.37 (s, 3H), 1.25–1.55 (m, 6H), 0.90 (t, J=6.9 Hz, 3H): $^{13}$C NMR (CDCl$_3$, 90 MHz) δ172.2, 109.5, 77.3, 76.3, 60.8, 53.7, 51.3, 50.1, 36.8, 35.3, 31.8, 28.4, 27.3, 24.7, 22.4, 13.6; IR (neat) 2934 (m), 2102 (s), 1738 (s) cm$^{-1}$; MS (Cl, NH$_3$) m/z (rel intensity) 359 [(M+NH$_4$)$^+$, 7], 342 [(M+H)$^+$, 73], 314 (100), 256 (38), 142 (39); HRMS (Cl, NH$_3$) calcd for C$_{16}$H$_{27}$N$_3$O$_5$H [(M+H$^+$]342.2029; found 342.2041; Anal. Calcd for C$_{16}$H$_{27}$N$_3$O$_5$: C, 56.29; H, 7.97; N, 12.31. Found: C, 56.63; H, 7.96; N, 12.38.

Data for 65β; R$_f$=0.23 [8:1 hex/EtOAc (2 elutions)]; [α]$^{23}_D$=+2.2° (c 0.45, CHCl$_3$); $^1$H NMR (CDCl$_3$, 360 MHz) δ4.36 (td, J=5.2, 6.9 Hz, 1H), 4.10 (dd, J=3.9, 6.6 Hz), 1H), 3.68 (s, 3H), 3.58 (dd, J=7.1, 12.7 Hz, 1H), 3.47 (dd, J=5.2, 12.7 Hz, 1H), 2.88 (m, 2H), 2.45 (dd, J=6.5, 15.5 Hz, 1H), 2.34 (dd, J=6.7, 15.5 Hz, 1H), 1.86 (q, J=6.7 Hz, 1H), 1.48 (s, 3H), 1.35 (s, 3H), 1.25–1.55 (m, 6H), 0.90 (t, J=6.9 Hz, 3H); $^{13}$C NMR (CDCl$_3$, 90 MHz) δ172.9, 109.7, 76.6, 76.0, 57.1, 55.7, 51.6, 51.1, 37.2, 35.9, 31.0, 29.2, 27.0, 25.2, 22.7, 13.9; IR (neat) 2934 (m), 2103 (s), 1738 (s) cm$^{-1}$; MS (Cl, NH$_3$) m/z (rel intensity) 359 [(M+NH$_4$)$^+$, 31], 342 [(M+H)$^+$, 46], 314 (100), 282, (48), 158 (90), 142 (83); HRMS (Cl, CH$_4$ and NH$_3$) calcd for C$_{16}$H$_{27}$N$_3$O$_5$H) [(M+H)$^+$] 342.2029; found 342.2034; Anal. Calcd. for C$_{16}$H$_{27}$N$_3$O$_5$; C, 56.29; H, 7.97; N, 12.31. Found: C, 56.55; H, 7.99; N, 11.92.

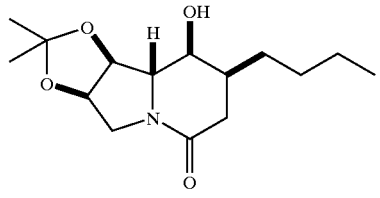

68

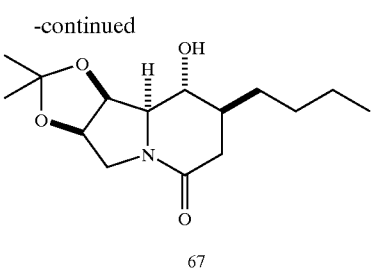

67

(1S,2R,7S,8S,8aS)-7-Butyl-8-hydroxy-1,2-O-isopropylidenedioxyindolizidin-5-one (68) and (1S,2R,7S, 8R,8aR)-7-Butyl-8-hydroxy-1,2-O-isopropylidenedioxy-indolizindin-5-one (67). Palladium hydroxide on carbon (90 mg) was added to a solution of the mixture of epoxides 65αβ (2:1, 580 mg, 1.7 mmol) in MeOH/EtOAc (1:1, 25 mL). The flask was evacuated (aspirator) and purged with hydrogen three times, and the resulting heterogeneous mixture was stirred under a balloon of hydrogen. After 3 h, the hydrogen was evacuated, the mixture was filtered, and the filtrate was concentrated. The residue was dissolved in MeOH (25 mL), sodium methoxide (46 mg, 0.9 mmol) was added, and the mixture was warmed to reflux. Reaction progress was monitored by IR for the disappearance of the ester and lactone carbonyl stretches at 1735 cm$^{-1}$ and 1775 cm$^{-1}$ and appearance of the lactam carbonyl stretch at 1630 cm$^{-1}$. After 48 h, the mixture was cooled to room temperature and concentrated. The residue was dissolved in CH$_2$Cl$_2$/MeOH (20:1, 10 mL), Florisil (1 g) was added, and the mixture was stirred for 15 min. The suspension was then filtered through Celite, and the filtrate was concentrated. Chromatography (100:1 to 50:1 CH$_2$Cl$_2$/MeOH) provided 290 mg (60%) of a mixture (1:2.4 by $^1$H NMR integration) of the lactams 68 and 67. R$_f$=0.31 (20:1 CHCl$_3$/MeOH); $^1$H NMR (CDCl$_3$; 300 MHz, α indicates major isomer and β indicates minor isomer, α/β ratio=2.4:1) δ4.81 (dd, J=4.5, 6.0 Hz, 1Hα), 4.75 (t, J=6.0 Hz, 1Hα), 4.72 (td, J=2.9, 6.6 Hz, 1Hβ), 4.40 (t, J=6.8 Hz, 1Hβ), 4.31 (dd, J=6.6, 13.5 Hz, 1Hβ), 4.17 (d, J=13.6 Hz, 1Hα), 3.90 (dt, J=3.9, 7.6 Hz, 1Hβ), 3.75 (ddd, J=5.0, 8.9, 10.3 Hz, 1Hα), 3.40 (t, J=7.1 Hz, 1Hβ), 3.32 (dd, J=4.2, 8.8 Hz, 1Hα), 3.31 (dd, J=2.9, 13.5 Hz, 1Hβ), 3.34 (dd, J=4.7, 13.7 Hz, 1Hα), 2.61 (m, 2Hα=1Hβ), 2.48 (dd, J=4.5, 17.5 Hz, 1Hβ), 2.31 (dd, J=5.2, 17.5 Hz, 1Hβ), 2.03 (dd, J=11.9, 17.1 Hz, 1Hα), 1.7–1.9 (m, 2Hα+2Hβ), 1.57 (s, 3Hβ), 1.42 (s, 3Hα), 1.37 (s, 3Hβ), 1.34 (s, 3Hα), 1.1–1.5 (m, 6Hα+6Hβ), 0.90 (t, J=6.9 Hz, 3Hα+3Hβ); $^{13}$C NMR (CDCl$_3$, 90 MHz, α indicates major isomer and β indicates minor isomer) δ168.2, 112.1, 83.6 (β), 79.8 (α), 77.7 (α), 76.9 (β), 70.8 (β), 69.4 (α), 65.9 (α), 64.9 (β), 50.5 (α), 50.0 (β), 39.4 (α), 37.6 (β), 36.0 (α), 34.3 (β), 31.0 (α), 29.6 (β), 28.2 (α), 27.7 (β), 27.1 (β), 26.5 (α), 25.5 (β), 24.8 (α), 22.8 (α), 14.0; IR (neat) 3360 (br m), 2934 (m), 1633 (s) cm$^{-1}$; MS (Cl, NH$_3$) m/z (rel intensity) 284 [(M+H)$^+$, 100], 208 (2); HRMS (Cl, CH$_4$) calcd for C$_{15}$H$_{25}$NO$_4$H [(M+H)$^+$]284.1862; found 284.1875; Anal. Calcd for C$_{15}$H$_{25}$NO$_4$: C, 63.58; H, 8.89; N, 4.94. Found: C, 63.22; H; 8.86; N, 4.91.

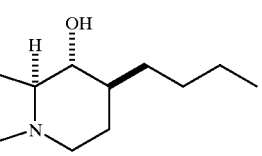

71

72

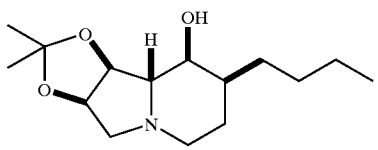

(1S,2R,7S,8R,8aR)-7-Butyl-8-hydroxy-1,2-O-isopropylidenedioxy-indolizidine (71) and (1S,2R,7S,8S,8aS)-7-Butyl-8-hydroxy-1,2-O-isopropylidenedioxyindolizidine (72) Reduction of the mixture of lactams 67 and 68 (2.4:1, 280 mg, 0.99 mmol) was carried out with borane-methyl sulfide complex. Chromatography (100:1 to 50:1 $CH_2Cl_2$/MeOH gradient) provided 1.55 mg (58%) of the indolizidine 71 as a white crystalline solid followed by 59 mg (22%) of the indolizidine 72 as a pale yellow oil. Data for 71 (major): $R_f$=0.35 (20:1 $CHCl_3$/MeOH); $[\alpha]^{23}_D$=−26.4° (c 0.70, $CHCl_3$); mp 96° C.; $^1$H NMR ($CDCl_3$, 300 MHz) δ4.69 (dd, J=4.5, 6.2 Hz, 1H, $H_1$), 4.61 (dd, J=4.2, 6.2 Hz, 1H, $H_2$), 3.48 (td, J=4.7, 9.0 Hz, 1H, $H_8$), 3.13 (d, J=10.7 Hz, 1H, $H_{3eq}$), 3.00 (m, 1H, $H_{5eq}$), 2.13 (d, J=4.6 Hz, 1H, $H_{OH}$), 2.10 (dd, J=4.2, 6.4 Hz, 1H, $H_{3ax}$), 1.75–1.95 (m, 3H), 1.67 (dd, J=4.4, 8.9 Hz, 1H, $H_{8a}$), 1.51 (s, 3H), 1.32 (s, 3H), 1.05–1.45 (m, 7H), 0.90 (t, J=6.9 Hz, 3H, $H_{12}$); $^{13}$C NMR ($CDCl_3$, 75 MHz) δ111.2, 79.3, 78.6, 73.4, 71.4, 59.9, 51.7, 43.0, 31.5, 29.9, 29.0, 26.1, 24.9, 23.1, 14.1; IR (neat) 3290 (br m), 2918 (s), 2858 (m), 2793 (m), 1466 (m) cm$^{-1}$; MS (CI, $NH_3$) m/z (rel intensity) 270 [(M+H)$^+$, 100], 252 (39), 194 (21); HRMS (CI, $NH_3$) calcd for $C_{15}H_{27}NO_3H$ [(M+H)$^+$]270.2069; found 270.2061; Anal. Calcd for $C_{15}H_{27}NO_3$: C,66.88; H, 10.10; N, 5.20. Found C, 66.78; H, 10.35; N, 5.27.

Data for 72 (minor): $R_f$=0.29 (20:1 $CHCl_3$/MeOH); $^1$H NMR ($CDCl_3$, 300 MHz) δ4.70 (td, J=5.1, 6.6 Hz, 1H, $H_2$), 4.41 (dd, J=6.1 7.1 Hz, 1H, $H_1$), 3.63 (dd, J=5.0, 9.6 Hz, 1H, $H_8$), 3.37 (dd, J=6.4, 9.4 Hz, 1H, $H_{3eq}$), 2.62 (ddd, J=2.8, 4.3, 11.3 Hz, 1H$_{5eq}$), 2.43 (dd, J=5.0, 9.4 Hz, 1H, $H_{3ax}$), 2.38 (td, J=3.4, 11.4 Hz, 1H, $H_{5ax}$), 2.23 (dd, J=6.0, 9.7 Hz, 1H, $H_{8a}$), 1.95 (m, 1H, $H_{OH}$), 1.45–1.75 (m, 3H), 1.52 (s, 3H), 1.34 (s, 3H), 1.1–1.45 (m, 5H), 0.91 (t, J=7.1 Hz, 3H, $H_{12}$); $^{13}$C NMR ($CDCl_3$, 75 MHz) δ114.4, 83.5, 77.6, 73.7, 68.3, 59.4, 45.9, 38.6, 30.3, 27.1, 26.8, 24.9, 23.5, 23.0, 14.1; IR (neat) 3465 (br m), 2931 (s), 2869 (m), 2803 (m) 1456 (m), 1372 (m) cm$^{-1}$; MS (CI, $CH_4$ and $NH_3$) m/z (rel intensity) 270 [(M+H)$^+$, 100], 252 (17); HRMS (CI, $CH_4$ and $NH_3$) calcd for $C_{15}H_{27}NO_3H$ [(M+H)$^+$]270.2069; found 270.2061.

75

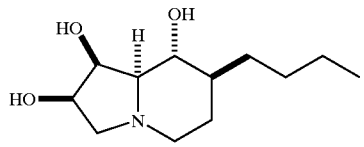

(1S,2R,7S,8S,8aS)-7-Butyl-1,2,8-trihydroxyindolizidine [(7S)-7-Butyl-swainsonine] (75). The acetonide of the indolizidine 71 (110 mg, 0.41 mmol) was hydrolyzed with 6 N HCl in THF. Recrystallization from EtOAc provided 73 mg (78%) of the title compound. $R_f$=0.37 (50:25:1 EtOAc/EtOH/Aq. $NH_4OH$); $[\alpha]^{23}_D$=−22.6° (c 1.05, MeOH); mp 115° C.; $^1$H NMR ($CDCl_3$, 360 MHz) δ 4.25 (m, 2H), 3.4–4.2 (br m, 3H, $D_2O$ exchangeable), 3.48 (t, J=9.3 Hz, 1H), 2.98 (m, 2H), 2.38 (dd, J=6.5, 10.7 Hz, 1H), 1.9 (m, 2H), 1.80 (m, 2H), 1.0–1.45 (m, 7H), 0.90 (t, J=7.0 Hz, 3H); $^{13}$C NMR ($CDCl_3$, 90 MHz) δ73.5, 70.7, 70.2, 69.6, 62.1, 52.1, 42.6, 31.4, 29.3, 29.0, 23.0, 14.1; IR (neat) 3380 (br m), 2949 (s), 2813 (m) cm$^{-1}$; MS (CI, $CH_4$ and $NH_3$) m/z (rel intensity) 230 [(M+H)$^+$, 91], 212 (100), 194 (29), 176 (19); HRMS (CI, $CH_4$ and $NH_3$) calcd for $C_{12}H_{23}NO_3H$ [(M+H)$^+$]230.1756; found 230.1760; Anal. Calcd for $C_{12}H_{23}NO_3$: C, 62.84; H, 10.11; N, 6.11. Found C, 62.49; H, 10.01; N, 6.06.

77

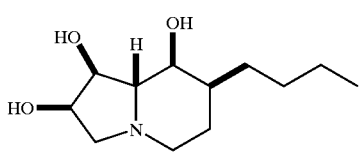

(1S,2R,7S,8S,8aS)-7-Butyl-1,2,8-trihydroxyindolizidine [(7S)-7-Butyl-8,8a-diepiswainsonine](77). The acetonide of the indolizidine 72 (35 mg, 0.13 mmol) was hydrolyzed with 6 N HCl in THF. Chromatography (75:25:1 EtOAc/EtOH/ Aq. $NH_4OH$) provided 24 mg (80%) of the title compound as a pale yellow oil. $R_f$=0.12 (75:25:1 EtOAc/EtOH/Aq. $NH_4OH$); $[\alpha]^{23}_D$=+2.5° (c 0.43, MeOH); mp 120° C.; $^1$H NMR ($CDCl_3$, 360 MHz) δ4.21 (td, J=4.8, 6.7 Hz, 1H), 3.86 (t,J=7.6 Hz, 1H), 3.72 (dd, J=4.9, 9.0 Hz, 1H), 3.46 (dd, J=6.6, 10.2 Hz, 1H), 3.3–3.7 (br m, 3H, $D_2O$ exchangeable), 2.63 (dt, J=3.6, 10.9 Hz, 1H), 2.32 (m, 2H), 2.9 (t, J=8.6 Hz, 1H), 1.89 (m, 1H), 1.72 (m, 1H), 1.60 (m, 2H), 1.15–1.45 (m, 5H), 0.91 (t, J=7.0 Hz, 3H); $^{13}$C NMR ($CDCl_3$, 90 MHz) δ74.8, 74.2, 67.4, 65.5, 61.3, 46.6, 38.3, 30.2, 26.8, 23.9, 23.0, 14.1; IR (neat) 3370 (br s), 2930 (s) 2870 (m), 1124 (m) cm$^{-1}$; MS (CI, $CH_4$ and $NH_3$) m/z (rel intensity) 230 [(M+H)$^+$, 100], 212 (91), 194 (16); HRMS (CI, $CH_4$ and $NH_3$) calcd for $C_{12}H_{23}NO_3H$ [(M+H)$^+$]230.1756; found 230.1766.

59

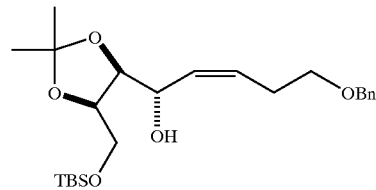

(Z)-(5S,6S,7R)-1-Benzyloxy-8-tert-butyldimethylsilyloxy5-hydroxy-2,3-O-isopropylidenedioxy-3-octene (59). Palladium on calcium carbonate, poisoned with lead (Lindlar's catalyst, 120 mg) and quinoline (97 mg, 0.75 mmol) were added to solution of the diol 36 (1.22 g, 37.5 mmol) in EtOAc (12 mL). The flask was evacuated (aspirator) and purged with hydrogen three times, and the resulting heterogeneous mixture was stirred under a balloon of hydrogen. After 3 h, the hydrogen was evacuated, and the mixture was filtered through Celite, rinsing with EtOAc. The filtrate was diluted with EtOAc (50 mL) and washed with 1 M HCl (2×25 mL), followed by saturated $NaHCO_3$ (25 mL) and brine (25 mL). The organic layer was then dried ($MgSO_4$), and concentrated to give 1.09 g (90% crude) of a pale yellow oil that was used without further purfication. [A small purification was purified by chromatography (2:1 hex/EtOAc) to provide an analytically pure sample of (Z)-(5S,6S,7R)-1-Benzyloxy-2,3-O-isopropylidene-1,2,3,4-tetrahydroxy-3-octene. $R_f$=0.31 (2:1 hex/EtOAc−3 elutions); $[\alpha]^{23}_D$=+26.3° (c 0.85, $CHCl_3$); $^1$H NMR ($CDCl_3$, 300 MHz) δ7.2–7.4 (m, 5H), 5.80 (dd, J=7.1, 11.0 Hz, 1H), 5.72 (m, 1H), 4.51 (m, 3H), 4.33 (ddd, J=4.8, 5.7, 8.3 Hz, 1H), 4.10 (dd, J=5.8, 9.0 Hz, 1), 3.85 (ddd, J=4.5, 8.3, 11.6 Hz, 1H), 3.82 (d, J=1.9 Hz, 1H), 3.72 (ddd, J=4.7, 9.0, 11.6 Hz, 1H), 3.62 (dt, J=4.5, 8.7 Hz, 1H), 3.45 (m, 2H), 2.66 (m, 1H), 2.29 (m, 1H), 1.38 (s, 3H), 1.34 (s, 3H); $^{13}$C NMR (CDCl$_3$, 75 MHz) δ137.1, 132.7, 130.9, 128.5, 128.0, 127.9, 108.3, 79.4, 77.6, 73.5, 68.5, 64.8, 60.9, 28.7, 27.8, 25.3; IR (neat) 3385 (br s), 2985 (m), 2934 (s), 2866 (s), 1370 (m) cm$^{-1}$; MS (CI, NH$_3$) m/z (rel intensity) 340 [(M+NH$_4$)$^+$, 15], 322 ([M$^+$, 89], 305 (100), 282 (77), 247 (60), 106 (62); HRMS (CI, NH$_3$) calcd for C$_{18}$H$_{26}$O$_5$NH$_4$ [(M+NH$_4$)$^+$]340.2124, found 340.2109; Anal. Calcd for C$_{18}$H$_{26}$O$_5$: C, 67.06; H, 8.13, Found: C, 66.91; H, 8.06.]

The crude (Z)-alkenyl diol was dissolved in THF/DMF (2:1, 15 mL) and the solution was cooled to 0° C. tert-Butyldimethylsilyl chloride (0.58 g, 3.8 mmol) and imidazole (0.57 g, 8.3 mmol) were added, and the solution was stirred at 0° C. for 2 h. The mixture was then diluted with ether (100 mL), and washed with 1 M HCl (2×50 mL), sat. NaHCO$_3$ (50 mL), and brine (50 mL). The organic layer was dried (MgSO$_4$) and concentrated. Chromatography (10:1 hex/EtOAc) provided 1.09 g (70% from the lactone) of the (Z)-allylic alcohol 59 as a colorless oil. R$_f$=0.66 (2:1 hex/EtOAc); [α]$^{23}$$_D$=+15.4° (c 0.90, CHCl$_3$); $^1$H NMR (CDCl$_3$, 300 MHz) δ7.2–7.4 (m, 5H), 5.71 (dt, J=7.2, 11.0 Hz, 1H), 5.60 (dd, J=8.1, 11.0 Hz, 1H), 4.61 (td, J=2.8, 8.2 Hz, 1H), 4.51 (s, 2H), 4.25 (ddd, J=3.9, 5.6, 9.2 Hz, 1H), 4.11 (dd, J=5.7, 8.9 Hz, 1H), 4.04 (d, J=2.9 Hz, 1H), 3.87 (t, J=10.0 Hz, 1H), 3.67 (dd, J=3.8, 10.6 Hz, 1H), 3.54 (m, 2H), 2.51 (m, 2H), 1.35 (s, 3H), 1.31 (s, 3H), 0.92 (s, 9H), 0.14 (s, 6H); $^{13}$C NMR (CDCl$_3$, 75 MHz) δ138.3, 131.0, 129.9, 128.2, 127.5, 127.4, 108.3, 80.2, 77.2, 72.9, 69.7, 65.3, 62.0, 28.9, 27.9, 25.8, 25.2, 18.2, −5.5; IR (neat) 3460 (br m), 2933 (s), 2857 (s) 1362 (s) cm$^{-1}$; MS (CI, NH$_3$) m/z (rel intensity) 454 [(M+NH$_4$)$^+$, 3], 437 [(M+H)$^+$, 12], 419 (82) 396 (67), 379 (100), 361 (59), 222 (97); HRMS (CI, NH$_3$) calcd for C$_{24}$H$_{40}$O$_5$H [(M+H)$^+$]437.2723 found 437.2692; Anal. Calcd for C$_{24}$H$_{40}$O$_5$Si: C, 66.02; H, 9.23. Found: C, 65.99; H, 9.05.

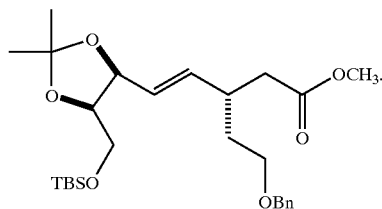

62

Methyl (E)-(3S,6S,7R)-3-[2-(Benzyloxy)ethyl]-1-tert-butyldimethylsilyloxy-6,7-O-isopropylidenedioxy-4-octenoate. Trimethyl orthoacetate (1.40 g, 11.6 mmol) and propionic acid (35 mg, 0.46 mmol) were added to a solution of the (Z)-allylic alcohol 59 (1.01 g, 2.31 mmol) in toluene (10 mL). The flask was fitted with a distillation head and the mixture was heated at reflux, distilling off methanol as it formed. After 16 h, the mixture was cooled to room temperature and concentrated. Chromatography (10:1 to 8:1 hex/EtOAc gradient) provided 0.860 g (75%) of the E-γ,δ-unsaturated ester as a colorless oil. None of the Z-alkenyl isomer was detected by $^1$H or $^{13}$C NMR. The C(3) stereochemistry of the E-γ,δ-unsaturated ester was derived from analysis of the most favorable transition state for the Claisen rearrangement. R$_f$=0.63 (2:1 hex/EtOAc); [α]$^{23}$$_D$=−12.9° (c 1.15, CHCl$_3$); $^1$H NMR (CDCl$_3$, 360 MHz) δ7.2–7.4 (m, 5H), 5.64 (dd, J=8.2, 15.4 Hz, 1H), 5.52 (dd, J=6.7, 15.4 Hz, 1H), 4.55 (t, J=6.7 Hz, 1H), 4.47 (t, J=12.2 Hz, 2H), 4.14 (dd, J=15.9, 12.2 Hz, 1H), 3.64 (s, 3H), 3.58 (d, J=5.8 Hz, 2H), 3.48 (m, 2H), 2.77 (m, 1H), 2.41 (dd, J=6.6, 15.1 Hz, 1H), 2.35 (dd, J=7.6, 15.1 Hz, 1H), 1.78 (m, 1H), 1.62 (m, 1H), 1.46 (s, 3H), 1.35 (s, 3H), 0.89 (s, 9H), 0.06 (s, 6H); $^{13}$C NMR (CDCl$_3$, 90 MHz) δ172.5, 138.4, 135.9, 128.3, 127.5, 127.4, 126.5, 108.4, 78.7, 77.9, 72.8, 67.9, 62.6, 51.4, 39.6, 35.9, 34.1, 27.8, 25.9, 25.3, 18.2, −5.3; IR (neat) 2930 (s) 2856 (s), 1739 (s) cm$^{-1}$; MS (Cl, NH$_3$) m/z (rel intensity) 510 [(M+NH$_4$)$^+$, 100], 435 (37), 327 (26), 195 (76); HRMS (CI, NH$_3$) calcd for C$_{27}$H$_{44}$O$_6$SiNH$_4$ [(M+NH$_4$)$^+$]510.3251, found 510.3271; Anal. Calcd for C$_{27}$H$_{44}$O$_6$Si: C, 65.82; H, 9.00. Found: C, 65.52; H, 8.88.

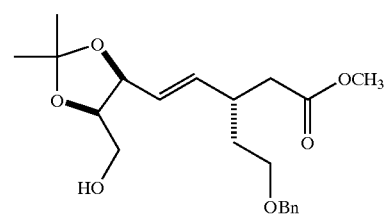

62

Methyl (E)-(3S,6S,7R)-3-[2-Benzyloxy)ethyl]-8-hydroxy-6,7-O-isopropylidenedioxy-4-octenoate (62). Tetra-n-butylammonium fluoride (1.9 mL of a 1 M soln. in THF, 1.9 mmol) was added to a solution of the E-γ,δ-unsaturated ester from above (0.84 g, 1.70 mmol) in THF (9 mL), and the resulting mixture was stirred at room temperature. After 1 h, the mixture was diluted with ether (50 mL), and washed with water (25 mL), and brine (25 mL), then dried (MgSO$_4$), and concentrated. Chromatography (2:1 hex/EtOAc) provided 0.60 g (93%) of the alcohol 62 as a colorless oil. R$_f$=0.10 (2:1 hex/EtOAc); [a]$^{23}$$_D$=+6.3° (c 0.80, CHCl$_3$); $^1$H NMR (CDCl$_3$, 360 MHz) δ7.2–7.4 (m, 5H), 5.66 (dd, J=8.4, 15.5 Hz, 1H), 5.53 (dd, J=6.7, 15.5 Hz, 1H), 4.60 (t, J=6.7 Hz, 1H), 4.47 (ABq, J=12.0 Hz, Δv=14.2 Hz, 2H), 4.18 (dd, J=6.0, 12.1 Hz, 1H), 3.65 (s, 3H), 3.47 (m, 4H), 2.77 (m, 1H), 2.45 (dd, J=5.7, 15.5 Hz, 1H), 2.36 (dd, J=8.5, 15.5 Hz, 1H), 2.15 (dd, J=6.0, 6.7 Hz, 1H), 1.76 (m, 1H), 1.62 (m, 1H), 1.47 (s, 3H), 1.37 (s, 3H); $^{13}$C NMR (CDCl$_3$, 90 MHz) δ172.8, 138.3, 136.1, 128.3, 127.7, 127.6, 125.7, 108.5, 78.2, 77.4, 72.9, 67.7, 61.7, 51.6, 39.3, 36.0, 34.2, 27.8, 25.2; IR (neat) 3488 (m), 2934 (s), 2868 (s), 1736 (s) cm$^{-1}$; MS (CI, NH$_3$) m/z (rel intensity) 396 [(M+NH$_4$)$^+$, 48], 321 (64), 303 (58), 213 (70), 195 (100); HRMS (CI, NH$_3$) calcd for C$_{21}$H$_{30}$O$_6$NH$_4$ [(M+NH$_4$)$^+$]396.2386, found 396.2368.

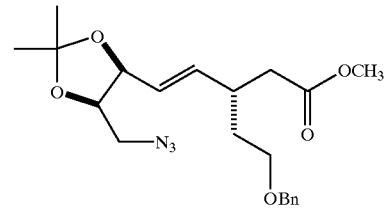

64

Methyl (E)-3S,6S,7R)-8-Azido-3-[2-(benzyloxy)ethyl]-6,7-O-isopropylidenedioxy-4-octenoate (64). Hydrazoic acid (3.6 mL of a 1.2 M solution in benzene, 4.4 mmol) was added to a solution of the alcohol 62 (0.55 g, 1.5 mmol) and triphenylphosphine (0.76 g, 2.9 mmol) in benzene (7.5 mL). The mixture was cooled to 5° C. and diethyl azodicarboxylate (0.48 mL, 2.9 mmol) was added in a dropwide fashion.

The solution was then allowed to warm to room temperature. After 2 h, TLC indicated that starting material was still present. More hydrazoic acid solution (1.2 mL, 1.4 mmol), triphenylphosphine (0.29 g, 1.1 mmol), and DEAD (0.18 mL, 1.1 mmol) were added, and the mixture was allowed to stir at room temperature for another 1 h. The mixture was then poured into hexanes (50 mL), resulting in the formation of a white precipitate. The mixture was filtered, and the filtrate was concentrated. Chromatography (8:1 and 6:1 hexane/EtOAc) provided 0.465 g (80%) of the azide 64 as a colorless oil. $R_f$=0.15 (6:1 hex/EtOAc); $[α]^{23}_D$=+22.3° (c 0.90, $CHCl_3$); $^1H$ NMR ($CDCl_3$, 360 MHz) δ7.2–7.4 (m, 5H), 5.68 (dd, J=8.4, 15.5 Hz, 1H), 5.43 (dd, J=7.2, 15.5 Hz, 1H), 4.58 (t, J=6.9 Hz, 1H), 4.47 (ABq, J=12.0 Hz, Δv=17.2 Hz, 2H), 4.22 (ddd, J=4.2, 6.8, 7.8 Hz, 1H), 3.65 (s, 3H), 3.45 (m, 2H), 3.18 (dd, J=7.9, 12.8 Hz, 1H), 3.05 (dd, J=4.2, 12.8 Hz, 1H), 2.79 (m, 1H), 2.44 (dd, J=6.0, 15.2 Hz, 1H), 2.35 (dd, J=8.2, 15.2 Hz, 1H), 1.77 (m, 1H), 1.63 (m, 1H), 1.51 (s, 3H), 1.37 (s, 3H), $^{13}C$ NMR ($CDCl_3$, 90 MHz) δ172.4, 138.3, 137.1, 128.4, 127.6, 125.1, 109.1, 77.5, 76.9, 72.9, 67.7, 51.5, 39.4, 36.0, 34.2, 27.8, 25.2; IR (neat) 2987 (m), 2934 (m), 2861 (m), 2101 (s), 1738 (s) $cm^{-1}$; MS (CI, $NH_3$) m/z (rel intensity) 421 [$(M+NH_4)^+$, 7], 376 (100), 318 (22); HRMS (CI, $NH_3$) calcd for $C_{21}H_{29}N_3O_5NH_4$[$(M+NH_4)^+$]421.2451; found 421.2462; Anal. Calcd for $C_{21}H_{29}N_3O_5$: C, 62.51; H, 7.24; N, 10.41. Found: C, 62.47; H, 7.25; N, 10.46.

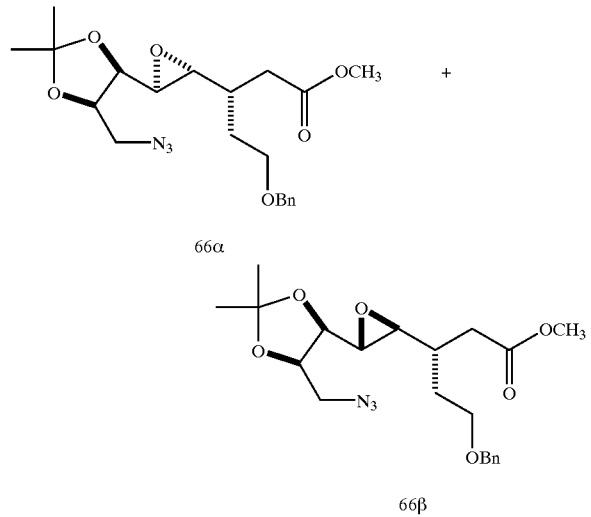

66α

66β

Methyl (3S,4R,5S,6R,7R)-8-Azido-3-[2-(benzyloxy)ethyl]-4,5-epoxy-6,7-O-isopropylidenedioxyoctanoate (66α) and Methyl (3S,4S,5R,6R,7R)-8-Azido-3-[2-(benzyloxy)ethyl]-4,5-epoxy-6,7-O-isopropylidenedioxyoctanoate (66β), m-Chloroperbenzoic acid (0.56 g, technical grade, 0.45 g pure, 3.1 mmol) was added to a cooled (0° C.) solution of the azide 64 (0.42 g, 1.0 mmol) in $CH_2Cl_2$ (5 mL). After 24 h, the mixture was diluted with ether (50 mL) and washed with 1 M NaOH (2×25 mL). The aqueous layers were back-extracted with ether (2×25 mL), and the combined organic layers were washed with saturated $NaHCO_3$ (25 mL) and brine (25 mL), then dried ($MgSO_4$), and concentrated. Chromatography (6:1 hex/EtOAc) provided 325 mg (75%) of a mixture (1.7:1 by $^1H$ NMR integration) of epoxides 66α and 66β. Data for 66α/β: $R_f$=0.28 (4:1 hex/EtOAc); $^1H$ NMR ($CDCl_3$, 360 MHz) major isomer(α) δ7.2–7.4 (m, 5H), 4.50 (s, 2H), 4.34 (td, J=4.4, 6.7 Hz, 1H), 3.67 (s, 3H), 3.66 (dd, J=6.4, 7.9 Hz, 1H), 3.56 (m, 4H), 2.83 (m, 2H), 2.46 (dd, J=6.3, 15.8 Hz, 1H), 2.37 (dd, J=7.7, 15.8 Hz, 1H), 2.02 (m, 1H), 1.7–1.9 (m, 2H), 1.50 (s, 3H), 1.34 (s, 3H); minor isomer (β) δ7.2–7.4 (m, 5H), 4.47 (ABq, J=12.2 Hz, Δv=19.6 Hz, 2H), 4.19 (td, J=5.1, 6.8 Hz, 1H), 3.87 (dd, J=4.2, 6.7 Hz, 1H), 3.66 , (s, 3H), 3.52 (m, 3H), 3.39 (dd, J=5.0, 12.7 Hz, 1H), 2.90 (dd, J=2.2, 7.5 Hz, 1H), 2.80 (dd, J=2.2, 4.2 Hz, 1H),2.50 (dd, J=6.2, 15.6 Hz, 1H), 2.39 (dd, J=7.0, 15.6 Hz, 1H), 2.01 (m, 1H), 1.77 (m, 2H), 1.44 (s, 3H), 1.35 (s, 3H); $^{13}C$ NMR ($CDCl_3$, 90 MHz) major isomer (α)δ172.1, 138.3, 128.2, 127.5, 127.4, 109.8, 77.5, 76.6, 73.0, 67.9, 60.8, 54.2, 51.6, 50.6, 35.7, 34.9, 32.2, 27.6, 25.1; minor isomer (β) δ172.5, 138.1, 128.3, 127.8, 127.7, 109.6, 76.0, 75.9, 73.1, 67.7, 57.0, 55.8, 51.6, 51.2, 35.9, 35.2, 31.1, 27.1, 25.2; IR (neat) 2988 (m), 2937 (m), 2863 (m), 2102 (s), 1738 (s) $cm^{-1}$; MS (CI, $NH_3$) m/z (rel intensity) 437 [$(M+NH_4)^+$, 28], 392 (76), 360 (57), 142 (100), 108 (54); HRMS (CI, $NH_3$) calcd for $C_{21}H_{29}N_3O_6NH_4$ [$(M+NH_4)^+$]437.2400; found 437.2397; Anal. Calcd for $C_{21}H_{29}N_3O_6$; C, 60.13; H, 6.97; N, 10.02 Found: C, 60.30; H, 7.07; N, 10.00.

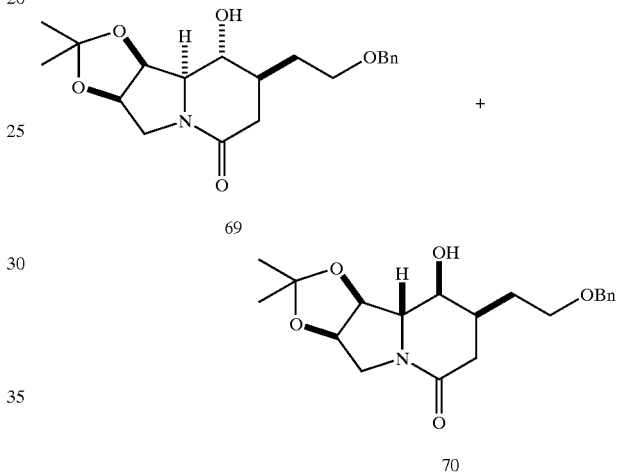

69

70

(1S,2R,7S,8S,8aS)-7-[2-(Benzloxy)ethyl]-8-hydroxy-1,2-O-isopropylidenedi oxyindolizidin-5-one (69) and (1S, 2R,7S,8R,8aR)-7-[2-(Benzyloxy)ethyl]-8-hydroxy-1,2-O-isopropylidenedioxyindolizidin-5-one (70). Palladium hydroxide on carbon (50 mg) was added to a solution of the mixture of the epoxides 66αβ (1.7:1, 325 mg, 0.78 mmol) in MeOH/EtOAc (1:1, 12 mL). The flask was evacuated (aspirator) and purged with hydrogen three times, and the resulting heterogenous mixture was stirred under a balloon of hydrogen. After 3 h, hydrogen was evacuated, the mixture was filtered, and the filtrate was concentrated. The residue was dissolved in MeOH (12 mL), sodium methoxide (21 mg, 0.38 mmol) was added, and the mixture was warned to reflux. Reaction progress was monitored by IR for the disappearance of the ester and lactone carbonyl stretches at 1730 $cm^{-1}$ and 1780 $cm^{-1}$ and appearance of the lactam carbonyl stretch at 1625 $cm^{-1}$. After 48 h, the mixture was cooled to room temperature and concentrated. The residue was dissolved in $CH_2Cl_2$/MeOH (20:1, 10 mL), Florisil (1 g) was added, and the mixture was stirred for 15 min. The suspension was then filtered through Celite and the filtrate was concentrated. Chromatography (100:1 to 75:1 $CH_2Cl_2$/MeOH) provided 250 mg (89%) of a mixture (1.7:1 based on $^1H$ NMR integration) of the lactams 69 and 70 as a colorless oil. $R_f$=0.28 (20:1 $CHCl_3$/MeOH); $^1H$ NMR ($CDCl_3$, 300 MHz, α indicates major isomer; β indicates minor isomer, ratio α/β=1.7:1) δ7.2–7.4 (m, 5Hα+5Hβ), 4.81 (dd, J=4.3, 5.9 Hz, 1Hα), 4.69 (m, 1Hα+1Hβ), 4.15–4.6 (m, 3Hα+

4Hβ), 4.27 (dd, J=6.6, 13.5 Hz, 1Hβ), 4.12 (d, J=13.5 Hz, 1Hα), 3.80 (m, 1Hα+1Hβ), 3.4–3.65 (m, 2Hα+3Hβ), 3.30 (m, 1Hα+1Hβ), 3.10 (dd, J=5.2, 13.5 Hz, 1Hα), 2.35–2.55 (m, 2Hα+1Hβ), 1.9–2.2 (m, 2Hα+3Hβ), 1.60 (m, 1Hα+1Hβ), 1.51 (s, 3Hβ), 1.41 (s, 3Hα), 1.34 (s, 3Hβ), 1.32 (s, 3Hα), $^{13}$C NMR (CDCl$_3$, 75 MHz, α indicates major isomer, β indicates minor isomer) δ167.7 (β), 167.6 (α), 137.3 (β), 173.2 (α), 128.2, 127.6, 127.5, 113.8 (β), 111.7 (α), 83.5 (β), 79.5 (α), 77.5 (α), 76.6 (β), 73.1 (α), 73.0 (β), 70.0 (β), 68.6 (α), 68.4 (β), 65.8 (α) 64.9 (β), 50.4 (α), 48.9 (β), 38.7 (α), 36.6 (α), 35.9 (β), 35.7 (β), 32.4 (α), 29.2 (β), 27.5 (β), 26.4 (α), 25.3 (β), 24.6 (α); IR (neat) 3350 (br, m), 2935 (m), 2836 (m), 1626 (s) cm$^{-1}$; MS (CI, NH$_3$) m/z (rel intensity) 362 [(M+H)$^+$, 100]; HRMS (CI, NH$_3$) calcd for C$_{20}$H$_{27}$NO$_5$H [(M+H)$^+$]362.1967; found 362.1983.

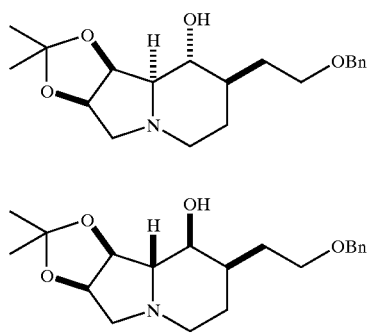

73

74

(1S,2R,7S,8R, 8aR)-7-[2-(Benzyloxy)ethyl]-8-hydroxy-1,2-O-isopropylidenedi oxyindolizidine (73) and (1S,2R,7S, 8S,8aS)-7-[2-Benzyloxy)ethyl]-8-hydroxy-1,2-O-isopropylidenedioxyindolizidine (74). Reduction of the mixture of lactams 69 and 70 (1.7:1, 235 mg, 0.65 mmol) was carried out with borane-methyl sulfide complex. Chromatography (100:1 to 25:1 CH$_2$Cl$_2$MeOH gradient) provided 125 mg (55%) of the indolizidine 73 as a white crystalline solid followed by 70 mg (31%) of the indolizidine 74 as a pale yellow oil.

Data for 73 (major): R$_f$=0.35 (20:1 CHCl$_3$/MeOH); [α]$^{23}_D$=−42.3° (c 0.66, CHCl$_3$); mp 85° C.; $^1$H NMR (CDCl$_3$, 300 MHz) δ7.2–7.4 (m, 5H), 4.73 (dd, J=4.5, 6.2 Hz, 1H, H$_1$), 4.61 (dd, J=4.3, 6.2 Hz, 1H, H$_2$), 4.52 (ABq, J=12.2 Hz, Δv=19.7 Hz, 2H), 3.89 (d, J=2.5 Hz, 1H, H$_{OH}$), 3.60 (m, 1H, H$_{10}$), 3.52 (m, 1H, H$_8$), 3.49 (dt, J=3.8, 9.4 Hz, 1H, H$_{10}$), 3.13 (d, J=10.6 Hz, 1H, H$_{3eq}$), 2.99 (ddd, J=2.5, 4.0, 10.8 Hz, 1H, H$_{5eq}$), 2.10 (dd, J=4.3, 10.7 Hz, 1H, H$_{3ax}$), 1.90 (m, 2H, H$_{5ax,9}$), 1.68 (dd, J=4.5, 8.9 Hz, 1H, H$_{8a}$), 1.55–1.65 (m, 2H, H$_{6,9}$), 1.52 (s, 3H), 1.35–5.5 (m, 2H, H$_{6,7}$), 1.34 (s, 3H); $^{13}$C NMR (CDCl$_3$, 75 MHz) δ137.6, 128.4, 127.9, 127.7, 111.0, 79.2, 78.5, 73.1, 73.0, 71.4, 69.1, 59.8, 51.6, 42.8, 34.2, 31.7, 25.9, 24.5; IR (neat) 3450 (br m), 2934 (s), 2856 (m), 2786 (m), 1370 (m) cm$^{-1}$; MS (CI, NH$_3$) m/z (rel intensity) 348 [(M+H)$^+$, 88], 330 (42), 256 (31), 107 (100), 91 (88); HRMS (CI, NH$_3$) calcd for C$_{20}$H$_{29}$NO$_4$H [(M+H)$^+$]348.2175; found 348.2168.

Data for 74 (minor): R$_f$=0.26 (20:1 CHCl$_3$/MeOH); [α]$^{23}_D$=−3.6° (c 0.50, CHCl$_3$); $^1$H NMR (CDCl$_3$, 300 MHz) δ7.2–7.4 (m, 5H), 4.69 (ddd, J=5.1, 6.5, 7.2 Hz, 1H, H$_2$), 4.54 (s, 2H), 4.48 (dd, J=5.7, 7.3 Hz, 1H, H$_1$), 3.59 (m, 2H, H$_{10,8}$), 3.46 (m, 1H, H$_{10}$), 3.35 (dd, J=6.3, 9.3 Hz, 1H, H$_{3eq}$), 3.24 (d, J=5.3 Hz, 1H, H$_{OH}$), 2.65, (ddd, J=2.5, 4.5, 11.4 Hz, 1H, H$_{5eq}$), 2.43 (dd, J=5.1, 9.3 Hz, 1H, H$_{3ax}$), 2.33 (td, J=2.9, 12.0 Hz, 1H, H$_{5ax}$), 2.24 (dd, J=5.6, 9.8 Hz, 1H, 11$_{8a}$), 2.11 (m, 2H, H$_{7,9}$), 1.76 (m, 1H, H$_6$), 1.59 (ddd, J=2.6, 5.2, 13.8 Hz, 1H, H$_6$), 1.52 (s, 3H), 1.46 (m, 1H, H$_9$), 1.33 (s, 3H); $^{13}$C NMR (CDCl$_3$75 MHz) δ137.8, 128.4, 127.7, 127.6, 114.1, 83.5, 77.6, 73.2, 72.7, 69.8, 68.7, 59.4, 46.2, 37.3, 30.0, 27.2, 29.9, 25.0; IR (neat) 3450 (br m), 2932 (s), 2859 (m), 2800 (m), 1372 (m) cm$^{-1}$; MS (CI, CH$_4$ and NH$_3$) m/z (rel intensity) 348 [(M+H)$^+$, 100]330 (45), 256 (50), 91 (30); HRMS (CI, CH$_4$ and NH$_3$) calcd for C$_{20}$H$_{29}$NO$_4$H [(M+H)$^+$]348.2175; found 348.2181.

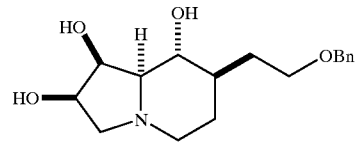

76

(1S,2R,7R,8R,8aR)-7-[2-(Benzyloxy)ethyl]-1,2,8-trihydroxyindolizidine [(7R-7-(2-Benzyloxyethyl) swainsonine] (76). The acetonide of the indolizidine 73 (100 mg, 0.29 mmol) was hydrolized with 6 N HCl in THF. Recrystallization from EtOAc provided 77 mg (86%) of 76 as a white solid. R$_f$=0.18 (50:25:1 EtOAc/EtOH/Aq. NH$_4$OH); [α]$^{23}_D$=−20.5° (c 0.78, CH$_3$OH); mp 174° C.; $^1$H NMR (CD$_3$OD, 300 MHz) δ7.2–7.4 (m, 5H), 4.52 (m, 1H, H$_2$), 4.50 (ABq, J=11.7, Δv=20.4 Hz, 2H); 4.36 (m, 1H, H$_1$) 3.66 (t,J=10.0 Hz, 1H, H$_8$), 3.61 (t, J=6.3 Hz, 2H, H$_{10}$), 3.41 (m, 2H, H$_5$ and H$_3$), 3.31 (dd, J=4.5, 11.9 Hz, 1H, H$_3$), 3.02 (dd, J=1.8, 9.9 Hz, 1H, H$_{8a}$) 2.93 (td, J=2.5, 12.5 Hz, 1H, H$_5$), 2.21 (m, 1H, H$_9$), 2.04 (m, 1H, H$_6$), 1.68 (m, 1H, H$_7$), 1.48 (m, 2H, H$_6$ and H$_9$); $^{13}$C NMR (CD$_3$OD, 90 MHz) δ 139.8, 129.5, 129.1, 128.9, 74.1, 73.7, 69.9, 69.8, 69.2, 68.9, 60.2, 41.0, 32.6, 28.7; IR (neat) 3280 (br s), 2939 (m), 2864 (m), 1101 (s) cm$^{-1}$; MS (CI, NH$_3$) m/z (rel intensity) 308 [(M+H)$^+$, 100], 270 (25), 254 (24), 106 (21), 91 (29); HRMS (CI, NH$_3$) calcd for C$_{17}$H$_{24}$NO$_4$H [(M+H)$^+$]308.1862; found 308.1850.

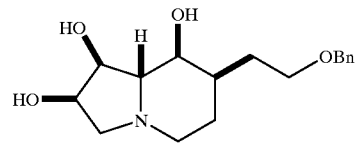

78

(1S,2R,7R,8S,8aS)-7-[2-(Benzyloxy)ethyl]-1,2,8-trihydroxyindolizidine [(7R)-7-(2-Benzyloxyethyl)-8,8a-diepiswainsonine](78). The acetonide of the indolizidine 74 (45 mg, 0.13 mmol) was hydrolyzed with 6N HCl in THF. Chromatography (75:25:1 EtOAc/EtOH/Aq. NH$_4$OH) provided 36 mg (90%) of the title compound as a pale yellow oil. R$_f$=0.17 (50:25:1 EtOAc/EtOH/Aq. NH$_4$OH); $^1$H NMR (CD$_3$OD, 300 MHz) δ7.2–7.5 (m, 5H), 4.50 (ABq, J=11.8 Hz, Δv=14.5 Hz, 2H), 4.11 (td, J=5.9, 6.5 Hz, 1H), 3.65 (dd, J=4.4, 9.0 Hz, 1H), 3.57 (t, J=6.7 Hz, 2H), 3.34 (dd, J=6.7, 10.2 Hz, 1H), 2.64 (dt, J=4.1, 11.3 Hz, 1H), 2.34 (td, J=3.5, 11.1 Hz, 1H), 2.29 (J=5.6, 10.3 Hz, 1H), 2.21 (t, J=8.5 Hz, 1H), 2.01 (m, 2H), 1.5–1.8 (m, 3H); $^{13}$C NMR (CD$_3$OD, 90 MHz) δ139.8, 129.5, 129.1, 128.8, 75.1, 74.2, 74.0, 70.7, 68.6, 68.2, 62.2, 48.4, 37.2, 28.7, 26.7; IR (neat) 3350 (br s), 2927 (s), 2857 (m,), 1070 (s) cm$^{-1}$; MS (CI, CH$_4$m/z (rel intensity) 308 [(M+H)$^+$, 100], 290 (25), 216 (30), 198 (23), 91 (30); HRMS (CI, CH$_4$) calcd for C$_{17}$H$_{24}$NO$_4$H [(M+H)$^+$] 308.1862; found 308.1850.

Part III: Synthesis of 6- and 7-Substituted Swainsonine Analogs Using (1S,2R,8R)-8-Hydroxy-1,2-O-isopropylidenedioxyindolizidine-5-one or (1S,2R,8R)-8-Hydroxy-1,2-O-cyclohexylidenedioxyindolizidine-5-one as a Starting Material.

General Procedure for the Preparation of Lactams 98 and 99. To a solution of (1S,2R,8R)-8-hydroxy-1,2-O-isopropylidenedioxyindolizidine-5-one or (1S,2R,8R)-8-hydroxy-1,2-O-cyclohexylidenedioxyindolizidine-5-one (1 equiv)[23] in DMF at 0° C. was added imidazole (2 equiv) followed by TBDMSCl (2 equiv). The reaction was warmed up to rt and stirred for 3–12 h. The mixture was poured into ether and was washed with saturated $NH_4Cl$. The combined aqueous layers were back-extracted with ether. The combined organic layers were washed with water. 5% $NaHCO_3$, and brine, dried ($MgSO_4$) and concentrated. Chromatography (1:4 to 3:1 EtOAc/hexane/gradient) yielded 98 or 99 as a white solid.

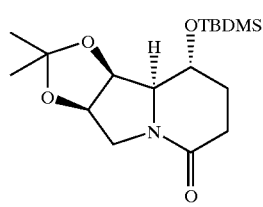

98

(1S,2R,8R,8aR)-8-[(tert-Butyldimethylsilyl)oxy]-1,2-(isopropylidenedioxy)indolizidin-5-one (98). According to the general procedure, (1S,2R8R)-8-hydroxy-1,2-O-isopropylidenedioxyindolizidine-5-one[23] (2.9 g, 12.8 mmol) was treated with TBDMSCl (1.92 g, 25.5 mmol) and imidazole (1.73 g, 25.5 mmol) in DMf (30 mL) at rt for 12 h to afford 3.63 g (84%) of 98 as a white solid. $^1$H NMR ($CDCl_3$, 360 MHz) δ4.65–4.71 (m, 2H), 4.11–4.16 (m, 1H), 4.11 (d, J=12.8 Hz, 1H), 3.28 (dd, J=3.6, 7.7 Hz, 1H), 3.11 (dd, J=5, 13.4 Hz, 1H), 2.48 (ddd, J=3.5, 5.8, 17.7 Hz, 1H), 2.36 (ddd, J=5.8, 11.7, 17.6 Hz, 1H), 1.94–2.01 (m, 1H), 1.82 (ddd, J=5.8, 11.6, 23.3 Hz, 1H), 1.40 (s, 3H), 1.30 (s, 3H), 0.89 (s, 9H), 0.11 (s, 3H), 0.10 (s, 3H); $^{13}$C NMR ($CDCl_3$, 90 MHz) δ168.5, 111.6, 79.5, 77.3, 66.8, 65.6, 50.9, 30.5, 29.5, 26.5, 25.6, 24.6, 17.9, −4.6, −5.1; IR (cm$^{-1}$, solution in $CHCl_3$) 2955, 2958, 1636, 1471, 1384, 1264, 1095, 837; MS (CI, $NH_3$) m/z (rel int) 342 (MH$^+$, 100), 284 (6), 226 (38); HRMS calcd for $C_{17}H_{31}NO_4SiH$ (MH$^+$) 342.2101, found 342.2110.

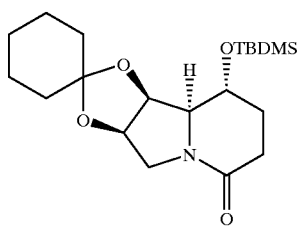

99

(1S,2R,8R,8aR)-8-[(tert-Butyldimethylsilyl)oxy]-1,2-(cyclohexylidenedioxy)indolizidine-5-one (99). According to the general procedure, (1S,2R,8R)-8-hydroxy-1,2-O-cyclohexylidenedioxyindolizidine-5-one (505 mg, 1.89 mmol) was treated with TBDMSCl (570 mg, 3.77 mmol) and imidazole (257 mg, 3.77 mmol) in DMF (5 mL) ar rt for 12 h to afford 99 (662 mg, 92%). For compound 99, $^1$H NMR ($CDCl_3$, 360 MHz) δ 4.64–4.71 (m, 2H), 4.05–4.20 (m, 1H), 4.10 (d, J=13.6 Hz, 1H), 3.26 (dd, J=3.7, 7.9 Hz, 1H), 3.10 (dd, J=5.5, 13.8 Hz, 1H), 2.48 (br d, J=16.2 Hz, 1H), 2.36 (ddd, J=5.9, 12.2, 17.7 Hz, 1H), 1.92–2.03 (m, 1H), 1.81 (ddd, J=5.9, 11.7, 23.6 Hz, 1H), 1.25–1.65 (m, 10H), 0.88 (s, 9H), 0.13 (s, 3H), 0.10 (s, 3H); $^{13}$C NMR (90 MHz, $CDCl_3$) δ 168.6, 112.5, 79.1, 76.9, 67.0, 65.6, 51.2, 36.4, 34.3, 30.5, 29.6, 25.7 (3C), 25.1, 24.0, 23.6, 17.9, −4.5, −4.9 IR (cm$^{-1}$, solution in $CHCl_3$) 2938, 2858, 1636, 1471, 1450, 1166, 1121, 838; MS (CI, $NH_3$) m/z (rel int) 382 (MH$^+$, 100), 338 (1.5), 324 (10.8), 268 (12.4), 250 (1.2), 226 (16.4), 170 (2.2), 152 (1.2), 143 (2.2), 134 (3.0); HRMS calcd for $C_{20}H_{36}O_4SiN$ (MH$^+$)382.2414, found 382.2414.

General Procedure for the Generation and Alkylation of the Enolates of 98 and 99. To a solution of the lactam 98 or 99 (1 equiv) and DMPU (3 equiv) in THF at −78° C. was added dropwise s-BuLi (1.3 equiv). The mixture was stirred for 1 h at −78° C. and then the alkylating agent (2–3 equiv) was added. After stirring at −78° C. for 30 min the solution was warmed up to room temperature and stirred for 2–12 h. The reaction was quenched by the addition of water. EtOAc was added and the layers were separated. The aqueous layer was extracted with EtOAc. The combined organic layers were washed with water, brine, dried ($MgSO_4$) and concentrated. Chromatography (1:9 to 1:1 EtOAc/Hexane gradient) provided α-diastereomer followed by β-diastereomer in various ratios. Examples are shown in Table 4.

TABLE 4

Sample Enolate Alkylations

| lactam | base | electrophile | yield of 100 | ratio (α:β) |
|---|---|---|---|---|
| 98 | s-BuLi | $CH_3I$ | 97 | 1:2.8 |
| 98 | $iPr_2NLi$ | $PhCH_2Br$ | 41 | 1.3:1 |
| 98 | s-BuLi | $Br(CH_2)_4Cl$ | 74 | 1:1.96 |
| 99 | s-BuLi | $PhCH_2Br$ | 84 | 1:1.26 |
| 99 | s-BuLi | $HC{\equiv}CCH_2Br$ | 72 | β only |
| 99 | s-BuLi | iPrI | 33 | 1.15:1 |
| 99 | s-BuLi | $CH_2{=}CHCH_2Br$ | 83 | 1:3.4 |

Selected Data for Compounds Reported in Table 4:

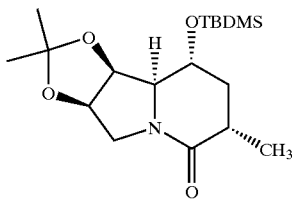

(1S,2R,6S,8R,8aR)-6-Methyl-8-[(tert-Butyldimethylsilyl)oxy]-1,2-(isopropylidenedioxy)indolizidine-5-one. $^1$H NMR (360 MHz, CDCl$_3$) δ 4.53–4.61 (m, 2H), 4.00–4.07 (m, 1H), 3.99 (d, J=13.6 Hz, 1H), 3.18 (dd, J=3.6, 8.6 Hz, 1H), 3.00 (dd, J=5.3, 13.5 Hz, 1H), 2.30 (dt, J=6.5, 13.1 Hz, 1H), 1.94 (dt, J=4.6, 12.9 Hz, 1H), 1.53 (dd, J=12.1, 24.4 Hz, 1H), 1.28 (s, 3H), 1.19 (s, 3H), 1.13 (d, J=7.1 Hz, 3H), 0.78 (s, 9H), 0.00 (s, 6H); $^{13}$C NMR (90 MHz, CDCl$_3$) δ 171.3, 111.6, 79.5, 77.6, 67.4, 65.1, 51.1, 39.7, 34.7, 26.6, 25.7 (3C), 24.7, 17.9, 17.2, −4.6, −5.0; IR (cm$^{-1}$, solution in CHCl$_3$) 3000, 2933, 2858, 1633, 1465, 1445, 1384, 1164, 1134, 1096, 880, 839; MS (CI, NH$_3$) m/z (rel int) 356 (MH$^+$, 100), 298 (10.7), 240 (33.7), 184 (4.1), 143 (4.7), 98 (4.2); HRMS calcd for C$_{18}$H$_{34}$O$_4$SiN (MH$^+$) 356.2257, found 356.2252.

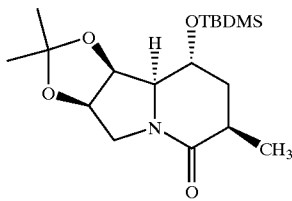

(1S,2R,6R,8R,8aR)-6-Methyl-8-[(tert-Butyldimethylsilyl)oxy]-1,2-(isopropylidenedioxy)indolizidine-5-one. $^1$H NMR (360 MHz, CDCl$_3$) δ 4.62–4.69 (m, 2H), 4.31 (ddd, J=4.0, 6.6, 10.2 Hz, 1H), 4.11 (d, J=13.5 Hz, 1H), 3.24 (dd, J=3.8, 6.7 Hz, 1H), 3.03 (dd, J=5.0, 13.5 Hz, 1H), 2.50–2.65 (m, 1H), 1.92 (ddd, J =5.6, 9.7, 13.1 Hz, 1H), 1.76 (dt, J=4.2, 13.1 Hz, 1H), 1.37 (s, 3H), 1.28 (s, 3H), 1.25 (d, J=7.4 Hz, 3H), 0.87 (s, 9H), 0.0091 (s, 3H), 0.084 (s, 3H); $^{13}$C NMR (90 MHz, CDCl$_3$) δ 172.5, 111.5, 79.6, 77.5, 67.3, 62.7, 50.6, 37.7, 33.9, 26.4, 25.7 (3C), 24.6, 18.5, 17.9, −4.7, −5.0; IR (cm$^{-1}$, solution in CHCl$_3$) 2995, 2952, 2932, 2858, 1634, 1471, 1445, 1384, 1259, 1163, 1104, 1092, 1027, 990, 839; MS (CI, NH$_3$) m/z (rel int) 356 (MH$^+$, 100), 298 (7.2), 240 (21.2), 184 (2.6), 143 (2.9), 98 (2.7); HRMS calcd for C$_{18}$H$_{34}$O$_4$SiN (MH$^+$) 356.2257, found 356.2263.

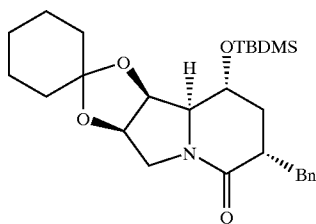

(1S,2R,6S,8R,8aR)-6-Benzyl-8-[(tert-Butyldimethylsilyl)oxy]-1,2-(cyclohexylidenedioxy)indolizidine-5-one. $^1$H NMR (360 MHz, CDCl$_3$) δ 7.15–7.32 (m, 5H), 4.70 (br t, J=5.6 Hz, 1H), 4.62 (dd, J=3.9, 5.9 Hz, 1H), 4.15 (d, J=13.7 Hz, 1H), 4.07–4.11 (m, 1H), 3.36 (dd, J=4.0, 13.5 Hz, 1H), 3.22 (dd, J=3.7, 8.8 Hz, 1H), 3.12 (dd, J=5.5, 13.5 Hz, 1H), 2.74 (dd, J=13.4, 13.6 Hz, 1H), 2.50–2.62 (m, 1H), 1.83–1.89 (m, 1H), 1.20–1.69 (m, 11H), 0.84 (s, 9H), 0.063 (s, 3H), −0.0052 (s, 3H); $^{13}$C NMR (90 MHz, CDCl$_3$) δ 169.9, 139.7, 129.3 (2C), 128.3 (2C), 126.1, 112.5, 79.2, 77.2, 67.3, 65.4, 51.3, 41.4, 37.3, 36.4, 36.2, 34.4, 25.6 (3C), 25.1, 24.0, 23.7, 17.9, −4.5, −5.0; IR (cm$^{-1}$, solution in CHCl$_3$) 2937, 2858, 1631, 1463, 1450, 1336, 1164, 1131, 1107, 1091, 839; MS (CI, NH$_3$) m/z (rel int) 472 (MH$^+$, 100), 414 (7.0), 358 (2.8), 316 (6.1), 224 (1.1), 190 (1.1), 119 (1.6), 83 (6.3); HRMS calcd for C$_{27}$H$_{42}$O$_4$SiN (MH$^+$) 472.2883, found 472,2872.

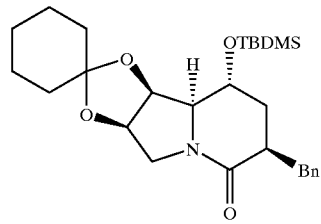

(1S,2R,6R,8R,8aR)-6-Benzyl-8-[(tert-Butyldimethylsilyl)oxy]-1,2-(cyclohexylidenedioxy)indolizidine-5-one. $^1$H NMR (360 MHz, CDCl$_3$) δ 7.18–7.33 (m, 5H), 4.72 (t, J=5.2 Hz, 1H), 4.65 (dd, J=3.8, 5.8 Hz, 1H), 4.30 (dd, J=6.8, 14.2 Hz, 1H), 4.16 (d, J=13.7 Hz, 1H), 3.32 (dd, J=4.1, 13.9 Hz, 1H), 3.25 (dd, J=3.8, 7.0 Hz, 1H), 3.12 (dd, J=5.4, 13.6 Hz, 1H), 2.75–2.85 (m, 1H), 2.63 (dd, J=11.0, 13.6 Hz, 1H), 1.30–1.75 (m, 12H), 0.83 (s, 9H), 0.082 (s, 3H), −0.024 (s, 3H); $^{13}$C NMR (90 MHz, CDCl$_3$) δ 171.6, 139.4, 129.2 (2C), 128.6 (2C), 126.5, 112.5, 79.2, 67.6, 62.4, 51.2, 41.2, 38.1, 36.5, 34.4, 32.8, 32.0, 25.7 (3C), 25.1, 24.1, 23.8, 17.9, −4.5, −4.8; IR (cm$^{-1}$, solution in CHCl$_3$) 2936, 2859, 1632, 1470, 1451, 1334, 1131, 1107, 954, 838; MS (Cl, NH$_3$) m/z (rel int) 472 (MH$^+$, 100), 382 (1.5), 358 (44.6), 222 (1.2), 193 (1.2), 108 (4.0), 91 (2.3); HRMS calcd for C$_{27}$H$_{42}$O$_4$SiN (MH$^+$) 472.2883, found 472.2871.

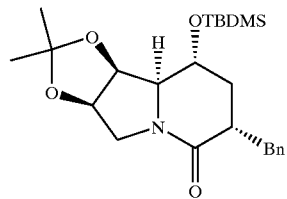

(1S,2R,6S,8R,8aR)-6-Benzyl-8-[(tert-Butyldimethylsilyl)oxy]-1,2-(isopropylidenedioxy)indolizidin-5-one. $^1$H NMR (CDCl$_3$, 400 MHz) δ 7.17–7.32 (m, 5H), 4.69 (t, J=5.6 Hz, 1H), 4.63 (dd, J=4.8, 5.8 Hz, 1H), 4.15 (d, J=13.5 Hz, 1H), 4.07 (ddd, J=4.1, 8.8, 12.4 Hz, 1H), 3.36 (dd, J=4.1, 13.7 Hz, 1H), 3.23 (dd, J=3.8, 8.5 Hz, 1H), 3.13 (dd, J=5.5, 13.7 Hz, 1H), 2.75 (dd, J=9.1, 13.5 Hz, 1H), 2.58 (m, 1H), 1.86 (ddd, J=4.1, 5.5, 12.9 Hz, 1H), 1.58 (m, 1H), 1.40(s, 3H), 1.29 (s, 3H), 0.84 (s, 9H), 0.05 (s, 3H), 0.03 (s, 3H); IR (cm$^{-1}$, solution in CHCl$_3$) 2931, 2858, 1632, 1463, 1384, 1260, 1096, 906; MS (EI, 70 eV) m/z (rel int) 431 (M$^+$,9), 374 (41), 316 (100), 260 (13), 225 (14), 174 (15), 143 (17), 117 (14), 91 (21); HRMS calcd for C$_{24}$H$_{37}$NO$_4$Si (M$^+$) 431.2492, found 431.2486.

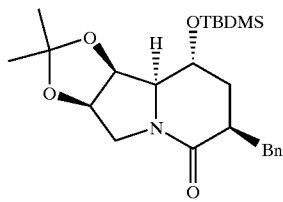

(1S,2R,6R,8R,8aR)-6-Benzyl-8-[(tert-Butyldimethylsilyl)oxy]-1,2-(isopropylidenedioxy)indolizidin-5-one. $^1$H NMR (CDCl$_3$, 400 MHz) δ 7.18–7.32 (m, 5H), 4.70 (t, J=5.8 Hz, 1H), 4.65 (dd, J=3.8, 5.8 Hz, 1H), 4.26 (dd, J=6.6, 13.2 Hz, 1H), 4.17 (d, J=13.7 Hz, 1H), 3.33 (dd, J=3.5, 13.5 Hz, 1H), 3.26 (dd, J =3.8, 6.3 Hz, 1H), 3.10 (dd, J=4.9, 13.2 Hz, 1H), 2.74–2.83 (m, 1H), 2.64 (dd, J=11.0, 13.5 Hz, 1H), 1.71 (dd, J=4.9, 6.6 Hz, 2H), 1.40 (s, 3H), 0.82 (s, 9H), 0.05 (s, 3H), −0.04 (s, 3H); MS (EI, 70 eV) m/z (rel int) 431 (M$^+$, 9), 374 (41) 316 (100), 260 (15), 225 (15), 174 (17), 143 (24), 117 (20), 91 (44), 84 (19); HRMS calcd for C$_{24}$H$_{37}$NO$_4$Si (M$^+$) 431.2492, found 431.2490.

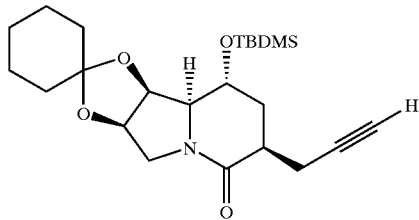

(1S,2R,6R,8R,8aR)-6-Propargyl-8-[(tert-Butyldimethylsilyl)oxy]-1,2-(cyclohexylidenedioxy)indolizidine-5-one. $^1$H NMR (360 MHz, CDCl$_3$) δ 4.70 (t, J=5.6 Hz, 1H), 4.66 (dd, J=3.8, 5.9 Hz, 1H), 4.41 (ddd, J=3.9, 6.2, 9.8 Hz, 1H), 4.14 (d, J=13.6 Hz, 1H), 3.28 (dd, J=3.8, 6.2 Hz, 1H), 3.07 (dd, J=5.4, 13.5 Hz, 1H), 2.79 (ddd, J=2.8, 4.2, 16.6 Hz, 1H), 2.68 (dt, J=4.9, 14.6 Hz, 1H), 2.42 (ddd, J=2.7, 9.8, 16.6 Hz, 1H), 2.19 (dt, J=4.5, 13.4 Hz, 1H), 2.03 (t, J=2.6 Hz, 1H), 1.94–2.00 (m, 1H), 1.20–1.70 (m, 10H), 0.91 (s, 9H), 0.15 (s, 6H); $^{13}$C NMR (90 MHz, CDCl$_3$) δ 170.0, 112.5, 81.9, 79.2, 77.1, 70.3, 67.5, 62.8, 50.9, 37.8, 36.4, 34.3, 33.9, 25.7 (3C), 25.0, 24.0, 23.7, 21.4, 17.9, −4.5, −4.9; IR (cm$^{-1}$, solution in CHCl$_3$) 3007, 2938, 2858, 1636, 1464, 1449, 1370, 1252, 1163, 1131, 1107, 952, 839; MS (CI, NH$_3$) m/z (rel int) 420 (MH$^+$, 100), 382 (1.6), 362 (9.4), 306 (2.9), 264 (9.2), 224 (1.0), 204 (1.2), 83 (7.0); HRMS calcd for C$_{23}$H$_{38}$O$_4$SiN (MH$^+$) 420.2570, found 420.2564.

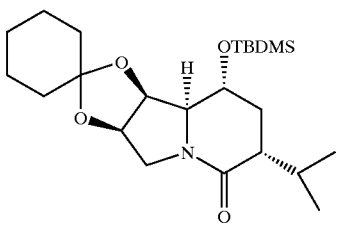

(1S,2R,6S,8R,8aR)-6-Isopropyl-8-[(tert-Butyldimethylsilyl)oxy]-1,2-(cyclohexylidenedioxy)indolizidine-5-one. $^1$H NMR (360 MHz, CDCl$_3$) δ 4.69 (t, J=5.2 Hz, 1H), 4.64 (dd, J=3.9, 5.9 Hz, 1H), 4.11–4.18 (m, 1H), 4.14 (d, J=13.3 Hz, 1H), 3.27 (dd, J=3.7, 8.6 Hz, 1H), 3.12 (dd, J=5.6, 13.6 Hz, 1H), 2.52–2.63 (m, 1H), 2.22–2.33 (m, 1H), 1.86 (ddd, J=4.1, 5.7, 12.6 Hz, 1H), 1.20–1.70 (m, 11H), 0.93 (d, J=7.1 Hz, 3H), 0.89 (s, 9H), 0.80 (d, J=6.8 Hz, 3H), 0.13 (s, 3H), 0.11 (s, 3H); $^{13}$C NMR (90 MHz, CDCl$_3$) δ 170.2, 112.5, 79.3, 77.1, 66.9, 65.7, 51.2, 45.1, 36.5, 34.5, 30.5, 27.8, 25.7 (3C), 25.1, 24.0, 23.7, 20.1, 17.9, 17.4, −4.4, −4.9; IR (cm$^{-1}$, solution in CHCl$_3$) 3001, 2938, 2858, 1627, 1464, 1447, 1370, 1252, 1164, 1119, 952, 840; MS (CI, NH$_3$) m/z (rel int) 424 (MH$^+$, 100), 366 (4.5), 310 (3.0), 268 (3.9), 204 (2.0), 117 (3.3), 83 (9.6); HRMS calcd for C$_{23}$H$_{42}$O$_4$SiN (MH$^+$) 424.2883, found 424.2877.

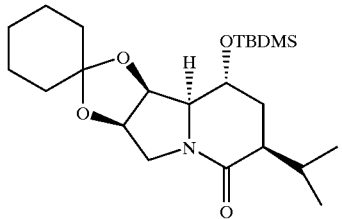

(1S,2R,6R,8R,8aR)-6-Isopropyl-8-[(tert-Butyldimethylsilyl)oxy]-1,2-(cyclohexylidenedioxy)indolizidine-5-one. $^1$H NMR (360 MHz, CDCl$_3$) δ 4.70 (t, J=5.6 Hz, 1H), 4.65 (dd, J=3.7, 5.9 Hz, 1H), 4.34 (ddd, J=4.3, 6.6, 10.7 Hz, 1H), 4.11 (d, J=13.5 Hz, 1H), 3.23 (dd, J=3.7, 6.6 Hz, 1H), 3.11 (dd, J=5.3, 13.6 Hz, 1H), 2.30–2.45 (m, 2H), 1.94 (dt, J=4.2, 13.5 Hz, 1H), 1.77 (ddd, J =6.5, 9.7, 13.6 Hz, 1H), 1.20–1.65 (m, 10H), 1.00 (d, J=6.7 Hz, 3H), 0.91 (s, 9H), 0.89 (d, J=6.8 Hz, 3H), 0.14 (s, 3H), 0.13 (s, 3H); $^{13}$C NMR (90 MHz, CDCl$_3$) δ 171.3, 112.4, 79.3, 76.9, 67.2, 63.7, 51.2, 44.6, 36.4, 34.3, 31.0, 29.1, 25.7 (3C), 25.1, 23.9, 23.7, 21.2, 19.4, 17.9, −4.4, −4.8; IR (cm$^{-1}$, solution in CHCl$_3$) 3002, 2938, 2585, 1710, 1627, 1464, 1449, 1370, 1252, 1106, 953, 839; MS (CI, NH$_3$) m/z (rel int) 424 (MH$^+$, 100), 366 (4.2), 310 (2.9), 268 (4.6), 204 (1.9), 117 (1.4), 83 (5.9); HRMS calcd for C$_{23}$H$_{42}$O$_4$SiN (MH$^+$) 424.2883, found 424.2869.

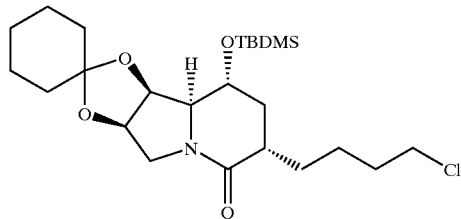

(1S,2R,6S, 8R,8aR)-6-[4'-Chloro-Butyl]-8-[(tert-Butyldimethylsilyl)oxy]-1,2-(cyclohexylidenedioxy)indolizidine-5-one. $^1$H NMR (360 MHz, CDCl$_3$) δ 4.71 (t, J=5.6 Hz, 1H), 4.66 (dd, J=3.8, 5.9 Hz, 1H), 4.16–4.20 (m, 1H), 4.12 (d, J=13.4 Hz, 1H), 3.50–3.60 (m, 2H), 3.28 (dd, J=3.8, 8.4 Hz, 1H), 3.11 (dd, J=5.5, 13.6 Hz, 1H), 2.26–2.38 (m, 1H), 2.04 (dt, J=4.7, 12.8 Hz, 1H), 1.85–2.00 (m, 1H), 1.75–1.85 (m, 2H), 1.15–1.70 (m, 14H), 0.91 (s, 9H), 0.15 (s, 3H), 0.13 (s, 3H); $^{13}$C NMR (90 MHz, CDCl$_3$) δ 170.5, 112.6, 79.3, 77.2, 67.3, 65.4, 51.4, 45.0, 39.4, 36.63, 36.56, 34.5, 32.7, 30.6, 29.8, 25.8 (3C), 25.2, 24.2, 24.1, 23.8, 18.0, −4.3, −4.8; IR (cm$^{-1}$, solution in CHCl$_3$) 3003, 2939, 2849, 1631, 1463, 1448, 1369, 1336, 1252, 1164, 1133, 1105, 1072, 952, 840; MS (CI, NH$_3$) m/z (rel int) 472 (MH$^+$, 100),440 (9.7), 422 (41.6), 382 (3.0), 358 (47.3), 308 (22.4), 268 (1.4), 108 (1.3), 91 (1.0); HRMS calcd for C$_{24}$H$_{43}$O$_4$SiNCl (MH$^+$) 472.2650, found 472.2651.

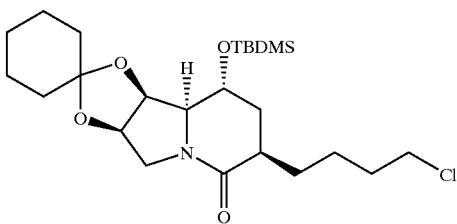

(1S,2R,6R,8R,8aR)-6-[4'-Chloro-Butyl]-8-[(tert-Butyldimethylsilyl)oxy]-1,2-(cyclohexylidenedioxy)indolizidine-5-one. $^1$H NMR (360 MHz, CDCl$_3$) δ 4.71 (t, J=5.4 Hz, 1H), 4.65 (dd, J=3.8, 5.9 Hz, 1H), 4.33 (dd, J=6.3, 13.3, 1H), 4.11 (d, J=13.5 Hz, 1H), 3.553 (t, J=6.6 Hz, 1H), 3.548 (t, J=6.5 Hz, 1H), 3.24 (dd, J=3.8, 7.1 Hz, 1H), 3.07 (dd, J=5.3, 13.5 Hz, 1H), 2.40–2.55 (m, 1H), 1.70–1.95 (m, 4H), 1.20–1.70 (m, 12H), 0.91 (s, 9H), 0.14 (s, 3H), 0.13 (s, 3H); $^{13}$C NMR (90 MHz, CDCl$_3$) δ 171.7, 112.4 79.2, 77.1, 67.3, 62.7, 51.0, 44.7, 39.3, 36.5, 34.5, 34.4, 32.4, 31.5, 25.7 (3C), 25.1, 24.8, 24.0, 23.7, 17.9, −4.5, −4.8; IR (cm$^{-1}$, solution in CHCl$_3$) 3001, 2939, 2858, 1632, 1464, 1449, 1369, 1335, 1253, 1163, 1130, 1106, 1072, 953, 839; MS (CI, NH$_3$) m/z (rel int) 472 (MH$^+$,100), 438 )2.7), 414 (1.4), 398 (6.8), 382 (13.8), 358 (13.5), 316 (1.6), 115 (1.9); HRMS calcd for C$_{24}$H$_{43}$O$_4$SiNCl (MH$^+$) 472.2650, found 472.2649.

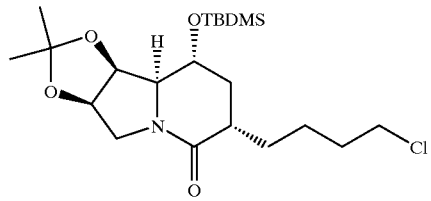

(1S,2R,6S,8R, 8aR)-6-[4'-Chlorobutyl]-8-[(tert-Butyldimethylsilyl)oxy]-1,2-(isopropylidenedioxy)indolizidin-5-one. $^1$H NMR (CDCl$_3$, 360 MHz) δ 4.68 (m, 2H), 4.1–4.18 (m, 1H), 4.12 (d, J=13.4, 1H), 3.51–3.58 (m, 2H), 3.30 (dd, J=3.6, 8.6 Hz, 1H), 3.12 (dd, J=5.2, 13.6 Hz, 1H), 2.33 (m, 1H), 2.04 (m, 1H), 1.45–2.0 (m, 7H), 1.39 (s, 3H), 1.31 (s, 3H), 0.90 (s, 9H), 0.12 (s, 6H); $^{13}$C NMR (CDCl$_3$, 90 MHz) δ 170.4, 111.6, 79.5, 77.4, 67.0, 65.3, 51.1, 44.9, 39.3, 36.5, 32.5, 30.5, 26.5, 25.6, 24.7, 24.0, 17.9, −4.6, −5.1; IR (cm$^{-1}$, solution in CHCl$_3$) 2953, 2958, 1631, 1463, 1383, 1264, 1096, 389; MS (CI, NH$_3$) m/z (rel int) 432 (MH$^+$, 100), 396 (76), 316 (16), 280 (13), 223 (14), 197 (25); HRMS calcd for C$_{21}$H$_{38}$NO$_4$SiClH (MH$^+$) 432.2337, found 432.2316.

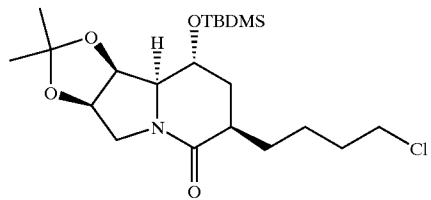

1S,2R,6R,8R,8aR)-6-[4'-Chlorobutyl]-8-[(tert-Butyldimethylsilyl)oxy]-1,2-(isopropylidenedioxy)indolizidin-5-one. $^1$H NMR (CDCl$_3$, 360 MHz) δ 4.64–4.71 (m, 2H), 4.30 (dd, J=6.5, 13.2 Hz, 1H), 4.12 (d, J=13.4 Hz, 1H), 3.55 (m, 2H, 3.25 (dd, J=3.8, 6.5 Hz, 1H), 3.05 (dd, J=4.9, 13.5 Hz, 1H), 2.47 (m, 1H), 1.72–1.90 (m, 5H), 1.48–1.68 (m, 3H), 1.38 (s, 3H), 1.31 (s, 3H), 0.90 (s, 9H), 0.12 (s, 6H); $^{13}$C NMR (CDCl$_3$, 90 MHz) δ 171.7, 111.5, 79.4, 77.4, 67.2, 62.7, 50.6, 44.7, 38.8, 34.4, 32.3, 31.2, 26.4, 25.6, 24.7, 24.5, 17.9, −4.7, −5.0; IR (cm$^{-1}$, solution in CHCl$_3$) 2930, 2857, 1633, 1464, 1383, 1265, 1098, 838; MS (CI, NH$_3$) m/z (rel int) 432 (MH$^+$, 100), 398 (21), 342 (66), 316 (21), 226 (15 ); HRMS calcd for C$_{21}$H$_{38}$NO$_4$SiClH (MH$^+$) 432.2337, found 432.2323.

The compounds resulting from the alkylation of the enolates of 98 and 99 could be converted to swainsonine analogs by reduction of the lactam and hydrolytic removal of the alcohol protecting groups, as was done with earlier compounds reported in this invention.

REFERENCES (1) Goss, P. E.; Baker, M. A.; Carver, J. P.; Dennis, J. W. *Clin. Cancer Res.* 1995, 1, 935–944.
(2) Schaaf-Lafontaine, N.; Balthazart, C.; Hooge, R. J. *Carbohydrate Res.* 1985, 138, 315–323.
(3) Cornil, I.; Kerbel, R. s.; Dennis, J. W. *J. Cell Biol.* 1990, 111, 773–782.
(4) Takano, R.; Nose, M.; Nishihira, I.; Kyogoku, M. *Am. J. Pathol.* 1990, 137.
(5) Seftor, R. E. B.; Seftor, E. A.; Grimes, W. J.; Liotta, L. A.; Stetler-Stevenson, W. G.; Welch, D. R.; Hendrix, M. J. C. *Melanoma Res.* 1991, 1, 43–54.
(6) Yagel, S.; Feinmesser, R.; Waghorne, C.; Lala, P. K.; Breitman, M. L.; Dennis, J. W. *Int. J. Cancer* 1989, 44, 685–690.
(7) Humphries, M. J.; Matsumoto, K.; White, S. L.; Molyneux, R. J.; Olden, K. *Clin, Exp. Metastasis* 1990, 8, 89–102.
(8) Yagita, M.; Saksela, E. *Scand. J. Immunol.* 1990, 31, 275–282.
(9) Kino, T.; Inamura, N.; Nakahara, K.; Kiyoto, S.; Goto, T.; Terano, H.; Kohsaka, M.; Aoki, H.; Imanaka, H. *J. Antibiot.* 1985, 38, 936–940.
(10) Oredipe, O. A.; White, S. L.; Grzegorzewski, K.; Gause, B. L.; Cha, J. K.; Miles, V. A.; Olden, K. *J. Natl. Cancer Inst* 1991, 83, 1149–1156.
(11) Dennis, J. W.; Koch, K.; Yousefi, S.; VanderElst, I. *Cancer Res* 1990, 50, 1867–72.
(12) Novikoff, P. M.; Touster, O.; Novikoff, A. B.; Tulsiani, D. P. *J. Cell. Biol.* 1985, 101, 339–349.
(13) Baptista, J. A.; Goss, P.; Nghiem, M.; Krepinsky, J. J.; Baker, M.; Dennis, J. W. *Clinical Chemistry* 1994, 40, 426–430.
(14) Goss, P. E.; Baptiste, J.; Fernandes, B.; Baker, M.; Dennis, J. W. *Cancer Research* 1994, 54, 1450–1457.
(15) Goss, P. E.; Baker, M. A.; Carver, J. P.; Dennis, J. W. *Clin. Cancer Res.* 1995, 1, 935–944.
(16) Johnson, W. S.; Werthemann, L.; Bartlett, W. R.; Brocksom, T. J.; Li, T.; Faulkner, D. J.; Petersen, M. R. *J. Am. Chem. Soc.* 1970, 92, 741–743.
(17) Wipf, P. In *Comprehensive Organic Synthesis*; B. M. Trost and I. Fleming, Ed.; Pergamon Press:; pp 827–873.
(18) Mekki, B.; Singh, G.; Wightman, R. H. *Tetrahedron Lett.* 1991, 32, 5143–5146.
(19) Hughes, D. L. In *Organic Reactions*; L. A. Paquette, Ed.; Wiley: New York, 1992; Vol. 42; pp 335–656.
(20) Zbiral, E.; Loibner, H. *Helv. Chim. Acta* 1976, 59, 2100–2113.
(21) Ireland, R. E.; Wipf, P.; Armstrong, J. D. *J. Org. Chem.* 1991, 56, 650–657.
(22) Ireland, R. E.; Mueller, R. H.; Willard, A. K. *J. Am. Chem. Soc.* 1976, 98, 2868–2877.
(23) Pearson, W. H.; Hembre, E. J., "Method for Preparing Swainsonine", U.S. Patent applied for October 1997.
(24) "Comprehensive Organic Synthesis", Trost, B. M.; Fleming, I., Eds. v. 1–9, 1991, Pergamon Press, Oxford.

(25) Testing performed at GlycoDesign, Inc.
(26) Wolff, H. In *Organic Reactions*; R. Adams, Ed.; Wiley: New York, 1946; Vol. 3; pp 307–336.

This application claims priority of U.S. patent application Ser. No. 60/027,585 filed on Oct. 3, 1996, which is incorporated herein in its entirety by reference.

We claim:

1. A compound of the formula I

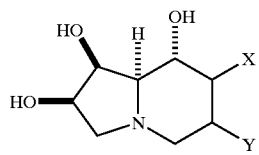

wherein X and Y may be any combination of the following groups, provided that X and Y cannot both be hydrogen:
—H;
—$CH_3$;
—$(CH_2)_n CH_3$, where n=1–11;
—s-alkyl;
—$(CH_2)_n$—G, where G is branched alkyl, n=1–11;
—$(CO_2)_n$—Ar, where n=1–11, and Ar is optionally substituted aryl or optionally substituted heteroaryl;
—$(CH_2)_n$—FG, where n=1–11, and FG is selected from the group consisting of alkenyl, alkynyl, substituted alkenyl, substituted alkynyl, halide, hydroxyl, ether, amino, alkylated amino, carboxylic acid, carboxylic ester, acylated alcohol, acylated amine, sulfonamide, sulfide, thiol, sulfone, sulfoxide, sulfonated amine, azide, aldehyde, ketone, oxime, and hydrazone;
—$CH(OH)R^4$, where $R^4$ is n-alkyl, s-alkyl, $(CH_2)_n$—G, $(CH_2)_n$—Ar, $(CH_2)_n$—FG, where G, Ar, and FG are defined above;
—$C(OH)R^4R^5$, where $R^4$ and $R^5$ are each idependently n-alkyl, s-alkyl, $(CH_2)_n$—G, $(CH_2)_n$—Ar, $(CH_2)_n$—FG, where G, Ar, and FG are defined above;
—$C(=O)R^4$ where $R^4$ is defined above;
—$C(=O)X$ where X is $R^4$ is an oxime or hydrazone residue;
—$N_3$;
—$NH_2$;
—$NHR^4$, where $R^4$ is as defined above;
—$NR^4R^5$, where $R^4$ and $R^5$ are as defined above;
—$NHCOR^4$, where $R^4$ is as defined above;
—$NR^4COR^5$, where $R^4$ and $R^5$ are as defined above;
—$NHSO_2R^4$, where $R^4$ is as defined above;
—$NR^4SO_2R^5$, where $R^4$ and $R^5$ are as defined above;
—SPh;
—S(O)Ph;
—$SO_2$Ph; or
—SePh.

2. The compound of claim 1, wherein Ar is selected from the group consisting of phenyl, naphthyl, pyridine, pyrimidine, pyrazine, triazine, furan, thiophene pyrrole, pyrazole, imidazole, thriazole, thiazole, oxazole, isothiazole, isoxazole, and substituted versions thereof.

3. The compound of claim 1, wherein at least one of X and Y is —$(CH_2)_n$—Ar, where n=1, and Ar is optionally substituted aryl or optionally substituted heteroaryl.

4. The compound of claim 3, wherein Ar is selected from the group consisting of phenyl, naphthyl, pyridine, pyrimidine, pyrazine, triazone, furan, thiophene pyrrole, pyrazole, imidazole, thriazole, thiazole, oxazole, isothiazole, isoxazole, and substituted versions thereof.

5. The compound of claim 3, wherein Ar is selected from the group consisting of phenyl, naphthyl, pyridine, pyrimidine, pyrazine, triazine, furan, thiophene pyrrole, pyrazole, imidazole, thriazole, thiazole, oxazole, isothiazole, and isoxazole.

6. The compound of claim 3, wherein Ar is phenyl.

7. The compound of claim 1, wherein at least one of X and Y is selected from the group consisting of
—$CH_3$;
—$(CH_2)_n CH_3$, where n=1–11;
—s-alkyl; and
—$(CH_2)_n$—G, where G is branched alkyl, n=1–11.

8. A pharmaceutical formulation comprising a compound according to claim 1 as an active agent, and a pharmaceutically acceptable carrier, excipient or diluent.

9. The pharmaceutical formulation of claim 8, wherein in said compound of formula I, Ar is selected from the group consisting of phenyl, naphthyl, pyridine, pyrimidine, pyrazine, triazine, furan, thiophene pyrrole, pyrazole, imidazole, thriazole, thiazole, oxazole, isothiazole, isoxazole, and substituted versions thereof.

10. The pharmaceutical formulation of claim 8, wherein in said compound of formula I, at least one of X and Y is —$(CH_2)_n$—Ar, where n=1, and Ar is optionally substituted aryl or optionally substituted heteroaryl.

11. The pharmaceutical formulation of claim 10, wherein Ar is selected from the group consisting of phenyl, naphthyl, pyridine, pyrimidine, pyrazine, triazine, furan, thiophene pyrrole, pyrazole, imidazole, thriazole, thiazole, oxazole, isothiazole, isoxazole, and substituted versions thereof.

12. The pharmaceutical formulation of claim 10, wherein Ar is selected from the group consisting of phenyl, naphthyl, pyridine, pyrimidine, pyrazine, triazine, furan, thiophene pyrrole, pyrazole, imidazole, thriazole, thiazole, oxazole, isothiazole, and isoxazole.

13. The pharmaceutical formulation of claim 10, wherein Ar is phenyl.

14. A method for stimulating the immune system, treating proliferative disorders, or treating microbial infections in a patient comprising administering an effective amount of a compound according to claim 1.

15. The method of claim 14, wherein said compound of formula I, Ar is selected from the group consisting of phenyl, naphthyl, pyridine, pyrimidine, pyrazine, triazine, furan, thiophene pyrrole, pyrazole, imidazole, thriazole, thiazole, oxazole, isothiazole, isoxazole, and substituted versions thereof.

16. The method of claim 14, wherein in said compound of formula I, at least one of X and Y is —$(CH_2)_n$—Ar, where n=1, and Ar is optionally substituted aryl or optionally substituted heteroaryl.

17. The method of claim 16, wherein in said compound of formula I, Ar is selected from the group consisting of phenyl, naphthyl, pyridine, pyrimidine, pyrazine, triazine, furan, thiophene, pyrrole, pyrazole, imidazole, thriazole, thiazole, oxazole, isothiazole, isoxazole, and substituted versions thereof.

18. The method of claim 16, wherein in said compound of formula I, Ar is selected from the group consisting of phenyl, naphthyl, pyridine, pyrimidine, pyrazine, triazine, furan, thiophene pyrrole, pyrazole, imidazole, thriazole, thiazole, oxazole, isothiazole, and isoxazole.

19. The method of claim 16, wherein in said compound of formula I, Ar is phenyl.

* * * * *

UNITED STATES PATENT AND TRADEMARK OFFICE
CERTIFICATE OF CORRECTION

PATENT NO. : 6,630,484 B1
DATED : October 7, 2003
INVENTOR(S) : William H. Pearson et al.

It is certified that error appears in the above-identified patent and that said Letters Patent is hereby corrected as shown below:

Column 2,
Line 51, "that it responsible" should read -- that is responsible --,
Line 53, "carbohydrates is tissues," should read -- carbohydrates in tissues, --.

Column 4,
Line 26, "6a and 7a/b" should read -- 6a/b and 7a/b --,
Line 35, "(2S)-11α in 28% yield, and a 1:1 mixture" should read -- (2S)-11α in 28% yield, (2R)-12α in 28% yield, and a 1:1 mixture --,
Line 39, "Epoxycster" should read -- Epoxyester --.

Column 8,
Line 65, "R'" should read -- R" --.

Column 9,
Line 9, "R" should read -- R" --,
Line 33, "G-$(CH_2)_n$–X" should read -- FG-$(CH_2)_n$-X --,
Line 47, "$R^4C(OR)R^5$" should read -- $R^4C(CO)R^5$ --.

Column 11,
Line 36, "37 R = $(CH_2)_3$ (88%)" should read -- 37 R = $(CH_2)_3CH_3$ (88%) --.

Column 15,
Line 49, "subtituted" should read -- substituted --,
Line 51, "R = $(CH_2)_{11}$" should read -- R = $(CH_2)_n$ --,
Line 65, "In Scheme 9," should read -- In Scheme 8A --.

Column 16,
Line 33, "suituted" should read -- substituted --,
Line 39, "Scheme 8", should read -- Scheme 8A --.

Column 18,
Line 8, "revisted" should read -- revisited --,
Line 17, "Synthesis of all diasteraomers" should read -- Synthesis of all diastereomers --,
Line 17, "the Cialsen rearrangement." should read -- the Claisen rearrangement. --.
Line 23, "See Fig. 2 & 3" should read -- See Fig. 2A & 7A --.

Column 19,
Line 45, "Diels-Adler" should read -- Diels-Alder --.

UNITED STATES PATENT AND TRADEMARK OFFICE
CERTIFICATE OF CORRECTION

PATENT NO. : 6,630,484 B1
DATED : October 7, 2003
INVENTOR(S) : William H. Pearson et al.

It is certified that error appears in the above-identified patent and that said Letters Patent is hereby corrected as shown below:

Column 20,
Line 55, "Inhibitoins" should read -- Inhibition --.

Column 21,
Line 6, "4" should read -- 6 --.
Line 14, "3" should read -- 2 --,
Line 15, "4" should read -- 6 --.
Line 39, Line 58, "in clinical trails." should read -- in clinical trials. --.

Column 22,
Line 57, "(52)" should read -- (53) --.

Column 25,
Line 14, "isopropylidenedioxyoctanoate [(2S)-12α]," should read -- isopropylidenedioxyoctanoate [(2R)-12α], --,
Line 32, "Data for (2S)-10α" should read -- Data for (2S)-10α: --,
Line 52, "Data for (2Rs)-14β" should read -- Data for (2RS)-14β --, Column 26,
Line 26, "at 1730 cm$^{-1}$ and appearance" should read -- at 1730 cm$^{-1}$ and 1780 cm$^{-1}$ and appearance --,
Line 65, "The reduction" should be -- reductive --.

Column 27,
Line 9, "R$_f$320.25" should read -- R$_f$=0.25 --,
Line 10, "$_D$=13.2+" should read -- $_D$= -13.2° --,
Line 14, "(dd, J=4.8, 13.6 Hz, 1H, H$_{ax}$)" should read -- (dd, J=4.8, 13.6 Hz, 1H, H$_{3ax}$) --,
Line 41, "(dd, J=3.9, 104 Hz," should read -- (dd, J=3.9, 10.4 Hz, --.

Column 28,
Line 33, "2.30 (m, 1H)" should read -- 2.03 (m, 1H) --,
Line 56, "$_D$=39.0°" should read -- $_D$= -39.0° --.
Line 63, "IR (neat) 3555" should read -- IR (neat) 3355 --.

Column 29,
Line 25, "layers wer back-extracted" should read -- layers were back-extracted --.

UNITED STATES PATENT AND TRADEMARK OFFICE
CERTIFICATE OF CORRECTION

PATENT NO. : 6,630,484 B1
DATED : October 7, 2003
INVENTOR(S) : William H. Pearson et al.

It is certified that error appears in the above-identified patent and that said Letters Patent is hereby corrected as shown below:

Column 30,
Line 14, "67.9, 51.5" should read -- 67.9, 51.6, 51.5 --,
Line 53, "epoxy-6.7" should read -- epoxy-6,7 --,
Line 59, "were backed-extracted" should read -- were back-extracted --,
Line 67, "epoxide (2RS)" should read -- epoxides (2RS) --.

Column 31,
Line 26, "calcd $C_{21}H_{20}N_3O_6NH_4$" should read -- calcd $C_{21}H_{29}N_3O_6NH_4$ --,
Line 39, "IR (neat) 2986 (w), 2862 (w)" should read -- IR (neat) 2986 (w), 2936 (w), 2862 (w) --
Line 40, (rel intensity_" should read -- (rel intensity) --.

Column 32,
Line 60, "$_D$=31.4°" should read -- $_D$= -31.4° --.

Column 33,
Line 33, "2784 (m), 1378 (m)" should read -- 2784 (m), 1455 (m), 1378 (m) --.

Column 34,
Line 12, "the acetonide" should read -- The acetonide --,
Line 16, "$R_f$32 0.23" should read -- $R_f$= 0.23 --.

Column 35,
Line 51, "$_D$= -19.3+" should read -- $_D$= -19.3° --.

Column 37,
Line 31, "(dd, J=5.6, 15.0 Hz, 1H), 224" should read -- (dd, J=5.6, 15.0 Hz, 1H), 2.24 --.

Column 38,
Line 2, "0.91 (98% crude)" should read -- 0.91 g (98% crude) --,
Line 15, "25.2, 13.9" should read -- 25.2, 22.7, 13.9 --,
Line 63, "filtered throgh" should read -- filtered through --.

Column 39,
Line 19, "CHCl$_3$/MeOH):" should read -- CHCl$_3$/MeOH); --,
Line 20, "(c 0.55 CHCl$_3$):" should read -- (c 0.55 CHCl$_3$); --,
Line 26, "(t, J=6.8 Hz, 3H):" should read -- (t, J=6.8 Hz, 3H); --.

Column 40,
Line 61, "2880 (m) cm$^{-1}$" should read -- 2880 (m), 2821 (m) cm$^{-1}$ --.

UNITED STATES PATENT AND TRADEMARK OFFICE
CERTIFICATE OF CORRECTION

PATENT NO.     : 6,630,484 B1
DATED          : October 7, 2003
INVENTOR(S)    : William H. Pearson et al.

It is certified that error appears in the above-identified patent and that said Letters Patent is hereby corrected as shown below:

Column 41,
Line 11, "deipiswainsonine" should read -- diepiswainsonine --,
Line 26, "(CI, NH$_3$)" should read -- (CI, CH$_4$ and NH$_3$) --,
Line 63, "iropylidene" should read -- isopropylidene --.

Column 42,
Line 3, "77.2" should read -- 77.3 --,
Line 7, "338.1967;" should read -- 338.1967, --,
Line 9, "67.137;" should read -- 67.13; --

Column 44,
Line 35, "162.3" should read -- 172.3 --.

Column 45,
Line 20, "2988 (m), 2102 (s)" should read -- 2988 (m), 2935 (m), 2102 (s) --,
Line 60, "stretch at 16.25" should read -- stretch at 1625 --.

Column 46,
Line 14, "2936 (m), 1621 (s)" should read -- 2936 (m), 2870 (m), 1621 (s) --,
Line 16, "[(M+NH$_4$)$^+$]" should read -- [(M+H)$^+$] --,
Line 35, "7.41" should read -- 7.51 --.

Column 47,
Line 16, "R$_f$ = -0.36" should read -- R$_f$ = 0.36 --,
Line 31, "3432 (br m), 2855 (m), 1372 (m)" should read -- 3432 (br m), 2931 (s), 2855 (m), 2800 (m), 1372 (m) --.

Column 48,
Line 25, "2926 (m), 2800 (m)" should read -- 2926 (m), 2856 (m), 2800 (m) --.

Column 49,
Line 6, "1472 (m)" should read -- 2859 (s), 1472 (m) --,
Line 23, "orthoacctate" should read -- orthoacetate --,
Line 40, "$\delta$8.59" should read -- $\delta$ 5.59 --,
Line 44, "(1.35 (s, 3H)," should read -- 1.35 (s, 3H), --,
Line 57, "diluted ether" should read -- diluted with ether --.

UNITED STATES PATENT AND TRADEMARK OFFICE
CERTIFICATE OF CORRECTION

PATENT NO. : 6,630,484 B1
DATED : October 7, 2003
INVENTOR(S) : William H. Pearson et al.

It is certified that error appears in the above-identified patent and that said Letters Patent is hereby corrected as shown below:

Column 50,
Line 4, "29.3, 25.3" should read -- 29.3, 27.9, 25.3 --,
Line 5, "MS (C1, $CH_4$ and $NH_3$)" should read -- MS (CI, $CH_4$ and $NH_3$) --,
Line 34, "hexane/BtOAc" should read -- hexane/EtOAc --,
Line 39, "12.8 Hz)," should read -- 12.8 Hz, --.

Column 51,
Line 10, "($MgSO_4$) filtered" should read -- ($MgSO_4$), filtered --,
Line 20, "[8.1 hex/EtOAc" should read -- 8:1 hex/ EtOAc --,
Line 21, "$[\alpha]^{21}$" should read -- $[\alpha]^{23}$ --,
Line 28, "(t, J=6.9 Hz, 3H):" should read -- (t, J=6.9 Hz, 3H); --,
Line 31, "MS (C1, $NH_3$) should read -- MS (CI, $NH_3$) --,
Line 34, "[(M+H$^+$]" should read [(M+H)$^+$] --,
Line 41, "(dd, J=3.9, 6.6 Hz), 1H)" should read -- (dd, J=3.9, 6.6 Hz, 1H) --, Column 52,
Line 39, "ratio=2.4:1" should read -- ratio 2.4:1 --

Column 53,
Line 16, "1.55 mg" should read -- 155 mg --,
Line 36, "dd, J=6.1 7.1" should read -- dd, J=6.1, 7.1 --,
Line 38, "11.3 Hz, $1H_{5eq}$" should read -- 11.3 Hz, 1H, $H_{5eq}$ --.

Column 54,
Line 27, "(m, 2H), 2.9" should read -- (m, 2H), 2.19 --,
Line 31, "2930 (s)" should read -- 2930 (s), --,
Line 32, "(C1, $CH_4$ and $NH_3$)" should read -- (CI, $CH_4$ and $NH_3$) --,
Line 51, "(1.22 g, 37.5 mmol)" should read -- (1.22 g, 3.75 mmol) --,
Line 61, "further purification. [A small purification was" should read -- further purification. [A small sample was --

Column 55,
Line 1, "(dd, J=5.8, 9.0 Hz,1)" should read -- (dd, J=5.8, 9.0 Hz, 1H) --.

Column 56,
Line 2, "(dd, J=15.9, 12.2 Hz, 1H)" should read -- (dd, J=5.9, 12.2 Hz, 1H) --,
Line 9, "MS (C1, $NH_3$)" should read -- MS (CI, $NH_3$) --,
Line 67, "in a dropwide" should read -- in a dropwise --.

UNITED STATES PATENT AND TRADEMARK OFFICE
CERTIFICATE OF CORRECTION

PATENT NO. : 6,630,484 B1
DATED : October 7, 2003
INVENTOR(S) : William H. Pearson et al.

It is certified that error appears in the above-identified patent and that said Letters Patent is hereby corrected as shown below:

Column 58,
Line 5, "3.66, (s, 3H)" should read -- 3.66 (s, 3H) --,
Line 49, "After 3 h, hydrogen" should read -- After 3 h, the hydrogen --,
Line 52, "was warned" should read -- was warmed --.

Column 59,
Line 6, "3Hα)," should read -- 3Hα); --,
Line 33, "Benzyloxy)" should read -- (Benzyloxy) --,
Line 37, "$CH_2Cl_2MeOH$" should read -- $CH_2Cl_2/MeOH$ --,
Line 66, "(m, 2H, $H_{7,9}$)" should read -- (m, 2H, $H_{7,9}$) --.

Column 60,
Line 1, "($CDCl_3$ 75 MHz)" should read -- ($CDCl_3$, 75 MHz) --,
Line 3, "29.9" should read -- 26.9 --,
Line 5, "100]300" should read --100],300 --,
Line 6, "(Cl, $CH_4$ and $NH_3$)" should read -- (CI, $CH_4$ and $NH_3$) --,
Line 21, "hydrolized" should be -- hydrolyzed --,
Line 26, "2H); 4.36 (m, 1H, $H_1$)" should read -- 2H), 4.36 (m, 1H, $H_1$), --,
Line 30, "(dd, J=1.8, 99.9 Hz, 1H, $H_{8\alpha}$) 2.93" should
read -- (dd, J=1.8, 99.9 Hz, 1H, $H_{8\alpha}$), 2.93 --,
Line 64, "2857 (m,)," should read -- 2857 (m), --,
Line 64, "MS (CI, $CH_4$m/z" should read -- MS (CI, $CH_4$) m/z --.

Column 61,
Line 14, "with water. 5%" should read -- with water, 5% --,
Line 16, "hexane/gradient" should read -- hexane gradient --,
Line 30, "(1S, 2R8R)" should read -- (1S, 2R, 8R) --,
Line 33, "in DMf" should read -- in DMF --,
Line 62, "ar rt" should read -- at rt --.

Column 62,
Line 4, "-4.9 IR" should read -- -4.9; IR --,
Line 24, "α-diastercomer" should read -- α-diastereomer --.

Column 63,
Line 43, "(s, 9H), 0.0091" should read -- (s, 9H), 0.091 --.

Column 64,
Line 4, "$^{-C}$NMR" should read --$^{13}$C NMR --,
Line 5, "ʿ90 MHz" should read -- (90 MHz --,
Line 25, "6)-Benzyl" should read -- 6-Benzyl --,
Line 39, "MS (Cl, $NH_3$)" should read -- MS (CI, $NH_3$)--.

UNITED STATES PATENT AND TRADEMARK OFFICE
CERTIFICATE OF CORRECTION

PATENT NO. : 6,630,484 B1
DATED : October 7, 2003
INVENTOR(S) : William H. Pearson et al.

It is certified that error appears in the above-identified patent and that said Letters Patent is hereby corrected as shown below:

Column 65,
Line 18, "3H), 0.82: should read -- 3H), 1.31 (s, 3H), 0.82 --,
Line 19, "374 (41)" should read -- 374 (41), --.

Column 66,
Line 35, "2938, 2585, 1710" should read -- 2938, 2858, 1710 --,
Line 51, "(1S, 2R, 6S, 8R, 8aR)" should read -- (1S,2R,6S,8R,8aR) --,
Line 59, "$^{13}$C NMR (90" should read --$^{13}$C NMR (90 --,
Line 62, "2939, 2849" should read -- 2939, 2859 --.

Column 67,
Line 20, "112.4 79.2" should read -- 112.4, 79.2 --,
Line 24, "438 )2.7)" should read -- 438 (2.7) --,
Line 38, "(1S,2R,6S,8R, 8aR)" should read -- (1S,2R,6S,8R,8aR) --,
Line 47, "1096, 389;" should read -- 1096, 839; --,
Line 65, "3.55 (m, 2H," should read -- 3.55 (m,2H), --.

Column 68,
Line 7, "(MH$^{+)}$ 432.2337" should read (MH$^{+}$) 432.2337 --.

Column 69,
Line 22, "(CH$_2$($_n$CH$_3$" should read -- (CH$_2$)$_n$CH$_3$ --,
Line 26, "(CO$_2$)$_n$" should read -- (CH$_2$)$_n$ --,
Line 38, "idependently" should read -- independently --.

UNITED STATES PATENT AND TRADEMARK OFFICE
CERTIFICATE OF CORRECTION

PATENT NO. : 6,630,484 B1
DATED : October 7, 2003
INVENTOR(S) : William H. Pearson et al.

It is certified that error appears in the above-identified patent and that said Letters Patent is hereby corrected as shown below:

<u>Column 70,</u>
Line 1, "triazone" should read -- triazine --,
Line 57, "thiophene, pyrrole" should read -- thiohene pyrrole --.

Signed and Sealed this

Fourteenth Day of September, 2004

JON W. DUDAS
*Director of the United States Patent and Trademark Office*